(12) United States Patent
Beaumont et al.

(10) Patent No.: US 10,435,463 B2
(45) Date of Patent: Oct. 8, 2019

(54) HEPATITIS C VIRUS SPECIFIC ANTIBODY

(71) Applicant: AIMM THERAPEUTICS B.V., Amsterdam Zuidoost (NL)

(72) Inventors: Tim Beaumont, Amsterdam Zuidoost (NL); Sabrina Julia Louisa Merat, Amsterdam Zuidoost (NL); Cornelia Johanna Schinkel, Amsterdam Zuidoost (NL); Richard Molenkamp, Amsterdam Zuidoost (NL)

(73) Assignee: ACADEMISCH MEDISCH CENTRUM, Amsterdam (NL)

(*) Notice: Subject to any disclaimer, the term of this patent is extended or adjusted under 35 U.S.C. 154(b) by 0 days.

(21) Appl. No.: 15/508,570

(22) PCT Filed: Sep. 7, 2015

(86) PCT No.: PCT/NL2015/050619
§ 371 (c)(1),
(2) Date: Mar. 3, 2017

(87) PCT Pub. No.: WO2016/036252
PCT Pub. Date: Mar. 10, 2016

(65) Prior Publication Data
US 2017/0313764 A1 Nov. 2, 2017

(30) Foreign Application Priority Data
Sep. 5, 2014 (EP) .................................. 14183805

(51) Int. Cl.
*C07K 16/10* (2006.01)
(52) U.S. Cl.
CPC ........ *C07K 16/109* (2013.01); *C07K 2317/21* (2013.01); *C07K 2317/34* (2013.01); *C07K 2317/76* (2013.01); *C07K 2317/92* (2013.01)

(58) Field of Classification Search
None
See application file for complete search history.

(56) References Cited

FOREIGN PATENT DOCUMENTS

| EP | 2481424 A1 | 8/2012 |
|---|---|---|
| WO | 2006041866 A2 | 4/2006 |
| WO | 2010035292 A1 | 4/2010 |
| WO | 2010047829 A1 | 4/2010 |
| WO | 2010047830 A2 | 4/2010 |
| WO | 2010047830 A3 | 4/2010 |
| WO | 2013033319 A2 | 3/2013 |
| WO | 2013033319 A3 | 3/2013 |

OTHER PUBLICATIONS

Law et al. (PLOS ONE, 2013, vol. 8, Issue 3, p. 1-7).*

Anonymous; Immunoglobulin kappa light chain variable region, partial [*Homo sapiens*]; GenBank: CAG27043.1, Jan. 14, 2004.
Yong Wang, et al.; Neutralizing Antibody Response to Hepatitis C Virus; Viruses, vol. 3, No. 12, Dec. 2, 2011. pp. 2127-2145.
McKay Brown, et al.; Tolerance to Single, but Not Multiple, Amino Acid Replacements in Antibody V-H CDR2: A Means of Minimizing B Cell Wastage from Somatic Hypermutation; The Journal of Immunology, The American Association of Immunologists, vol. 156, No. 9, Jan. 1, 1996, pp. 3285-3291.
Poster Session 4: HCV: Virology, Pathogenesis, and Immunology, Hepatology, vol. 60, Oct. 1, 2014, pp. 1048A-1087A.
Albecka, A., et al.; Identification of new functional regions in hepatitis C virus envelope glycoprotein E2, Journal of Virology, Feb. 2011,vol. 85, No. 4, pp. 1777-1792.
Boom, R., et al.; Rapid and simple method for purification of nucleic acids. Journal of Clinical Microbiology, Mar. 1990, vol. 28, No. 3, pp. 495-503.
Brimacombe, C., et al.; Neutralizing antibody resistant hepatitis C virus cell-to-cell transmission, Journal of Virology, Jan. 2011, vol. 85, No. 1, pp. 596-605.
Chen, Y., et al.; Selection and analysis of an optimized anti-VEGF antibody: crystal structure of an affinity-matured Fab in complex with antigen, Journal of Molecular Biology, 1999, vol. 293, No. 4, pp. 865-881.
Evans, M., et al.; Claudin-1 is a hepatitis C virus co-receptor required for a late step in entry, Nature, Apr. 2007, vol. 446, pp. 801-805.
Giang, E., et al.; Human broadly neutralizing antibodies to the envelope glycoprotein complex of hepatitis C virus, Proceedings of the National Academy of Sciences USA, Apr. 17, 2012, vol. 109, No. 16, pp. 6205-6210.
Johansson, Daniel, et al.; Human combinatorial libraries yield rare antibodies that broadly neutralize hepatitis C virus. Proceedings of the National Academy of Sciences USA, Oct. 9, 2007, vol. 104, No. 41, pp. 16269-16274.
Kabat, E., et al.; Sequences of Proteins of Immunological interest, 5th Ed. Public Health Service, National Institute of Health, Bethesda, MD (1991).
Keck, Z., et al.; Mapping a region of hepatitis C virus E2 that is responsible for escape from neutralizing antibodies and a core CD81-binding region that does not tolerate neutralization escape mutations, Journal of Virology, Oct. 2011, vol. 85, No. 20, pp. 10451-10463.
Keck, Z., et al.; Human monoclonal antibodies to a novel cluster of conformational epitopes on HCV E2 with resistance to neutralization escape in a genotype 2a isolate, PLoS Pathogens, Apr. 2012, vol. 8, No. 4, e1002653, pp. 1-21.
Keck, Z., et al.; Cooperativity in Virus Neutralization by Human Monoclonal Antibodies to Two Adjacent Regions Located at the Amino Terminus of Hepatitis C Virus E2 Glycoprotein, Journal of Virology, Jan. 2013, vol. 87, No. 1, pp. 37-51.
Khan, A., et al.; Structure of the core ectodomain of the hepatitis C virus envelope glycoprotein 2, Nature, May 15, 2014, vol. 509, pp. 381-397.
Kong, L., et al.; Hepatitis C Virus E2 Envelope Glycoprotein Core Structure, Science, Nov. 29, 2013, vol. 342, No. 6162, pp. 1090-1094.

(Continued)

*Primary Examiner* — Agnieszka Boesen
(74) *Attorney, Agent, or Firm* — Gianna J. Arnold; Saul Ewing Arnstein & Lehr LLP

(57) ABSTRACT

The invention relates to isolated, synthetic or recombinant antibodies and functional parts thereof specific for hepatitis C virus (HCV). The invention further relates to the use of such antibodies for diagnosis, treatment and prevention of HCV infection.

7 Claims, 6 Drawing Sheets

Specification includes a Sequence Listing.

(56) References Cited

OTHER PUBLICATIONS

Kwakkenbos, M., et al.; Generation of stable monoclonal antibody-producing B cell receptor-positive human memory B cells by genetic programming, Nature Medicine, Jan. 2010, vol. 16, No. 1, pp. 123-128.

Kwakkenbos, M., et al.; Genetic manipulation of B cells for the isolation of rare therapeutic antibodies from the human repertoire, Methods, Jan. 2014, vol. 65, No. 1, pp. 1-6.

Lavillette, D., et al.; Characterization of host-range and cell entry properties of the major genotypes and subtypes of hepatitis C virus, Hepatology, Feb. 2005, vol. 41, pp. 265-274.

Law, M., et al. Broadly neutralizing antibodies protect against hepatitis C virus quasispecies challenge, Nature Medicine, Jan. 2008, vol. 14, No. 1, pp. 25-27.

Liang, T., et al.; Current and Future Therapies for Hepatitis C Virus Infection, The New England Journal of Medicine, May 16, 2013, vol. 368, No. 20, pp. 1907-1917.

Lokate, A. et al.; Biomolecular interaction monitoring of autoantibodies by scanning surface plasmon resonance microarray imaging, Journal of the American Chemical Society, 2007, vol. 129, pp. 14013-14018.

Mancini, N., et al.; Hepatitis C virus (HCV) infection may elicit neutralizing antibodies targeting epitopes conserved in all viral genotypes, PLoS One, Dec. 2009, vol. 4, No. 12, e8254, pp. 1-7.

Owsianka, A., et al.; Broadly neutralizing human monoclonal antibodies to the hepatitis C virus E2 glycoprotein, Journal of General Virology, 2008, vol. 89, pp. 653-659.

Perotti, M., et al.; Identification of a broadly cross-reacting and neutralizing human monoclonal antibody directed against the hepatitis C virus E2 protein, Journal of Virology, Jan. 2008, vol. 82, pp. 1047-1052.

Pileri, P., et al.; Binding of hepatitis C virus to CD81, Science, Oct. 30, 1998, vol. 282, pp. 938-941.

Ploss, A., et al.; Human occludin is a hepatitis C virus entry factor required for infection of mouse cells, Nature, Feb. 2009, vol. 457, pp. 882-886.

Poordad, F., et al.; ABT-450/r—Ombitasvir and Dasabuvir with Ribavirin for Hepatitis C with Cirrhosis, The New England Journal of Medicine, May 22, 2014, vol. 370, No. 21, pp. 1973-1982.

Sainz, B., et al.; Identification of the Niemann-Pick C1-like 1 cholesterol absorption receptor as a new hepatitis C virus entry factor, Nature Medicine, Feb. 2012, vol. 18, No. 2, pp. 1-6.

Scarselli, E., et al.; The human scavenger receptor class B type I is a novel candidate receptor for the hepatitis C virus, The EMBO Journal, 2002, vol. 21, No. 19, pp. 5017-5025.

Schasfoort, R., et al.; Method for estimating the single molecular affinity, Analytical Biochemistry, 2012, vol. 421, No. 2, pp. 794-796.

Sulkowski, M., et al.; Daclatasvir plus Sofosbuvir for Previously Treated or Untreated Chronic HCV Infection, The New England Journal of Medicine, Jan. 16, 2014, 370, No. 3, pp. 211-221.

Wang, Y., et al.; Neutralizing antibody response to hepatitis C virus, Viruses, 2011, vol. 3, pp. 2127-2145.

Xiao, F., et al.; Hepatitis C Virus Cell-Cell Transmission and Resistance to Direct-Acting Antiviral Agents, PLoS Pathogens, May 2014, vol. 10, No. 5, e1004128, pp. 1-15.

Burioni, Roberto, et al.; Dissection of Human Humoral Immune Response Against Hepatitis C Virus E2 Glycoprotein by Repertoire Cloning and Generation of Recombinant Fab Fragments; Hepatology, 1998, pp. 810-814, vol. 28, No. 3.

Gershoni, J., et al.; Epitope Mapping—The First Step in Developing Epitope-Based Vaccines; Biodrugs, Adis International Ltd, NZ, Jan. 1, 2007, pp. 145-156, vol. 21, No. 3.

Communication dated Feb. 4, 2019 in corresponding European Patent Application No. 15 784 979.5.

\* cited by examiner

Fig. 1

HCV E2 amino acid sequences

H77
```
        .    .  400       .    .    .  420       .    .    .  440       .    .    .
ETHVTGGSAGHTTAGLVGLLTPGAKQNIQLINTNGSWHINSTALNCNDSLTTGWLAGLFYRHKFNSSGCPERL
   460    .    .    .  480       .    .    .  500       .    .    .  520       .
ASCRRLTDFAQGWGPISYANGSGLDERPYCWHYPPRPCGIVPAKSVCGPVYCFTPSPVVVGTTDRSGAPTYSW
     .    .  540       .    .    .  560       .    .    .  580       .    .    .  600
GANDTDVFVLNNTRPPLGNWFGCTWMNSTGFTKVCGAPPCVIGGVGNNTLLCPTDCFRKHPEATYSRCGSPW
          .    .    .  620       .    .    .  640       .    .    .  660       .    .    .
ITPRCMVDYPYRLWHYPCTINYTIFKVRMYVGGVEHRLEAACNWTRGERCDLEDRDRSELSPLLLSTTQWQVL
   ..680       .    .    .  700       .    .    .  720       .    .    .  740       .
PCSFTTLPALSTGLIHLHQNIVDVQYLYGVGSSIASWAIKWEYVVLLFLLLADARVCSCLWMMLLISQAEA
```

AMS.2b.20876551.kloon21
```
TTYSTGGQVSRTTSSFVGLFAHGPQQKLSLINTNGSWHINRTALNCNDSLQTGFLASLFYTRNFNSSGCPERL
SSCRTLDDFRIGWGTLEYETNVINDEDVRPYCWHYPPKPCGIVSARTVCGPVYCFTPSPVVVGTTDRQGVPTY
SWGENETDVFLLNSTRPPQGAWFGCTWMNGTGFTKTCGAPPCRIRRDYNGTLDLLCPTDCFRKHPETTYLRCG
SGPWLTPRCLVDYPYRLWHYPCTVNFTIFKVRMYVGGVEHRLPAACNFTRGDRCRLEDRDRGQQSPLLHSTTE
WAVMPCSFSDLPALSTGLLHLHQNIVDVQYLYGLSPAITRYIVKWEWVVLLFLLLADARVCACLWMLIILGQA
EA
```

```
        200       210       220       230       240       250
YQVRNSSGLYHVTNDCPNSSIVYEAADAILHTPGCVPCVREGNASRCWVAVTPTVATRDG
        260       270       280       290       300       310
KLPTTQLRRHIDLLVGSATLCSALYVGDLCGSVFLVGQLFTFSPRRHWTTQSCNCSIYPG
        320       330       340       350       360       370
HITGHRMAWDMMMNWSPTAALVVAQLLRIPQAIMDMIAGAHWGVLAGIAYFSMVGNWAKV
        380
LVVLLLFAGVDA
```

HEPATITIS C VIRUS SPECIFIC ANTIBODY

CROSS REFERENCE TO RELATED APPLICATIONS

This application claims the priority of PCT/NL2015/050619, filed on Sep. 7, 2015, which claims priority to European Patent Application No. 14183805.2, filed Sep. 5, 2014, the entire contents of each of which are hereby incorporated in total by reference.

SEQUENCE LISTING

This application incorporates by reference the Sequence Listing contained in an ASCII text file named "362346_00040_Sequence.txt" submitted via EFS-Web. The text file was created on Mar. 3, 2017, and is 2 kb in size.

FIELD OF THE INVENTION

The invention relates to the fields of biology, immunology and medicine. In particular, the invention relates to hepatitis C virus specific antibodies and uses thereof.

DESCRIPTION

Hepatitis C virus (HCV) is a positive-strand RNA virus of the Flaviviridae family. Currently seven different genotypes of HCV are known (HCV1-7), of which several genotypes are further classified into subtypes. For instance genotype 1 and 2 are classified into subtypes 1a and 1b, and subtypes 2a and 2b, respectively. The virus encodes a polyprotein that is cleaved into ten structural and non-structural proteins. The structural proteins are the two envelope glycoproteins E1 and E2. The E2 crystal structure has recently been revealed and shows a compact globular structure with a central immunoglobulin-fold beta (6) sandwich but many residues of E2 are organized in disordered, non regular secondary structures (see e.g. Khan et al. 2014 and Kong et al. 2013). E1 and E2 form non-covalent heterodimers (such heterodimer is referred to herein as a "E1E2 heterodimer" or "E1E2 protein") on the surface of the HCV virion and are involved in binding to and entry into host cells by interacting with cell surface receptors including CD81, scavenger receptor class B type 1 (SR-B1), claudin-1, occludin and Niemann-Pick C1 like 1 cholesterol absorption receptors (Pileri et al. 1998, Scarcelli et al. 2002, Evans et al. 2007, Ploss et al. 2009 and Barretto et al. 2012). Besides cell-free viral entry also cell-cell transmission by HCV has been shown to be an important mechanism for virus spreading. Factors involved in this process include scavenger receptor BI (SR-BI), CD81, tight junction proteins claudin-1 (CLDN1) and occludin (OCLN) as well as host cell kinase epidermal growth factor receptor (EGFR) and its signal transducer HRas (Xiao et al. 2014 and Bimacombe et al. 2010).

PEGylated interferon alpha alone or in combination with ribavirin is currently used as antiviral therapy for all HCV serotypes. In addition a number of small molecule protease and polymerase inhibitors, e.g. boceprevir, telaprevir, simeprevir and sofosbuvir (brand name Sovaldi), have recently been approved for the treatment of specific HCV serotypes (see e.g. Liang et al. 2013, Sulkowski et al. 2014 and Poordad et al. 2014). In addition, several monoclonal antibodies have been developed against HCV, which mainly recognize the HCV E2 glycoprotein. Further, HCV is still estimated to infect approximately 2-3% of the population worldwide and is a major cause of chronic liver disease with a risk for life-threatening diseases such as cirrhosis and hepatocellular carcinoma. There is thus still a need for therapeutic and prophylactic agents to treat and/or prevent HCV infections.

The present invention provides antibodies specific for hepatitis C virus (HCV), and functional parts and functional equivalents of such antibodies. Antibodies directed against multiple HCV genotypes and subtypes are provided. In particular provided are monoclonal antibodies that specifically recognize a conformational epitope of the HCV E2 protein and/or a conformational epitope of a HCV E1E2 heterodimer. Further, antibodies are provided that have a high binding affinity for the E2 protein and/or the E1E2 heterodimer, and/or that possess in vitro HCV neutralizing activity against multiple HCV genotypes, subtypes and/or strains. Such antibodies are useful in treatment, prevention and diagnosis of HCV infection. Provided are therefore further methods for diagnosis, treatment or prevention of HCV infection as well as uses of the antibodies for diagnosis, treatment or prevention of HCV infection. Further provided are nucleic acid molecules encoding such antibodies, vectors, host cells transformed with nucleic acids, and pharmaceutical compositions comprising HCV specific antibodies or nucleic acid molecules or vectors encoding such antibodies.

The invention provides an isolated, synthetic or recombinant antibody or functional part or functional equivalent thereof comprising:
 a heavy chain CDR1 sequence comprising a sequence which is at least 80% identical to a sequence selected from the group consisting of SEQ ID NOs: 1-5 and SEQ ID NOs 81-84, and/or
 a heavy chain CDR2 sequence comprising a sequence which is at least 80% identical to a sequence selected from the group consisting of SEQ ID NOs: 6-10 and SEQ ID NOs 85-88, and/or
 a heavy chain CDR3 sequence comprising a sequence which is at least 80% identical to a sequence selected from the group consisting of SEQ ID NOs: 11-15 and SEQ ID NOs 89-92, and/or
 a light chain CDR1 sequence comprising a sequence which is at least 80% identical to a sequence selected from the group consisting of SEQ ID NOs: 16-20 and SEQ ID NOs 93-96, and/or
 a light chain CDR2 sequence comprising a sequence which is at least 80% identical to a sequence selected from the group consisting of SEQ ID NOs: 21-25 and SEQ ID NOs 97-100, and/or
 a light chain CDR3 sequence comprising a sequence which is at least 80% identical to a sequence selected from the group consisting of SEQ ID NOs: 26-30 and SEQ ID NOs 101-104.

Said antibody or functional part or functional equivalent preferably comprises light chain and heavy chain CDRs having the sequence of:
 SEQ ID NOs 1, 6, 11, 16, 21 and 26, or
 SEQ ID NOs 2, 7, 12, 17, 22 and 27, or
 SEQ ID NOs 3, 8, 13, 18, 23 and 28, or
 SEQ ID NOs 4, 9, 14, 19, 24 and 29, or
 SEQ ID NOs 5, 10, 15, 20, 25 and 30 or
 SEQ ID NOs 81, 85, 89, 93, 97 and 101, or
 SEQ ID NOs 82, 86, 90, 94, 98 and 102, or
 SEQ ID NOs 83, 87, 91, 95, 99 and 103, or
 SEQ ID NOs 84, 88, 92, 96, 100 and 104.

Further provided is an isolated, synthetic or recombinant antibody or functional part or functional equivalent thereof that specifically binds to an epitope of hepatitis C virus (HCV) protein E2 comprising amino acids corresponding to amino acids F442, Y527, W529, G530, D535 and W616 of the H77 E2 amino acid sequence (SEQ ID NO: 145) as depicted in FIG. 1. Said antibody or functional part or functional equivalent preferably inhibits binding of HCV protein E1E2 to CD81.

Further provided is an isolated, synthetic or recombinant antibody or functional part or functional equivalent thereof that specifically binds to an epitope of hepatitis C virus (HCV) protein E2 which epitope does not comprise amino acids corresponding to amino acids N415, 5424, T435, G436, A439, L441, F442, Y443, Y485, T526, Y527, W529, G530, D535, W616, R657 and D698 of the H77 E2 amino acid sequence (SEQ ID NO: 145) as depicted in FIG. 1. Said epitope preferably does not comprise amino acids 424-443 and 523-540 of the H77 E2 amino acid sequence (SEQ ID NO: 145) as depicted in FIG. 1. Said antibody or functional part or functional equivalent preferably inhibits binding of HCV protein E1E2 to CD81. Said antibody or functional part or functional equivalent preferably specifically binds to an epitope of hepatitis C virus (HCV) protein E2 which epitope does not comprise amino acids corresponding to amino acids L413, N415, G418, W420, N423, S424, T435, G436, A439, L441, F442, Y443, N448, Y485, T526, Y527, W529, G530, N532, D533, T534, D535, V538, P612, W616, R657, P664, P676 and D698 of the H77 E2 amino acid sequence as depicted in FIG. 1 (SEQ ID NO: 145).

Further provided is an isolated, synthetic or recombinant antibody or functional part or functional equivalent thereof that competes with antibody AT12-011 as described herein for binding to HCV protein E2, preferably HCV genotype 1 and/or genotype 2 protein E2.

Further provided is an isolated, synthetic or recombinant antibody or functional part or functional equivalent thereof that competes with antibody AT12-007 as described herein for binding to HCV protein E2.

Further provided is an isolated, synthetic or recombinant antibody or functional part or functional equivalent thereof that competes with antibody AT12-009 as described herein for binding to HCV protein E2.

Further provided is an isolated, synthetic or recombinant antibody or functional part or functional equivalent thereof that competes with antibody AT12-010 as described herein for binding to HCV protein E2.

Further provided is an isolated, synthetic or recombinant antibody or functional part or functional equivalent thereof that competes with antibody AT13-021 as described herein for binding to HCV protein E2.

Further provided is an isolated, synthetic or recombinant antibody or functional part or functional equivalent thereof that competes with antibody AT15-009 as described herein for binding to HCV protein E2.

Further provided is an isolated, synthetic or recombinant antibody or functional part or functional equivalent thereof that competes with antibody AT15-011 as described herein for binding to a HCV E1E2 heterodimer.

Further provided is an isolated, synthetic or recombinant antibody or functional part or functional equivalent thereof that competes with antibody AT15-012 as described herein for binding to HCV protein E2.

Further provided is an isolated, synthetic or recombinant antibody or functional part or functional equivalent thereof that competes with antibody AT15-015 as described herein for binding to a HCV E1E2 heterodimer.

As used herein, the term "H77 E2 amino acid sequence as depicted in FIG. 1" means the amino acid sequence of the E2 protein of HCV strain H77, as depicted in FIG. 1 (SEQ ID NO: 145).

FIG. 9 depicts the amino acid sequence of the E1 protein (corresponding to residues 192-383 of the HCV polyprotein) from HCV genotype 1a, strain H77 (Genbank accession number AAB67037) (SEQ ID NO: 147).

The term "antibody" as used herein, refers to an immunoglobulin protein comprising at least a heavy chain variable region (VH), paired with a light chain variable region (VL) that is specific for a target epitope.

A "functional part of an antibody" is defined herein as a part that has at least one shared property as said antibody in kind, not necessarily in amount. Said functional part is capable of binding the same antigen as said antibody, albeit not necessarily to the same extent. In one embodiment a functional part of an antibody comprises at least a heavy chain variable domain (VH). Non-limiting examples of a functional part of an antibody are a single domain antibody, a single chain antibody, a nanobody, an unibody, a single chain variable fragment (scFv), a Fab fragment and a F(ab')$_2$ fragment.

A "functional equivalent of an antibody" is defined herein as an artificial binding compound, comprising at least one CDR sequence of an antibody. Said functional equivalent preferably comprises the heavy chain CDR1, CDR2 and CDR3 sequences of an antibody, as well as the light chain CDR1, CDR2 and CDR3 sequence of said antibody. A functional equivalent of an antibody is for instance produced by altering an antibody such that at least an antigen-binding property of the resulting compound is essentially the same in kind, not necessarily in amount. This can be done in many ways, for instance through conservative amino acid substitution, whereby an amino acid residue is substituted by another residue with generally similar properties (size, hydrophobicity, etc), such that the overall functioning of the antibody is essentially not affected.

As is well known by the skilled person, a heavy chain of an antibody is the larger of the two types of chains making up an immunoglobulin molecule. A heavy chain comprises a constant domain and a variable domain, which variable domain is involved in antigen binding. A light chain of an antibody is the smaller of the two types of chains making up an immunoglobulin molecule. A light chain comprises a constant domain and a variable domain. The variable domain is often, but not always, together with the variable domain of the heavy chain involved in antigen binding. Complementary-determining regions (CDRs) are the hypervariable regions present in heavy chain variable domains and light chain variable domains. In case of whole antibodies, the CDRs 1-3 of a heavy chain and the CDRs 1-3 of the connected light chain together form the antigen-binding site.

As used herein, the terms "specific for" and "specifically binds" or "capable of specifically binding" are used interchangeably and refer to the interaction between an antibody, or functional part or functional equivalent thereof, and its epitope, indicating that said antibody or functional part or functional equivalent preferentially binds to said epitope over other antigens or amino acid sequences. Thus, although the antibody, functional part or functional equivalent may non-specifically bind to other antigens or amino acid sequences, the binding affinity of said antibody or functional part or functional equivalent for its epitope is significantly higher than the non-specific binding affinity of said antibody or functional part or functional equivalent for any other antigen or amino acid sequence. The terms "specifically binds" and "specifically binding" as used herein refer to the process of a non-covalent interaction between an antibody according to the invention and an epitope, for instance an epitope of the E2 protein of HCV and/or an epitope of a E1E2 heterodimer of HCV. It is noted that an antibody or functional part or functional equivalent according to the invention that is able to bind a particular epitope of the E2 protein and/or E1E2 heterodimer of HCV can also be specific for other, non-HCV epitopes if said epitope is also present on another protein (or cell). In that case an antibody referred to herein as being specific for the E2 protein and/or E1E2 heterodimer of HCV is also specific for such other protein or cell comprising the same epitope.

"Binding affinity" refers to the strength of the total sum of the noncovalent interactions between a single binding site of an antibody or functional part or functional equivalent and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity can generally be represented by the equilibrium dissociation constant ($K_D$), which is calculated as the $k_a$ to $k_d$ ratio, see, e.g., Chen, Y., et al., 1999. Affinity can be measured by common methods known in the art, such as for instance a surface plasmon resonance (SPR) assay such as BiaCore or IBIS-iSPR instrument at IBIS Technologies BV (Hengelo, the Netherlands) or solution phase assays, such as Kinexa.

The percentage of identity of an amino acid sequence or nucleic acid sequence, or the term "% sequence identity", is defined herein as the percentage of residues of the full length of a candidate amino acid sequence or nucleic acid sequence that is identical with the residues in a reference amino acid sequence or nucleic acid sequence after aligning the two sequences and introducing gaps, if necessary, to achieve the maximum percent identity. Methods and computer programs for the alignment are well known in the art, for example "Align 2".

A "HCV genotype" as used herein refers to genetically different hepatitis C viruses. Examples of HCV genotypes are HCV1a, HCV1b, HCV2a, HCV2b, HCV3, HCV4, HCV5, HCV6 and HCV7. "HCV strains" as used herein refers to different HCV of the same subtype, for example HCV1a strains, UKN1A14.8 and UKN1A14.36, HCV1b strain UKN1B12.6, HC2a strain UKN2A2.4, HCV2b strains AMS.2b.20876551.kloon21, UKN2B1.1 and UKN2B2.8, HCV3 strains UKN3a 1.28 and UKN3A13.6, HCV4 strains UKN4.11.1, UKN4.21.16 and UKN4.21.16, HCV5 strains UKN5.14.4 and UKN5.15.11 and HCV6 strain UKN6.5.340.

"Neutralizing activity" as used herein is defined as the inhibition or reduction of a HCV's capacity of infecting a host cell. Neutralizing activity of an antibody can be measured by any method known in the art, for instance by measuring the ability of the antibody to lower the titer of infectious virus in vitro in cultured cells. One of such methods is detailed in the Examples of this application and involves the inhibition of cell entry of HCV pseudoparticles (HCVpp) produced in 293T/17 cells by co-transfecting plasmids (vector containing E1E2 sequence, phCMV-gag/pol and phCMV-luciferase) by monoclonal antibodies. In this method, 293T/17 cell culture supernatants containing HCVpp are mixed with B-cell culture supernatants or isolated antibodies and after 1 hour of incubation added to, for instance, huh-7 cells. After for instance 3 days, cell entry of HCVpp can be measured for instance directly by luciferase activity. Neutralizing antibodies will prevent or reduce HCVpp cell entry of the target cell. Neutralizing activity can be quantified by measurement of the IC50 or "IC90". "IC50" and "IC90" are terms well known in the art and refers to the concentration of HCVpp neutralizing antibody necessary to inhibit or reduce HCVpp infectivity of host cells by, respectively, 50% or 90%. The lower the IC50 of IC90 value of an antibody, the stronger the neutralizing activity of the antibody, and the greater its potential as a therapeutic agent.

Antibodies according to the invention are specific for the E2 protein and/or E1E2 protein (heterodimer) of HCV. They are capable of specifically binding the E2 protein and/or E1E2 protein of at least one HCV genotype, preferably of multiple HCV genotypes. Preferred antibodies of the invention are specific for a conformational epitope of the HCV E2 protein and/or E1E2 protein. A "conformational epitope" is herein defined as an epitope that is formed by the amino acid sequence and the three-dimensional shape of an antigen (e.g. as a result of folding and/or interactions between individual amino acids). The amino acids making up the epitope can be relatively few in number and can be spread along the length of the antigen. Such epitope is brought into the correct conformation via folding of the antigen. In general, antibodies recognizing conformational epitopes have broader specificity for multiple HCV genotypes and/or strains because conformational epitopes are more conserved. Such antibodies may therefore offer broader therapeutic application for treating or preventing HCV infection than antibodies that bind only linear epitopes.

Preferred antibodies according to the invention are specific for an epitope of HCV protein E2 comprising amino acids that correspond to amino acids F442, Y527, W529, G530, D535 and W616 of the H77 E2 amino acid sequence as depicted in FIG. 1(SEQ ID NO: 145). F442 indicates phenylalanine at amino acid position 442 of the H77 E2 protein as depicted in FIG. 1 (SEQ ID NO: 145). Y527 indicates tyrosine at amino acid position 527 of the H77 E2 protein as depicted in FIG. 1(SEQ ID NO: 145). W529 indicates tryptophan at amino acid position 529 of the H77 E2 protein as depicted in FIG. 1 (SEQ ID NO: 145). G530 indicates glycine at amino acid position 530 of the H77 E2 protein as depicted in FIG. 1 (SEQ ID NO: 145). D535 indicates aspartic acid at amino acid position 535 of the H77 E2 protein as depicted in FIG. 1 (SEQ ID NO: 145). W616 indicates tryptophan at amino acid position 616 of the H77 E2 protein as depicted in FIG. 1 (SEQ ID NO: 145). This epitope comprising amino acids F442, Y527, W529, G530, D535 and W616 of the H77 E2 amino acid sequence as depicted in FIG. 1 (SEQ ID NO: 145) is conserved over different HCV genotypes and strains. FIG. 1 shows the amino acid sequence of the HCV E2 protein of HCV genotype 1a, strain H77 (derived from Genbank accession No. AAB67037 with three amino acid changes: R564C, V566A, and G650E). The term "amino acids corresponding to amino acids F442, Y527, W529, G530, D535 and W616 of the H77 E2 amino acid sequence as depicted in FIG. 1" means that in HCV genotypes and strains other than HCV genotype 1a, strain H77 the amino acid positions of the epitope may vary, but they correspond to the indicated amino acids of HCV1a H77 as depicted in FIG. 1. Although HCV antibodies have been described that recognize an epitope of E2 comprising amino acids F442, Y527, W529, G530 and/or D535, e.g. CBH2, HC11, HC1, AR3A, AR3B, AR3C, AR3D, A8, 1:7, e20 and e137 (Wang et al. 2011), antibodies that recognize an epitope comprising amino acids F442, Y527, W529, G530, D535 and W616 of the H77 E2 amino acid sequence as depicted in FIG. 1 have not been described before the present invention. Preferably, an antibody or functional part or functional equivalent that specifically binds to an epitope of HCV protein E2 comprising amino acids F442, Y527, W529, G530, D535 and W616 of the H77 E2 amino acid sequence as depicted in FIG. 1 binds said epitope of at least one HCV genotype selected from the group consisting of HCV1a, HCV1b, HCV2a, HCV2b, HCV3, HCV4, HCV5, HCV6 and HCV7, more preferably of at least two HCV genotypes selected from said group, more preferably of at least three HCV genotypes selected from said group, more preferably of at least four HCV genotypes selected from said group, more preferably of at least five HCV genotypes selected from said group. Most preferably said antibody or functional part or functional equivalent specifically binds said epitope of the E2 protein of HCV1a, HCV1b, HCV2a, HCV2b, HCV3, HCV4, HCV5 and HCV6. Most preferably said epitope further comprises one or more amino acids corresponding to amino acids selected from the group consisting of S424, G436, L441, Y443 and T526 of the H77 E2 amino acid sequence as depicted in FIG. 1. S424 indicates serine at amino acid position 424 of the H77 E2 protein as depicted in FIG. 1. G436 indicates glycine at amino acid position 436 of the H77 E2 protein as depicted in FIG. 1. L441 indicates leucine at amino acid position 441 of the H77 E2 protein as depicted in FIG. 1. Y443 indicates tyrosine at amino acid position 443 of the H77 E2 protein as depicted in FIG. 1. T526 indicates threonine at amino acid position 526 of the H77 E2 protein as depicted in FIG. 1. Provided is therefore an isolated, synthetic or recombinant antibody or functional part or functional equivalent thereof that specifically binds to an epitope of HCV protein E2 comprising amino acids F442, Y527, W529, G530, D535 and W616 and one or more amino acids selected from the group consisting of S424, G436, L441, Y443 and T526 of the H77 E2 amino acid sequence as depicted in FIG. 1, or amino acids corresponding thereto. Preferably said epitope comprises amino acids corresponding to amino acids F442, Y527, W529, G530, D535, W616, S424, G436, L441, Y443 and T526 of the H77 E2 amino acid sequence as depicted in FIG. 1. In HCV genotypes and strains other than HCV genotype 1a, strain H77 the amino acid positions of the epitope may vary, but they correspond to the indicated amino acids of HCV strain H77 as depicted in FIG. 1. As is demonstrated in the Examples, antibodies AT12-007, AT12-009, AT12-010 and AT13-021 specifically recognize an epitope of the HCV E2 protein comprising amino acids S424, L441, F442, Y527, W529, G530, D535 and W616 of the H77 E2 amino acid sequence as depicted in FIG. 1. Antibodies AT12-007, AT12-009, AT12-010 and AT13-021 having heavy chain and light chain CDR and variable region sequences as depicted in Table 1, and variant antibodies thereof, are preferred antibodies according to the invention. Such variant antibody has at least 80%, more preferably at least 85%, more preferably at least 90%, more preferably at least 95% or at least 96% or at least 97% or at least 98% or at least 99% sequence identity with the heavy and light chain CDR1, CDR2 and CDR3 sequences of antibody AT12-007, AT12-009, AT12-010 or AT13-021, more preferably with the heavy and light chain variable region sequences of antibody AT12-007, AT12-009, AT12-010 or AT13-021.

Further preferred antibodies according to the invention are specific for an epitope of HCV protein E2 which epitope does not comprise amino acids corresponding to amino acids N415, S424, T435, G436, A439, L441, F442, Y443, Y485, T526, Y527, W529, G530, D535, W616, R657 and D698 of the H77 E2 amino acid sequence as depicted in FIG. 1. Preferably, said epitope does not comprise amino acids corresponding to amino acids L413, N415, G418, W420, N423, S424, T435, G436, A439, L441, F442, Y443, N448, Y485, T526, Y527, W529, G530, N532, D533, T534, D535, V538, P612, W616, R657, P664, P676 and D698 of the H77 E2 amino acid sequence as depicted in FIG. 1. Preferably said antibodies or functional parts or functional equivalents are specific for an epitope that does not comprise amino acids 424-443 and 523-540 of the H77 E2 amino acid sequence as depicted in FIG. 1. L413 indicates leucine at amino acid position 413 of the H77 E2 protein as depicted in FIG. 1. N415 indicates asparagine at amino acid position 415 of the H77 E2 protein as depicted in FIG. 1. G418 indicates glycine at amino acid position 418 of the H77 E2 protein as depicted in FIG. 1. W420 indicates tryptophan at amino acid position 420 of the H77 E2 protein as depicted in FIG. 1. N423 indicates asparagine at amino acid position 423 of the H77 E2 protein as depicted in FIG. 1. T435 indicates threonine at amino acid position 435 of the H77 E2 protein as depicted in FIG. 1. A439 indicates alanine at amino acid position 439 of the H77 E2 protein as depicted in FIG. 1. N448 indicates asparagine at amino acid position 448 of the H77 E2 protein as depicted in FIG. 1. Y485 indicates tyrosine at amino acid position 485 of the H77 E2 protein as depicted in FIG. 1. N532 indicates asparagine at amino acid position 532 of the H77 E2 protein as depicted in FIG. 1. D533 indicates aspartic acid at amino acid position 533 of the H77 E2 protein as depicted in FIG. 1. T534 indicates threonine at amino acid position 534 of the H77 E2 protein as depicted in FIG. 1. V538 indicates valine at amino acid position 538 of the H77 E2 protein as depicted in FIG. 1. P612 indicates proline at amino acid position 612 of the H77 E2 protein as depicted in FIG. 1. R657 indicates arginine at amino acid position 657 of the H77 E2 protein as depicted in FIG. 1. P664 indicates proline at amino acid position 664 of the H77 E2 protein as depicted in FIG. 1. P676 indicates proline at amino acid position 676 of the H77 E2 protein as depicted in FIG. 1. D698 indicates aspartic acid at amino acid position 698 of the H77 E2 protein as depicted in FIG. 1. As is demonstrated in the Examples, antibody AT12-011 specifically recognizes an epitope of the HCV E2 protein which epitope does not comprise amino acids corresponding to amino acids L413, N415, G418, W420, N423, S424, T435, G436, A439, L441, F442, Y443, N448, Y485, T526, Y527, W529, G530, N532, D533, T534, D535, V538, P612, W616, R657, P664, P676 and D698 of the H77 E2 amino acid sequence as depicted in FIG. 1. Antibody AT12-011 having a heavy chain and light chain variable region sequence as depicted in Table 1, and variant antibodies thereof are therefore preferred antibodies according to the invention. Such variant antibodies have at least 80%, more preferably at least 85%, more preferably at least 90%, more preferably at least 95% or at least 96% or at least 97% or at least 98% or at least 99% sequence identity with the heavy and light chain CDR1, CDR2 and CDR3 sequences of antibody AT12-011, more preferably with the heavy and light chain variable region sequences of antibody AT12-011. Particularly preferred antibodies or functional parts or functional equivalents thereof specific for an epitope of the HCV E2 protein which epitope does not comprise amino acids corresponding to amino acids N415, S424, T435, G436, A439, L441, F442, Y443, Y485, T526, Y527, W529, G530, D535, W616, R657 and D698 of the H77 E2 amino acid sequence as depicted in FIG. 1, and which preferably does not comprise amino acids corresponding to amino acids L413, N415, G418, W420, N423, S424, T435, G436, A439, L441, F442, Y443, N448, Y485, T526, Y527, W529, G530, N532, D533, T534, D535, V538, P612, W616, R657, P664, P676 and D698 of the H77 E2 amino acid sequence as depicted in FIG. 1, comprise at least the heavy chain and light chain CDRs 1-3 of antibody AT12-011. Also provided is an antibody or functional part or functional equivalent that specifically binds to the same epitope as antibody AT12-011. Further provided is an antibody or functional part or functional equivalent that competes with antibody AT12-011 for specific binding to HCV protein E2. Said antibody or functional part or functional equivalent preferably competes with antibody AT12-011 for specific binding to HCV genotype 1 and/or 2 protein E2.

All currently known antibodies that bind a conformational epitope in the HCV E2 protein specifically bind an epitope which comprises at least one amino acid from the amino acids 424-443 and 523-540 of the H77 E2 amino acid sequence as depicted in FIG. 1. Antibodies and functional parts and functional equivalents according to the invention that are specific for an epitope that does not comprise amino acids N415, S424, T435, G436, A439, L441, F442, Y443, Y485, T526, Y527, W529, G530, D535, W616, R657 and D698 of the H77 E2 protein as depicted in FIG. 1, which epitope preferably does not comprise amino acids corresponding to amino acids L413, N415, G418, W420, N423, S424, T435, G436, A439, L441, F442, Y443, N448, Y485, T526, Y527, W529, G530, N532, D533, T534, D535, V538, P612, W616, R657, P664, P676 and D698 of the H77 E2 amino acid sequence as depicted in FIG. 1, thus bind to a unique epitope in the HCV E2 protein, which epitope has not been described before the present invention. Such antibodies, functional parts or functional equivalents according to the invention can be advantageously combined with an antibody that specifically recognizes a conformational epitope of the E2 protein that comprises at least one amino acid selected from the amino acids 424-443 and 523-540 of the H77 E2 amino acid sequence as depicted in FIG. 1, for instance an epitope comprising amino acids corresponding to S424, L441, F442, Y527, W529, G530 and/or D535 of the H77 E2 protein. As demonstrated in the Examples, antibody AT12-011, which is specific for an epitope in the HCV E2 protein which epitope does not comprise amino acids corresponding to amino acids L413, N415, G418, W420, N423, S424, T435, G436, A439, L441, F442, Y443, N448, Y485, T526, Y527, W529, G530, N532, D533, T534, D535, V538, P612, W616, R657, P664, P676 and D698 of the H77 E2 amino acid sequence, does not compete with antibodies AT12-007, AT12-009, AT12-010 and AT13-021, which are all specific for an epitope of the H77 E2 protein comprising at least amino acids F442, Y527, W529, G530 and D535. This means that antibody AT12-011 and one of antibodies AT12-007, AT12-009, AT12-010 and AT13-021 are able to simultaneously bind the E2 protein. Other antibodies that specifically bind an epitope of the E2 protein comprising at least one amino acid selected from the group consisting of amino acids 424-443 and 523-540 of the H77 E2 amino acid sequence are CBH2, HC11, HC1, AR3A, AR3B, AR3C, AR3D, A8, 1:7, e20 and e137 (Wang et al. 2011). An antibody or functional part or functional equivalent according to the invention that specifically binds to an epitope of HCV protein E2 which epitope does not comprise amino acids corresponding to amino acids N415, S424, T435, G436, A439, L441, F442, Y443, Y485, T526, Y527, W529, G530, D535, W616, R657 and D698 of the H77 E2 amino acid sequence, or an antibody or functional part or functional equivalent according to the invention that competes with antibody AT12-011 for binding to HCV protein E2, and an antibody specific for a conformational epitope of the E2 protein that comprises at least one amino acid selected from the amino acids 424-443 and 523-540 of the H77 E2 amino acid sequence, for instance an epitope comprising amino acids F442, Y527, W529, G530 and D535 of the H77 E2 protein, are thus advantageously combined in a single treatment regime in view of their different binding specificities. Likewise, an antibody or functional part or functional equivalent according to the invention that specifically binds to an epitope of HCV protein E2 which epitope does not comprise amino acids corresponding to amino acids L413, N415, G418, W420, N423, S424, T435, G436, A439, L441, F442, Y443, N448, Y485, T526, Y527, W529, G530, N532, D533, T534, D535, V538, P612, W616, R657, P664, P676 and D698 of the H77 E2 amino acid sequence as depicted in FIG. 1, and an antibody specific for a conformational epitope of the E2 protein that comprises at least one amino acid selected from the amino acids 424-443 and 523-540 of the H77 E2 amino acid sequence, for instance an epitope comprising amino acids F442, Y527, W529, G530 and D535 of the H77 E2 protein, are advantageously combined in a single treatment regime in view of their different binding specificities. In some embodiments, an antibody or functional part or functional equivalent according to the invention that specifically binds to an epitope of HCV protein E2 which epitope does not comprise amino acids corresponding to amino acids L413, N415, G418, W420, N423, S424, T435, G436, A439, L441, F442, Y443, N448, Y485, T526, Y527, W529, G530, N532, D533, T534, D535, V538, P612, W616, R657, P664, P676 and D698 of the H77 E2 amino acid sequence as depicted in FIG. 1, and an antibody selected from the group consisting of AT15-009, AT15-011, AT15-012 and AT15-015, are advantageously combined in a single treatment regime in view of their different binding specificities.

By combining such antibodies, multiple different targets in the E2 protein and/or E1E2 protein are recognized during the same therapy. This way, a more potent HCV treatment is obtained and it will be more difficult for the virus to develop antibody escape mutants. Such a combination will thus result in more effective treatment and/or prevention of HCV infection and/or a HCV related disorder. With a HCV related disorder is meant a disorder that is present in an individual that is infected with HCV and that is at least in part a result of said HCV infection. In some embodiments, an antibody combination according to the invention allows for the use of less antibody as compared to current mAb therapies, due to the combined, potent, action of said combination according to the invention. It is favourable to use an antibody amount as low as possible to achieve a desired effect from both a health care of view (it is preferred to administer to a subject as less as possible of any substance), and from an economical point of view (a reduction of the amount of therapeutic antibody needed generally reduces the cost of the treatment). In alternative embodiments, with a similar amount of antibody as compared to current mAb therapies, a more effective treatment and/or prevention of HCV infection and/or a HCV related disorder is achieved when using an antibody combination according to the present invention. Provided is therefore a combination of an isolated, synthetic or recombinant antibody or functional part or functional equivalent thereof that specifically binds to an epitope of HCV protein E2 which epitope does not comprise amino acids corresponding to amino acids N415, S424, T435, G436, A439, L441, F442, Y443, Y485, T526, Y527, W529, G530, D535, W616, R657 and D698 of the H77 E2 amino acid sequence as depicted in FIG. 1, or an isolated, synthetic or recombinant antibody or functional part or functional equivalent that competes with antibody AT12-011 for binding to HCV protein E2, in combination with an isolated, synthetic or recombinant antibody or functional part or functional equivalent that is specific for a conformational epitope of the E2 protein that comprises at least one amino acid selected from the amino acids 424-443 and 523-540 of the H77 E2 amino acid sequence, preferably comprising amino acids F442, Y527, W529, G530 and D535, of the H77 E2 protein. Also provided is a combination of an isolated, synthetic or recombinant antibody or functional part or functional equivalent thereof that specifically binds to an epitope of HCV protein E2 which epitope does not comprise amino acids corresponding to amino acids L413, N415, G418, W420, N423, S424, T435, G436, A439, L441, F442, Y443, N448, Y485, T526, Y527, W529, G530, N532, D533, T534, D535, V538, P612, W616, R657, P664, P676 and D698 of the H77 E2 amino acid sequence as depicted in FIG. 1, in combination with an isolated, synthetic or recombinant antibody or functional part or functional equivalent that is specific for a conformational epitope of the E2 protein that comprises at least one amino acid selected from the amino acids 424-443 and 523-540 of the H77 E2 amino acid sequence, preferably comprising amino acids F442, Y527, W529, G530 and D535, of the H77 E2 protein. A preferred combination is an antibody or functional part or functional equivalent comprising the heavy chain and light chain CDRs 1-3 of antibody AT12-011 and an antibody or functional part or functional equivalent comprising the heavy chain and light chain CDRs 1-3 of an antibody selected from the group consisting of AT12-007, AT12-009, AT12-010, AT13-021, AT15-009, AT15-011, AT15-012, AT15-015, CBH2, HC11, HC1, AR3A, AR3B, AR3C, AR3D, A8, 1:7, e20 and e137, preferably of an antibody selected from the group consisting of AT12-007, AT12-009, AT12-010, AT13-021, AT15-009, AT15-011, AT15-012 and AT15-015. A particularly preferred combination is that of antibody AT12-011 and one or more antibodies selected from the group consisting of AT12-007, AT12-009, AT12-010, AT13-021, AT15-009, AT15-011, AT15-012 and AT15-015.

Preferred antibodies, functional parts or functional equivalents thereof provided by the present invention have a high binding affinity for the HCV E2 protein and/or E1E2 protein. Such antibodies, functional parts or functional equivalents thereof preferably have a binding affinity for protein E2 of HCV genotype 1a, preferably for soluble protein E2, with a dissociation constant ($K_D$) of 0.7 nM or less and/or an affinity for soluble protein E2 of HCV genotype 2b with a $K_D$ of 2.5 nM or less under the SPR experimental conditions of Example 1. Preferably an antibody or functional part or functional equivalent according to the invention has a binding affinity for the E2 protein of HCV genotype 1a, preferably for the E2 protein of HCV1a strain H77, with a dissociation constant ($K_D$) of 0.6 nM or less, more preferably 0.5 nM or less, more preferably 0.4 nM or less, more preferably 0.35 nM or less under the SPR experimental conditions of Example 1. Preferably an antibody or functional part or functional equivalent according to the invention has a binding affinity for the E2 protein of HCV genotype 2b, preferably for the E2 protein of HCV2b strain AMS.2b.20876551.kloon21 (SEQ ID NO: 146), with a dissociation constant ($K_D$) of 2 nM or less, more preferably 1.5 nM or less, more preferably 1.0 nM or less, more preferably 0.5 nM or less, more preferably 0.4 nM or less, more preferably 0.3 nM or less, more preferably 0.25 nM or less under the SPR experimental conditions of Example 1. In some embodiments, an antibody or functional part or functional equivalent according to the invention has a binding affinity for the E2 protein of HCV genotype 1a, preferably for the E2 protein of HCV1a strain H77, with a dissociation constant ($K_D$) of 0.25 nM or less, more preferably 0.242 nM or less, more preferably 0.15 nM or less, more preferably 0.10 nM or less, more preferably 0.05 nM or less, more preferably 0.04 nM or less, more preferably 0.03 nM or less, more preferably 0.02 nM or less, more preferably 0.015 nM or less under the SPR experimental conditions of Example 2. Binding affinity of an antibody or functional part or functional equivalent specific for an epitope of HCV E2 protein comprising one or more amino acids within the region of amino acids 412-423 of the E2 protein as depicted in FIG. 1 can be measured by common methods known in the art, such as for instance a surface plasmon resonance (SPR) assay such as BiaCore or IBIS-iSPR instrument at IBIS Technologies BV (Hengelo, the Netherlands) or solution phase assays, such as Kinexa. Preferably the binding affinity of such antibody or functional part or functional equivalent for isolated protein E2 is measured, in particular after protein E2 has been incubated with an antibody or functional part or functional equivalent according to the invention. Protein E2 and said antibody, functional part or functional equivalent according to the invention are for instance pre-incubated for 1-5 minutes before said antibody or functional part or functional equivalent specific for an epitope of HCV E2 protein comprising one or more amino acids within the region of amino acids 412-423 of the E2 protein is added and binding affinity thereof is measured.

In some embodiments, an antibody or functional part or functional equivalent according to the invention has a binding affinity for the E1E2 heterodimer of HCV genotype 1a, preferably for the E1E2 heterodimer of HCV1a strain H77, with a 50% effective concentration (EC50) of 0.0019 μg/mL or less, more preferably 0.0009 μg/mL or less, under the experimental conditions of the E1E2 binding assay as described in Example 2.

An antibody, functional part or functional equivalent according to the invention preferably exhibits neutralizing activity against at least one HCV genotype. Such neutralizing antibody or functional part or functional equivalent is useful in the prophylactic or therapeutic treatment of a HCV infection. Preferred antibodies or functional parts or functional equivalents exhibit neutralizing activity against at least two HCV genotypes, preferably at least two genotypes selected from HCV1a, HCV1b, HCV2a and HCV2b. Other preferred antibodies or functional parts or functional equivalents in addition exhibit neutralizing activity against HCV3, HCV4, HCV5 and/or HCV6. Preferably a HCV neutralizing antibody or functional part or functional equivalent according to the invention has said in vitro neutralizing activity as determined in a neutralization assay as described in the Examples by determining the ability of an antibody or functional part or functional equivalent to inhibit cell entry of HCVpp. An antibody or functional part or functional equivalent according to the invention may have HCV neutralizing activity in the presence of complement, whereby a chain of events leading to complement-mediated cell lysis is initiated, or have complement-independent neutralizing activity, which is independent from complement. The presence of neutralizing activity independent of complement is for instance determined by testing neutralizing activity of an antibody or functional part or functional equivalent both in the presence and absence of added complement. If the neutralizing activity is higher in the presence of complement, the antibody or functional part or functional equivalent exhibits complement-dependent neutralizing activity. If the neutralizing activity is comparable in the presence and absence of complement, the neutralizing activity is complement-independent. Preferred antibodies, functional parts or functional equivalents provided by the invention have a high neutralizing activity. An advantage of such antibodies and functional parts and functional equivalents is that a low dosage thereof is needed in order to obtain neutralizing capacity. Generally, the higher the neutralizing activity of an antibody, the lower the amount of antibody necessary for treatment of an individual. Therefore, in case of a high neutralizing activity, less of said neutralizing antibody or functional part or functional equivalent has to be administered to an individual for treatment and/or prevention of HCV infection. It is favourable to use an amount as low as possible to achieve a desired effect from both a health care point of view and from an economical point of view. It is preferred to administer to a subject as less as possible of a therapeutic antibody or functional part or functional equivalent, because this reduces the chance of undesired effects, such as immunological reactions. Furthermore, if a lower amount of antibody or functional part or functional equivalent is used, the costs of treatment of an individual to prevent or counteract HCV infection are reduced.

Preferred antibodies, functional parts or functional equivalents according to the invention are capable of inhibiting binding of HCV protein E1E2 to CD81. CD81 is a cell surface receptor that is expressed on the surface of potential host cells for HCV. HCV proteins E1 and E2 form non-covalent heterodimers on the surface of the HCV envelope and these heterodimers are involved in binding to and entry into host cells by interacting with, inter alia, CD81. Without being bound by theory, it is believed that antibodies, functional parts or functional equivalents according to the invention that inhibit binding of HCV protein E1E2 to CD81 thus exert their HCV neutralizing ability by reducing CD81 dependent binding to and entry into host cells. As is demonstrated in Example 1 (see e.g. FIG. 5) antibodies AT12-007, AT12-009, AT12-010, AT12-011 and AT13-021 are able to inhibit binding of E1E2 to CD81. As used herein "inhibit binding of E1E2 to CD81" refers to any reduction in the ability of E1E2 to bind to CD81. Preferably, binding of E1E2 to CD81 is reduced by at least 25%, more preferably by at least 50%, more preferably by at least 75%, more preferably by at least 90%. Inhibition of binding of E1E2 to CD81 and the percentage thereof is for instance determined using a method as described herein in the Examples, using an appropriate concentration of antibody or functional part or functional equivalent. This method involves detecting binding by flow cytometry, e.g. by pre-incubating E1E2 transfected cells with antibody or functional part or functional equivalent and subsequently adding the large extracellular loop (LEL) of CD81, which contains a label, such as for instance a mouse Fc tail, which can be detected by a labeled anti-mouse Fc antibody to detect intracellular CD81 binding. The level of inhibition is for instance calculated by dividing the percentage of positive cells from each well by the mean percentage of positive cells from wells where cells are incubated without antibody or functional part or functional equivalent.

An antibody, functional part or functional equivalent according to the present invention preferably comprises a human heavy chain variable region and/or a human light chain variable region. More preferably, said binding compound comprises a human heavy chain constant region and a human heavy chain variable region, preferably in combination with a human light chain constant region and a human light chain variable region. More preferably, an antibody according to the invention is a human antibody, a chimeric antibody or a humanized antibody. Most preferably, an antibody according to the invention is a human antibody. The use of human antibodies is advantageous over the use of non-human antibodies. The in vivo use in humans of non-human antibodies for diagnosis and/or treatment of disease is often hampered by a number of factors. In particular, the human body may recognize non-human antibodies as foreign, which will result in an immunogenic response against the non-human antibodies, resulting in adverse side effects and/or rapid clearance of the antibodies from the circulation. A human antibody diminishes the chance of side-effects when administered to a human individual and often results in a longer half-life in the circulation because of reduced clearance when compared to non-human antibodies. Antibodies or functional parts or functional equivalents thereof according to the invention are further preferably monoclonal antibodies, or functional parts or functional equivalents thereof, more preferably monoclonal human antibodies or functional parts or functional equivalents thereof. A monoclonal antibody is an antibody consisting of a single molecular species, and a titer can be obtained that is significantly higher than that of antibodies present in an antiserum. In addition, monoclonal antibodies can be produced in large quantities by monoclonal antibody-producing cells or recombinant DNA technology.

Table 1 provides an overview of the variable heavy and light chain sequences (also referred to as heavy chain variable region sequences and light chain variable region sequences), as well as the individual CDR sequences, of antibodies AT12-011, AT12-007, AT12-009, AT12-010, AT13-021, AT15-009, AT15-011, AT15-12 and AT15-015. These are preferred antibodies according to the invention, obtained from human patients that have been infected with HCV. AT12-011, AT12-007, AT12-009, AT12-010 and AT13-021 have heavy chain variable region sequences of SEQ ID NOs: 31, 32, 33, 34 and 35 as depicted in Table 1, respectively, and light chain variable region sequences of SEQ ID NOs: 36, 37, 38, 39 and 40 as depicted in Table 1, respectively. AT15-009, AT15-011, AT15-12 and AT15-015 have heavy chain variable region sequences of SEQ ID NOs: 105, 106, 107 and 108 as depicted in Table 1, respectively, and light chain variable region sequences of SEQ ID NOs: 109, 110, 111 and 112 as depicted in Table 1, respectively. The heavy and light chain CDR sequences of these preferred antibodies are also depicted in table 1.

SEQ ID NOs: 1, 6 and 11 are the heavy chain CDR1, CDR2 and CDR3 sequences of AT12-011, respectively. SEQ ID NOs: 16, 21 and 26 are the light chain CDR1, CDR2 and CDR3 sequences of this antibody, respectively.

SEQ ID NOs: 2, 7 and 12 are the heavy chain CDR1, CDR2 and CDR3 sequences of AT12-007, respectively. SEQ ID NOs: 17, 22 and 27 are the light chain CDR1, CDR2 and CDR3 sequences of this antibody, respectively.

SEQ ID NOs: 3, 8 and 13 are the heavy chain CDR1, CDR2 and CDR3 sequences of AT12-009, respectively. SEQ ID NOs: 18, 23 and 28 are the light chain CDR1, CDR2 and CDR3 sequences of this antibody, respectively.

SEQ ID NOs: 4, 9 and 14 are the heavy chain CDR1, CDR2 and CDR3 sequences of AT12-010, respectively. SEQ ID NOs: 19, 24 and 29 are the light chain CDR1, CDR2 and CDR3 sequences of this antibody, respectively.

SEQ ID NOs: 5, 10 and 15 are the heavy chain CDR1, CDR2 and CDR3 sequences of AT13-021, respectively. SEQ ID NOs: 20, 25 and 30 are the light chain CDR1, CDR2 and CDR3 sequences of this antibody, respectively.

SEQ ID NOs: 81, 85 and 89 are the heavy chain CDR1, CDR2 and CDR3 sequences of AT15-009, respectively. SEQ ID NOs: 93, 97 and 101 are the light chain CDR1, CDR2 and CDR3 sequences of this antibody, respectively.

SEQ ID NOs: 82, 86 and 90 are the heavy chain CDR1, CDR2 and CDR3 sequences of AT15-011, respectively. SEQ ID NOs: 94, 98 and 102 are the light chain CDR1, CDR2 and CDR3 sequences of this antibody, respectively.

SEQ ID NOs: 83, 87 and 91 are the heavy chain CDR1, CDR2 and CDR3 sequences of AT15-012, respectively. SEQ ID NOs: 95, 99 and 103 are the light chain CDR1, CDR2 and CDR3 sequences of this antibody, respectively.

SEQ ID NOs: 84, 88 and 92 are the heavy chain CDR1, CDR2 and CDR3 sequences of AT15-015, respectively. SEQ ID NOs: 96, 100 and 104 are the light chain CDR1, CDR2 and CDR3 sequences of this antibody, respectively.

The terms "AT12-011", "AT12-007", "AT12-009", "AT12-010", "AT13-021", "AT15-009", "AT15-011", "AT15-012", and "AT15-015" as used herein encompass all antibodies and functional parts and functional equivalents having at least the heavy chain CDR1, CDR2 and CDR3 regions and the light chain CDR1, CDR2 and CDR3 regions of said antibodies, preferably the heavy chain and light chain variable region sequences of said antibodies, as depicted in Table 1. Non-limiting examples are for instance isolated and/or purified antibodies or recombinantly produced antibodies.

Based on the antibodies of which the CDRs, heavy chain variable region and light chain variable region sequences are depicted in Table 1, it is possible to produce an antibody or functional part or functional equivalent thereof comprising at least one CDR sequence as depicted in Table 1, which is specific for the HCV E2 protein and/or for the HCV E1E2 hetrodimer. Provided is therefore an isolated, recombinant and/or synthetic antibody or a functional part or functional equivalent thereof comprising at least one CDR sequence of an antibody as depicted in Table 1. Preferably, an antibody or functional part or functional equivalent is provided which comprises at least two heavy chain CDRs, more preferably at least three heavy chain CDRs, of the same antibody indicated in Table 1. Hence, preferably at least two or three heavy chain CDRs of antibody AT12-011, AT12-007, AT12-009, AT12-010, AT13-021, AT15-009, AT15-011, AT15-12 or AT15-015 are jointly present in one antibody or functional part or functional equivalent according to the invention. Preferably, an antibody or functional part or functional equivalent according to the invention comprises all three heavy chain CDRs and all three light chain CDRs of the same antibody depicted in Table 1. Optionally, at least one of said CDR sequences is optimized, thereby generating a variant antibody, preferably in order to improve binding affinity, selectivity, neutralizing capacity and/or antibody stability. This is for instance done by mutagenesis procedures where after the stability and/or binding affinity of the resulting antibody or functional part or functional equivalent is preferably tested and an improved antibody variant is preferably selected. As used herein, the term "variant antibody" or "antibody variant" encompasses an antibody, or a functional part or a functional equivalent thereof, that comprises at least one altered, preferably optimized, CDR sequence as compared to any one of the CDR sequences depicted in Table 1. A skilled person is well capable of generating antibody variants according to the invention comprising at least one altered CDR sequence as compared to Table 1. For instance, conservative amino acid substitution is applied. Examples of conservative amino acid substitution include the substitution of one hydrophobic residue such as isoleucine, valine, leucine or methionine for another hydrophobic residue, and the substitution of one polar residue for another polar residue, such as the substitution of arginine for lysine, glutamic acid for aspartic acid, or glutamine for asparagine. Preferably, an antibody or functional part or functional equivalent is provided comprising a CDR sequence which is at least 80% identical to any one of the CDR sequences as depicted in Table 1, so that the HCV E2 binding property or the HCV E1E2 binding property of said CDR sequence is maintained or improved. Preferably, said variant antibody comprises heavy chain and light chain CDR1, CDR2 and CDR3 sequences which are at least 80% identical to the heavy and light chain CDR1, CDR2 and CDR3 sequences of the same antibody as depicted in Table 1.

Besides optimizing CDR sequences in order to improve binding efficacy and/or stability, at least one sequence in at least one of the framework regions can be optimized. This is preferably done in order to improve binding efficacy and/or stability. Framework sequences are for instance optimized by mutating a nucleic acid molecule encoding such framework sequence where after the characteristics of the resulting antibody—or functional part or functional equivalent—are preferably tested. This way, it is possible to obtain improved binding compounds. In a preferred embodiment, human germline sequences are used for framework regions in binding compounds according to the invention. The use of human germline sequences minimizes the risk of immunogenicity of said binding compounds, because these sequences are less likely to contain somatic alterations which are unique to individuals from which the framework regions are derived, and which may cause an immunogenic response when applied to another human individual.

Typically, 1, 2 or 3 amino acid residues of a given CDR sequence may vary while retaining the same kind of binding activity (in kind, not necessarily in amount). Hence, an antibody or functional part or functional equivalent according to the invention preferably contains a heavy chain and light chain CDR1, CDR2 and CDR3 sequence wherein at most 3, preferably at most 2, more preferably at most 1 amino acid of each CDR deviates from the heavy and light chain CDR1, CDR2 and CDR3 sequences from the same antibody, wherein said antibody is selected from the group consisting of AT12-011, AT12-007, AT12-009, AT12-010, AT13-021, AT15-009, AT15-011, AT15-012 and AT15-015.

The invention further provides an isolated, synthetic or recombinant antibody, or a functional part or a functional equivalent thereof comprising:
  a heavy chain CDR1 sequence comprising a sequence which is at least 80% identical to a sequence selected from the group consisting of SEQ ID NOs:1-5 and SEQ ID NOs: 81-84, and/or
  a heavy chain CDR2 sequence comprising a sequence which is at least 80% identical to a sequence selected from the group consisting of SEQ ID NOs:6-10 and SEQ ID NOs: 85-88, and/or
  a heavy chain CDR3 sequence comprising a sequence which is at least 80% identical to a sequence selected from the group consisting of SEQ ID NOs:11-15 and SEQ ID NOs: 89-92, and/or
  a light chain CDR1 sequence comprising a sequence which is at least 80% identical to a sequence selected from the group consisting of SEQ ID NOs:16-20 and SEQ ID NOs:93-96, and/or
  a light chain CDR2 sequence comprising a sequence which is at least 80% identical to a sequence selected from the group consisting of SEQ ID NOs:21-25 and SEQ ID NOs:97-100, and/or a light chain CDR3 sequence comprising a sequence which is at least 80% identical to a sequence selected from the group consisting of SEQ ID NOs:26-30 and SEQ ID NOs: 101-104. Preferably, said antibody or functional part or functional equivalent comprises heavy chain CDR1, CDR2 and/or CDR3 sequences and/or light chain CDR1, CDR2 and/or CDR3 sequences that are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical to these sequences.

An antibody or functional part or functional equivalent according to the invention preferably comprises light chain and heavy chain CDRs having the sequence of:
SEQ ID NO's 1, 6, 11, 16, 21 and 26, or
SEQ ID NO's 2, 7, 12, 17, 22 and 27, or
SEQ ID NO's 3, 8, 13, 18, 23 and 28, or
SEQ ID NO's 4, 9, 14, 19, 24 and 29, or
SEQ ID NO's 5, 10, 15, 20, 25 and 30, or
SEQ ID NOs 81, 85, 89, 93, 97 and 101, or
SEQ ID NOs 82, 86, 90, 94, 98 and 102, or
SEQ ID NOs 83, 87, 91, 95, 99 and 103, or
SEQ ID NOs 84, 88, 92, 96, 100 and 104.

In one embodiment, an antibody or functional part or functional equivalent according to the invention contains at least one sequence modification as compared to at least one of the CDR sequences of AT12-011, AT12-007, AT12-009, AT12-010, AT13-021, AT15-009, AT15-011, AT15-012 or AT15-015. Preferably, said antibody or functional part or functional equivalent according to the invention contains at most three, preferably at most two, sequence modifications as compared to at least one of the CDR sequences of AT12-011, AT12-007, AT12-009, AT12-010, AT13-021, AT15-009, AT15-011, AT15-012 or AT15-015.

Preferably, an antibody according to the invention comprises a heavy chain variable region sequence and/or a light chain variable region sequence as depicted in Table 1, or a sequence which has at least 80% sequence identity thereto. Also provided is therefore an antibody or functional part or functional equivalent thereof according to the invention, having a heavy chain variable region sequence comprising a sequence which is at least 80% identical to a sequence selected from the group consisting of SEQ ID NOs:31-35 and SEQ ID NOs: 105-108 and/or having a light chain variable region sequence which is at least 80% identical to a sequence selected from the group consisting of SEQ ID NOs:36-40 and SEQ ID NOs: 109-112, or sequences that are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical to any one of these heavy chain or light chain variable region sequences. Also provided is an antibody or functional part or functional equivalent thereof according to the invention, that has a heavy chain variable region (VH) sequence that is at least 80% identical to the heavy chain variable region sequence of an antibody selected from the group consisting of AT12-011, AT12-007, AT12-009, AT12-010, AT13-021, AT15-009, AT15-011, AT15-012 and AT15-015, and that has a light chain variable region (VL) sequence that is at least 80% identical to the light chain variable region sequence of the same antibody (selected from the group consisting of AT12-011, AT12-007, AT12-009, AT12-010, AT13-021, AT15-009, AT15-011, AT15-012 and AT15-015), or VH and VL sequences that are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical to the VH and VL sequences, respectively, of any one of said antibodies. The VH and VL sequences of antibodies AT12-011, AT12-007, AT12-009, AT12-010, AT13-021, AT15-009, AT15-011, AT15-012 and AT15-015 are depicted in Table 1.

Typically, sequence variations are well tolerated within the framework regions, whereas the CDR sequences are more critical. Further provided is therefore an antibody or functional part or functional equivalent thereof according to the invention, that has a VH sequence that is at least 80% identical to the VH sequence of an antibody selected from the group consisting of AT12-011, AT12-007, AT12-009, AT12-010, AT13-021, AT15-009, AT15-011, AT15-012 and AT15-015, and that has a VL sequence that is at least 80% identical to the VL sequence of the same antibody (selected from the group consisting of AT12-011, AT12-007, AT12-009, AT12-010, AT13-021, AT15-009, AT15-011, AT15-012 and AT15-015), or VH and VL sequences that are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical to the VH and VL sequences, respectively, of an antibody selected from the group consisting of AT12-011, AT12-007, AT12-009, AT12-010, AT13-021, AT15-009, AT15-011, AT15-012 and AT15-015, wherein said antibody or functional part or functional equivalent comprises heavy chain CDR1, CDR2 and CDR3 sequences and light chain CDR1, CDR2 and CDR3 sequences that differ in at most three, preferably in at most two, preferably in at most one amino acid from the heavy chain and light chain CDR1, CDR2 and CDR3 sequences of an antibody selected from the group consisting of AT12-011, AT12-007, AT12-009, AT12-010, AT13-021, AT15-009, AT15-011, AT15-012 and AT15-015. In some embodiments, an antibody or functional part or functional equivalent according to the invention is provided that has a VH sequence that is at least 80% identical to the VH sequence of an antibody selected from the group consisting of AT12-011, AT12-007, AT12-009, AT12-010, AT13-021, AT15-009, AT15-011, AT15-012 and AT15-015, and that has a VL sequence that is at least 80% identical to the VL sequence of the same antibody (selected from the group consisting of AT12-011, AT12-007, AT12-009, AT12-010, AT13-021, AT15-009, AT15-011, AT15-012 and AT15-015), or VH and VL sequences that are at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical to the VH and VL sequences, respectively, of an antibody selected from the group consisting of AT12-011, AT12-007, AT12-009, AT12-010, AT13-021, AT15-009, AT15-011, AT15-012 and AT15-015, wherein said antibody or functional part or functional equivalent comprises heavy chain CDR1, CDR2 and CDR3 sequences and light chain CDR1, CDR2 and CDR3 sequences that are identical to the heavy chain and light chain CDR1, CDR2 and CDR3 sequences of an antibody selected from the group consisting of AT12-011, AT12-007, AT12-009, AT12-010, AT13-021, AT15-009, AT15-011, AT15-012 and AT15-015. The CDR sequences of these antibodies are depicted in Table 1.

Antibody AT12-011 is a preferred antibody of the invention. As shown in the Examples, antibody AT12-011 is able to bind to protein E1E2 of all tested HCV genotypes, i.e. it is able to bind at least HCV genotypes 1a, 1b, 2b, 3, 4, 5 and 6. AT12-011 is further preferred because it binds to a conformational (e.g. discontinuous or non-linear) epitope in the E2 protein. Conformational epitopes are generally conserved, which indicates that AT12-011 offers broad therapeutic application for ameliorating or preventing HCV infection. As demonstrated in the Examples, AT12-011 does not bind to denatured E1E2. It is further demonstrated that AT12-011 specifically binds a novel epitope in the E2 protein. This epitope is characterized by the fact that it does not comprise amino acids corresponding to amino acids L413, N415, G418, W420, N423, 5424, T435, G436, A439, L441, F442, Y443, N448, Y485, T526, Y527, W529, G530, N532, D533, T534, D535, V538, P612, W616, R657, P664, P676 and D698 of the H77 E2 amino acid sequence as depicted in FIG. 1. Therefore, AT12-011 can be advantageously combined with an antibody specific for a conformational epitope of the E2 protein that comprises at least one amino acid corresponding to the amino acids 424-443 and 523-540, preferably corresponding to amino acids F442, Y527, W529, G530 and D535, of the H77 E2 protein. A preferred combination is that of AT12-011 and an antibody selected from the group consisting of AT12-007, AT12-009, AT12-010, AT13-021, AT15-009, AT15-011, AT15-012, AT15-015, CBH2, HC11, HC1, AR3A, AR3B, AR3C, AR3D, A8, 1:7, e20 and e137, preferably selected from the group consisting of AT12-007, AT12-009, AT12-010, AT13-021, AT15-009, AT15-011, AT15-012 and AT15-015. Interesting advantages of such combinations are the reduced amount of each antibody needed and the achievement of a more potent HCV treatment because different epitopes of the E2 protein are targeted with the same treatment. Antibody AT12-011 is further preferred because it has a particularly high affinity for the E2 protein. As demonstrated in the examples, AT12-011 has a $K_D$ of 0.3 nM for the E2 protein of HCV genotype 1a and a $K_D$ of 0.2 nM for the E2 protein of HCV genotype 2b under the SPR experimental conditions of Example 1, whereas AT12-011 even has a $K_D$ of 0.015 nM for the E2 protein of HCV genotype 1a under the SPR experimental conditions of Example 2. Furthermore, AT12-011 is a preferred antibody because it is capable of neutralizing HCV genotypes 1a and 1b with a particularly high neutralizing activity as shown in the Examples. Antibody AT12-011 is further preferred because it potently inhibits binding of the HCV E1E2 protein to CD81; binding is essentially blocked already at a concentration of 1 µg/ml antibody in a method as described in the Examples. Provided is therefore an isolated, synthetic or recombinant antibody or functional part or functional equivalent thereof comprising a heavy chain CDR1 having the sequence of SEQ ID NO:1, a heavy chain CDR2 having the sequence of SEQ ID NO:6, a heavy chain CDR3 having the sequence of SEQ ID NO:11, a light chain CDR1 having the sequence of SEQ ID NO:16, a light chain CDR2 having the sequence of SEQ ID NO:21 and a light chain CDR3 having the sequence of SEQ ID NO:26. Said antibody or functional part or functional equivalent preferably specifically binds to a conformational epitope of HCV protein E2 which epitope does not comprise amino acids corresponding to amino acids L413, N415, G418, W420, N423, 5424, T435, G436, A439, L441, F442, Y443, N448, Y485, T526, Y527, W529, G530, N532, D533, T534, D535, V538, P612, W616, R657, P664, P676 and D698 of the H77 E2 amino acid sequence as depicted in FIG. 1. Said antibody or functional part or functional equivalent further preferably has HCVpp neutralizing activity in vitro. Also provided are antibodies and functional parts and functional equivalents thereof comprising heavy chain CDR1, CDR2 and CDR3 and light chain CDR1, CDR2 and CDR3 that have at least 80%, preferably at least 85%, more preferably at least 90%, more preferably at least 95%, more preferably at least 96%, more preferably at least 97%, more preferably at least 98%, more preferably at least 99% sequence identity with the sequences of SEQ ID NO's: 1, 6, 11, 16, 21 and 26. Also provided are antibodies and functional parts and functional equivalents thereof comprising heavy chain CDR1, CDR2 and CDR3 sequences and light chain CDR1, CDR2 and CDR3 sequences that differ in at most three, preferably in at most two, more preferably in at most one amino acid from the heavy chain CDR1, CDR2 and CDR3 sequences and the light chain CDR1, CDR2 and CDR3 sequences of antibody AT12-011. An antibody or functional part or functional equivalent according to the invention preferably has the entire heavy chain variable region and light chain variable region sequences of antibody AT12-011, comprising the sequence of SEQ ID NO:31 and SEQ ID NO:36. Also provided are antibodies and functional parts and functional equivalents thereof comprising a heavy chain variable region and a light chain variable region that have at least 80%, preferably at least 85%, more preferably at least 90%, more preferably at least 95%, more preferably at least 96%, more preferably at least 97%, more preferably at least 98%, more preferably at least 99% sequence identity with the sequences of SEQ ID NO's: 31 and 36, respectively. An isolated, synthetic or recombinant antibody or functional part or functional equivalent thereof that competes with antibody AT12-011 for binding to HCV protein E2 is also herewith provided.

Another preferred antibody is AT12-007. As shown in the Examples, antibody AT12-007 is able to bind to protein E1E2 of all tested HCV genotypes, i.e. it is able to bind at least HCV genotypes 1a, 1b, 2b, 3, 4, 5 and 6. AT12-007 is further preferred because it binds to a conformational epitope in the E2 protein. Conformational epitopes are generally conserved, which indicates that AT12-007 offers broad therapeutic application for ameliorating or preventing HCV infection. As demonstrated in the Examples, AT12-007 does not bind to denatured E1E2. It is further demonstrated that AT12-007 specifically binds an epitope in the H77 E2 protein comprising amino acids L441, F442, Y443, Y527, W529, G530, D535 and W616, more in particular amino acids S424, G436, L441, F442, Y443, T526, Y527, W529, G530, D535 and W616. AT12-007 can be advantageously combined with antibodies that specifically bind to an epitope of hepatitis C virus (HCV) protein E2 which epitope does not comprise amino acids corresponding to amino acids S424, G436, L441, F442, Y485, T526, Y527, W529, G530, D535 and W616 of the H77 E2 amino acid sequence, such as for instance antibody AT12-011, AT15-011 and/or AT15-

015. Advantages of such combinations are the reduced amount of each antibody needed and the achievement of a more potent HCV treatment because different epitopes of the E2 protein are targeted with the same treatment. Antibody AT12-007 is further preferred because it has a particularly high affinity for the E2 protein. As demonstrated in the examples, AT12-007 has a $K_D$ of 44 nM for the E2 protein of HCV genotype 1a and a $K_D$ of 3.8 nM for the E2 protein of HCV genotype 2b under the SPR experimental conditions of Example 1. Furthermore, AT12-007 is a preferred antibody because it is capable of neutralizing HCV genotypes 1a, 1b, 2b, 3a and 4a with a high neutralizing activity as shown in the Examples. Antibody AT12-007 is further preferred because it potently inhibits binding of the HCV E1E2 protein to CD81; binding is essentially blocked at a concentration of 100 μg/ml antibody in a method as described in the Examples. Provided is therefore an isolated, synthetic or recombinant antibody or functional part or functional equivalent thereof comprising a heavy chain CDR1 having the sequence of SEQ ID NO:2, a heavy chain CDR2 having the sequence of SEQ ID NO:7, a heavy chain CDR3 having the sequence of SEQ ID NO:12, a light chain CDR1 having the sequence of SEQ ID NO:17, a light chain CDR2 having the sequence of SEQ ID NO:22 and a light chain CDR3 having the sequence of SEQ ID NO:27. Said antibody or functional part or functional equivalent preferably specifically binds to a conformational epitope of HCV protein E2 comprising amino acids corresponding to amino acids F442, Y527, W529, G530, D535 and W616 of the H77 E2 amino acid sequence as depicted in FIG. 1, more in particular amino acids S424, G436, L441, F442, Y443, T526, Y527, W529, G530, D535 and W616, and/or has HCVpp neutralizing activity in vitro. Also provided are antibodies and functional parts and functional equivalents comprising heavy chain CDR1, CDR2 and CDR3 sequences and light chain CDR1, CDR2 and CDR3 sequences that have at least 80%, preferably at least 85%, more preferably at least 90%, more preferably at least 95%, more preferably at least 96%, more preferably at least 97%, more preferably at least 98%, more preferably at least 99% sequence identity with the sequences of SEQ ID NOs: 2, 7, 12, 17, 22 and 27. Also provided are antibodies and functional parts and functional equivalents thereof comprising heavy chain CDR1, CDR2 and CDR3 sequences and light chain CDR1, CDR2 and CDR3 sequences that differ in at most three, preferably in at most two, more preferably in at most one amino acid from the heavy chain CDR1, CDR2 and CDR3 sequences and the light chain CDR1, CDR2 and CDR3 sequences of antibody AT12-007. An antibody or functional part or functional equivalent according to the invention preferably has the entire heavy chain variable region and light chain variable region sequences of antibody AT12-007, comprising the sequences of SEQ ID NO:32 and SEQ ID NO:37. Also provided are antibodies and functional parts and functional equivalents thereof comprising a heavy chain variable region and a light chain variable region that have at least 80%, preferably at least 85%, more preferably at least 90%, more preferably at least 95%, more preferably at least 96%, more preferably at least 97%, more preferably at least 98%, more preferably at least 99% sequence identity with the sequences of SEQ ID NO's: 32 and 37, respectively. An isolated, synthetic or recombinant antibody or functional part or functional equivalent thereof that competes with antibody AT12-007 for binding to HCV protein E2 is also herewith provided.

Another preferred antibody is AT12-009. As shown in the Examples, antibody AT12-009 is able to bind to protein E1E2 of all tested HCV genotypes, i.e. it is able to bind at least HCV genotypes 1a, 1b, 2b, 3, 4, 5 and 6. AT12-009 is further preferred because it binds to a conformational epitope in the E2 protein. Conformational epitopes are generally conserved, which indicates that AT12-009 offers broad therapeutic application for ameliorating or preventing HCV infection. As demonstrated in the Examples, AT12-009 does not bind to denatured E1E2. It is further demonstrated that AT12-009 specifically binds an epitope in the H77 E2 protein comprising amino acids F442, Y527, W529, G530, D535 and W616, more in particular amino acids S424, G436, L441, F442, T526, Y527, W529, G530, D535 and W616. AT12-009 can be advantageously combined with antibodies that specifically bind to an epitope of hepatitis C virus (HCV) protein E2 which epitope does not comprise amino acids corresponding to amino acids S424, G436, L441, F442, T526, Y527, W529, G530, D535 and W616 of the H77 E2 amino acid sequence as depicted in FIG. 1, such as for instance antibody AT12-011, AT15-011 and/or AT15-015. Possible advantages of such combinations are the reduced amount of each antibody needed and the achievement of a more potent HCV treatment because different epitopes of the E2 protein are targeted with the same treatment. Antibody AT12-009 is further preferred because it has a particularly high affinity for the E2 protein. As demonstrated in the examples, AT12-009 has a $K_D$ of 1.3 nM for the E2 protein of HCV genotype 1a and a $K_D$ of 2.3 nM for the E2 protein of HCV genotype 2b under the SPR experimental conditions of Example 1, whereas AT12-009 even has a $K_D$ of 0.05 nM for the E2 protein of HCV genotype 1a under the SPR experimental conditions of Example 2. Furthermore, AT12-009 is a preferred antibody because it is capable of neutralizing HCV genotypes 1a, 2b, 3a, 4a and 4d with a high neutralizing activity as shown in the Examples. Antibody AT12-009 is further preferred because it potently inhibits binding of the HCV E1E2 protein to CD81; binding is essentially blocked already at a concentration of 1 μg/ml antibody in a method as described in the Examples. Provided is therefore an isolated, synthetic or recombinant antibody or functional part or functional equivalent thereof comprising a heavy chain CDR1 having the sequence of SEQ ID NO:3, a heavy chain CDR2 having the sequence of SEQ ID NO:8, a heavy chain CDR3 having the sequence of SEQ ID NO:13, a light chain CDR1 having the sequence of SEQ ID NO:18, a light chain CDR2 having the sequence of SEQ ID NO:23 and a light chain CDR3 having the sequence of SEQ ID NO:28. Said antibody or functional part or functional equivalent preferably specifically binds to a conformational epitope of HCV protein E2 comprising amino acids corresponding to amino acids F442, Y527, W529, G530, D535 and W616 of the H77 E2 amino acid sequence as depicted in FIG. 1, more in particular amino acids S424, G436, L441, F442, T526, Y527, W529, G530, D535 and W616, and/or has HCVpp neutralizing activity in vitro. Also provided are antibodies and functional parts and functional equivalents thereof comprising heavy chain CDR1, CDR2 and CDR3 sequences and light chain CDR1, CDR2 and CDR3 sequences that have at least 80%, preferably at least 85%, more preferably at least 90%, more preferably at least 95%, more preferably at least 96%, more preferably at least 97%, more preferably at least 98%, more preferably at least 99% sequence identity with the sequences of SEQ ID NOs: 3, 8, 13, 18, 23 and 28. Also provided are antibodies and functional parts and functional equivalents thereof comprising heavy chain CDR1, CDR2 and CDR3 sequences and light chain CDR1, CDR2 and CDR3 sequences that differ in at most three, preferably in at most two, more preferably in at most one amino acid from the heavy chain CDR1, CDR2 and CDR3 sequences and the light chain CDR1, CDR2 and CDR3 sequences of antibody AT12-009. Said antibody or functional part or functional equivalent thereof preferably has the entire heavy chain variable region and light chain variable region sequences of antibody AT12-009, comprising the sequence of SEQ ID NO:33 and SEQ ID NO:38, respectively. Also provided are antibodies and functional parts and functional equivalents thereof comprising a heavy chain variable region and a light chain variable region that have at least 80%, preferably at least 85%, more preferably at least 90%, more preferably at least 95%, more preferably at least 96%, more preferably at least 97%, more preferably at least 98%, more preferably at least 99% sequence identity to the sequences of SEQ ID NO's: 33 and 38, respectively. An isolated, synthetic or recombinant antibody or functional part or functional equivalent thereof that competes with antibody AT12-009 for binding to HCV protein E2 is also herewith provided.

Another preferred antibody is AT12-010. As shown in the Examples, antibody AT12-010 is able to bind to protein E1E2 of all tested HCV genotypes, i.e. it is able to bind at least HCV genotypes 1a, 1b, 2b, 3, 4, 5 and 6. AT12-010 is further preferred because it binds to a conformational epitope in the E2 protein. Conformational epitopes are generally conserved, which indicates that AT12-010 offers broad therapeutic application for ameliorating or preventing HCV infection. As demonstrated in the Examples, AT12-010 does not bind to denatured E1E2. It is further demonstrated that AT12-010 specifically binds an epitope in the H77 E2 protein comprising amino acids W420, F442, Y527, W529, G530, D535 and W616, more in particular amino acids W420, 5424, T435, G436, L441, F442, Y443, T526, Y527, W529, G530, D535 and W616. AT12-010 can be advantageously combined with antibodies that specifically bind to an epitope of hepatitis C virus (HCV) protein E2 which epitope does not comprise amino acids corresponding to amino acids W420, 5424, T435, G436, L441, F442, Y443, T526, Y527, W529, G530, D535 and W616 of the H77 E2 amino acid sequence, such as for instance antibody AT12-011, AT15-011 and/or AT15-015. Advantages of such combinations are the reduced amount of each antibody needed and the achievement of a more potent HCV treatment because different epitopes of the E2 protein are targeted with the same treatment. Antibody AT12-010 is further preferred because it has a particularly high affinity for the E2 protein. As demonstrated in the examples, AT12-010 has a $K_D$ of 39.3 nM for the E2 protein of HCV genotype 1a and a $K_D$ of 22.8 nM for the E2 protein of HCV genotype 2b under the SPR experimental conditions of Example 1. Furthermore, AT12-010 is a preferred antibody because it is capable of neutralizing HCV genotypes 1a, 1b, 2b and 3a with a high neutralizing activity as shown in the Examples. Antibody AT12-010 is further preferred because it potently inhibits binding of the HCV E1E2 protein to CD81; binding is essentially blocked at a concentration of 100 µg/ml antibody in a method as described in the Examples. Provided is therefore an isolated, synthetic or recombinant antibody or functional part or functional equivalent thereof comprising a heavy chain CDR1 having the sequence of SEQ ID NO:4, a heavy chain CDR2 having the sequence of SEQ ID NO:9, a heavy chain CDR3 having the sequence of SEQ ID NO:14, a light chain CDR1 having the sequence of SEQ ID NO:19, a light chain CDR2 having the sequence of SEQ ID NO:24 and a light chain CDR3 having the sequence of SEQ ID NO:29. Said antibody or functional part or functional equivalent preferably specifically binds to a conformational epitope of HCV protein E2 comprising amino acids corresponding to amino acids W420, F442, Y527, W529, G530, D535 and W616 of the H77 E2 amino acid sequence as depicted in FIG. 1, more in particular amino acids W420, 5424, T435, G436, L441, F442, Y443, T526, Y527, W529, G530, D535 and W616, and/or has HCVpp neutralizing activity in vitro. Also provided are antibodies and functional parts and functional equivalents thereof comprising heavy chain CDR1, CDR2 and CDR3 sequences and light chain CDR1, CDR2 and CDR3 sequences that have at least 80%, preferably at least 85%, more preferably at least 90%, more preferably at least 95%, more preferably at least 96%, more preferably at least 97%, more preferably at least 98%, more preferably at least 99% sequence identity to the sequences of SEQ ID NO's: 4, 9, 14, 19, 24 and 29. Also provided are antibodies and functional parts and functional equivalents thereof comprising heavy chain CDR1, CDR2 and CDR3 sequences and light chain CDR1, CDR2 and CDR3 sequences that differ in at most three, preferably in at most two, more preferably in at most one amino acid from the heavy chain CDR1, CDR2 and CDR3 sequences and the light chain CDR1, CDR2 and CDR3 sequences of antibody AT12-010. Also provided are antibodies and functional parts and functional equivalents thereof comprising heavy chain CDR1, CDR2 and CDR3 sequences and light chain CDR1, CDR2 and CDR3 sequences that differ in at most three, preferably in at most two, more preferably in at most one amino acid from the heavy chain CDR1, CDR2 and CDR3 sequences and the light chain CDR1, CDR2 and CDR3 sequences of antibody AT12-011. An antibody or functional part or functional equivalent according to the invention preferably has the entire heavy chain variable region and light chain variable region sequences of antibody AT12-010, comprising the sequences of SEQ ID NO:34 and SEQ ID NO:39, respectively. Also provided are antibodies comprising a heavy chain variable region and a light chain variable region that have at least 80%, preferably at least 85%, more preferably at least 90%, more preferably at least 95%, more preferably at least 96%, more preferably at least 97%, more preferably at least 98%, more preferably at least 99% sequence identity to the sequences of SEQ ID NO's: 34 and 39, respectively. An isolated, synthetic or recombinant antibody or functional part or functional equivalent thereof that competes with antibody AT12-010 for binding to HCV protein E2 is also herewith provided.

Another preferred antibody is AT13-021. As shown in the Examples, antibody AT13-021 is able to bind to protein E1E2 of all tested HCV genotypes, i.e. it is able to bind at least HCV genotypes 1a, 1b, 2b, 3, 4, 5 and 6. AT13-021 is further preferred because it binds to a conformational epitope in the E2 protein. Conformational epitopes are generally conserved, which indicates that AT13-021 offers broad therapeutic application for ameliorating or preventing HCV infection. As demonstrated in the Examples, AT13-021 does not bind to denatured E1E2. It is further demonstrated that AT13-021 specifically binds an epitope in the H77 E2 protein comprising amino acids F442, Y527, W529, G530, D535 and W616, more in particular amino acids S424, T435, G436, L441, F442, T526, Y527, W529, G530, D535 and W616. AT13-021 can be advantageously combined with antibodies that specifically bind to an epitope of hepatitis C virus (HCV) protein E2 which epitope does not comprise amino acids corresponding to amino acids S424, T435, G436, L441, F442, T526, Y527, W529, G530, D535 and W616 of the H77 E2 amino acid sequence, such as for instance antibody AT12-011, AT15-011, and/or AT15-015. Possible advantages of such combinations are the reduced amount of each antibody needed and the achievement of a more potent HCV treatment because different epitopes of the E2 protein are targeted with the same treatment. Antibody AT13-021 is further preferred because it has a particularly high affinity for the E2 protein. As demonstrated in the examples, AT13-021 has a $K_D$ of 14.2 nM for the E2 protein of HCV genotype 1a and a $K_D$ of 2.0 nM for the E2 protein of HCV genotype 2b under the SPR experimental conditions of Example 1. Furthermore, AT13-021 is a preferred antibody because it is capable of neutralizing HCV genotypes 1a, 1b, 2b, 3a, 4a and 4d with a high neutralizing activity as shown in the Examples. Antibody AT13-021 is further preferred because it potently inhibits binding of the HCV E1E2 protein to CD81; binding is essentially blocked at a concentration of 50 μg/ml antibody in a method as described in the Examples. Provided is therefore an isolated, synthetic or recombinant antibody or functional part or functional equivalent thereof comprising a heavy chain CDR1 having the sequence of SEQ ID NO:5, a heavy chain CDR2 having the sequence of SEQ ID NO:10, a heavy chain CDR3 having the sequence of SEQ ID NO:15, a light chain CDR1 having the sequence of SEQ ID NO:20, a light chain CDR2 having the sequence of SEQ ID NO:25 and a light chain CDR3 having the sequence of SEQ ID NO:30. Said antibody or functional part or functional equivalent preferably specifically binds to a conformational epitope of HCV protein E2 comprising amino acids corresponding to amino acids F442, Y527, W529, G530, D535 and W616 of the H77 E2 amino acid sequence as depicted in FIG. 1, more in particular amino acids S424, T435, G436, L441, F442, T526, Y527, W529, G530, D535 and W616, and/or has HCVpp neutralizing activity in vitro. Also provided are antibodies and functional parts and functional equivalents thereof comprising heavy chain CDR1, CDR2 and CDR3 sequences and light chain CDR1, CDR2 and CDR3 sequences that have at least 80%, preferably at least 85%, more preferably at least 90%, more preferably at least 95%, more preferably at least 96%, more preferably at least 97%, more preferably at least 98%, more preferably at least 99% sequence identity with the sequences of SEQ ID NOs: 5, 10, 15, 20, 25 and 30. Also provided are antibodies and functional parts and functional equivalents thereof comprising heavy chain CDR1, CDR2 and CDR3 sequences and light chain CDR1, CDR2 and CDR3 sequences that differ in at most three, preferably in at most two, more preferably in at most one amino acid from the heavy chain CDR1, CDR2 and CDR3 sequences and the light chain CDR1, CDR2 and CDR3 sequences of antibody AT13-021. An antibody or functional part or functional equivalent according to the invention preferably has the entire heavy chain variable region and light chain variable region sequences of antibody AT13-021, comprising the sequences of SEQ ID NO:35 and SEQ ID NO:40, respectively. Also provided are antibodies and functional parts and functional equivalents thereof comprising a heavy chain variable region and a light chain variable region that have at least 80%, preferably at least 85%, more preferably at least 90%, more preferably at least 95%, more preferably at least 96%, more preferably at least 97%, more preferably at least 98%, more preferably at least 99% sequence identity to the sequences of SEQ ID NO's: 35 and 40, respectively. An isolated, synthetic or recombinant antibody or functional part or functional equivalent thereof that competes with antibody AT13-021 for binding to HCV protein E2 is also herewith provided.

Another preferred antibody is AT15-009. As shown in the Examples, antibody AT15-009 is able to bind to protein E1E2 of many HCV genotypes, i.e. it is able to bind at least HCV genotypes 1a, 3a, 4a, 4d, 5 and 6. AT15-009 is further preferred because it binds to a conformational epitope in the E2 protein. Conformational epitopes are generally conserved, which indicates that AT15-009 offers broad therapeutic application for ameliorating or preventing HCV infection. As demonstrated in the Examples, AT15-009 does not bind to denatured E1E2. It is further demonstrated that AT15-009 specifically binds an epitope in the H77 E2 protein comprising amino acids F442 and W616. AT15-009 can be advantageously combined with antibodies that specifically bind to an epitope of hepatitis C virus (HCV) protein E2 which epitope does not comprise amino acids corresponding to amino acids F442 and W616 of the H77 E2 amino acid sequence, such as for instance antibody AT12-011, AT15-011, AT15-012 and/or AT15-015. Advantages of such combinations are the reduced amount of each antibody needed and the achievement of a more potent HCV treatment because different epitopes of the E2 protein are targeted with the same treatment. Antibody AT15-009 is further preferred because it has a particularly high affinity for the E2 protein. As demonstrated in the examples, AT15-009 has a $K_D$ of 0.242 nM for the E2 protein of HCV genotype 1a under the SPR experimental conditions of Example 2. Furthermore, AT15-009 is a preferred antibody because it is capable of neutralizing HCV genotypes 1a, 3a, 4a and 4d with a high neutralizing activity as shown in the Examples. Provided is therefore an isolated, synthetic or recombinant antibody or functional part or functional equivalent thereof comprising a heavy chain CDR1 having the sequence of SEQ ID NO:81, a heavy chain CDR2 having the sequence of SEQ ID NO:85, a heavy chain CDR3 having the sequence of SEQ ID NO:89, a light chain CDR1 having the sequence of SEQ ID NO:93, a light chain CDR2 having the sequence of SEQ ID NO:97 and a light chain CDR3 having the sequence of SEQ ID NO:101. Said antibody or functional part or functional equivalent preferably specifically binds to a conformational epitope of HCV protein E2 comprising amino acids corresponding to amino acids F442 and W616 of the H77 E2 amino acid sequence as depicted in FIG. 1, and/or has HCVpp neutralizing activity in vitro. Also provided are antibodies and functional parts and functional equivalents comprising heavy chain CDR1, CDR2 and CDR3 sequences and light chain CDR1, CDR2 and CDR3 sequences that have at least 80%, preferably at least 85%, more preferably at least 90%, more preferably at least 95%, more preferably at least 96%, more preferably at least 97%, more preferably at least 98%, more preferably at least 99% sequence identity with the sequences of SEQ ID NOs: 81, 85, 89, 93, 97 and 101. Also provided are antibodies and functional parts and functional equivalents thereof comprising heavy chain CDR1, CDR2 and CDR3 sequences and light chain CDR1, CDR2 and CDR3 sequences that differ in at most three, preferably in at most two, more preferably in at most one amino acid from the heavy chain CDR1, CDR2 and CDR3 sequences and the light chain CDR1, CDR2 and CDR3 sequences of antibody AT15-009. An antibody or functional part or functional equivalent according to the invention preferably has the entire heavy chain variable region and light chain variable region sequences of antibody AT15-009, comprising the sequences of SEQ ID NO:105 and SEQ ID NO:109. Also provided are antibodies and functional parts and functional equivalents thereof comprising a heavy chain variable region and a light chain variable region that have at least 80%, preferably at least 85%, more preferably at least 90%, more preferably at least 95%, more preferably at least 96%, more preferably at least 97%, more preferably at least 98%, more preferably at least 99% sequence identity with the sequences of SEQ ID NOs: 105 and 109, respectively. An isolated, synthetic or recombinant antibody or functional part or functional equivalent thereof that competes with antibody AT15-009 for binding to HCV protein E2 is also herewith provided.

Another preferred antibody is AT15-011. As shown in the Examples, antibody AT15-011 is able to bind to protein E1E2 of many HCV genotypes, i.e. it is able to bind at least HCV genotypes 1a, 3a, 4a, 4d and 5. AT15-011 is further preferred because it binds to a conformational epitope in the E1E2 heterodimer. Conformational epitopes are generally conserved, which indicates that AT15-011 offers broad therapeutic application for ameliorating or preventing HCV infection. As demonstrated in the Examples, AT15-011 does not bind to denatured E1E2. It is further demonstrated that AT15-011 specifically binds an epitope in the H77 E1E2 heterodimer comprising amino acids R657 and D698 of E2. AT15-011 can be advantageously combined with antibodies that specifically bind to an epitope of hepatitis C virus (HCV) protein E2 which epitope does not comprise amino acids corresponding to amino acids R657 and D698 of the H77 E2 amino acid sequence. A preferred combination is that of AT15-011 and an antibody selected from the group consisting of AT12-011, AT12-007, AT12-009, AT12-010, AT13-021, AT15-009, AT15-012, CBH2, HC11, HC1, AR3A, AR3B, AR3C, AR3D, A8, 1:7, e20 and e137, preferably selected from the group consisting of AT12-011, AT12-007, AT12-009, AT12-010, AT13-021, AT15-009 and AT15-012. Advantages of such combinations are the reduced amount of each antibody needed and the achievement of a more potent HCV treatment because different epitopes of the E2 protein are targeted with the same treatment. Antibody AT15-011 is further preferred because it is capable of neutralizing HCV genotypes 1a and 3a with a high neutralizing activity as shown in Example 2. Provided is therefore an isolated, synthetic or recombinant antibody or functional part or functional equivalent thereof comprising a heavy chain CDR1 having the sequence of SEQ ID NO:82, a heavy chain CDR2 having the sequence of SEQ ID NO:86, a heavy chain CDR3 having the sequence of SEQ ID NO:90, a light chain CDR1 having the sequence of SEQ ID NO:94, a light chain CDR2 having the sequence of SEQ ID NO:98 and a light chain CDR3 having the sequence of SEQ ID NO:102. Said antibody or functional part or functional equivalent preferably specifically binds to a conformational epitope of a HCV E1E2 heterodimer comprising amino acids corresponding to amino acids R657 and D698 of the H77 E2 amino acid sequence as depicted in FIG. 1, and/or has HCVpp neutralizing activity in vitro. Also provided are antibodies and functional parts and functional equivalents comprising heavy chain CDR1, CDR2 and CDR3 sequences and light chain CDR1, CDR2 and CDR3 sequences that have at least 80%, preferably at least 85%, more preferably at least 90%, more preferably at least 95%, more preferably at least 96%, more preferably at least 97%, more preferably at least 98%, more preferably at least 99% sequence identity with the sequences of SEQ ID NOs: 82, 86, 90, 94, 98 and 102. Also provided are antibodies and functional parts and functional equivalents thereof comprising heavy chain CDR1, CDR2 and CDR3 sequences and light chain CDR1, CDR2 and CDR3 sequences that differ in at most three, preferably in at most two, more preferably in at most one amino acid from the heavy chain CDR1, CDR2 and CDR3 sequences and the light chain CDR1, CDR2 and CDR3 sequences of antibody AT15-011. An antibody or functional part or functional equivalent according to the invention preferably has the entire heavy chain variable region and light chain variable region sequences of antibody AT15-011, comprising the sequences of SEQ ID NO:106 and SEQ ID NO:110. Also provided are antibodies and functional parts and functional equivalents thereof comprising a heavy chain variable region and a light chain variable region that have at least 80%, preferably at least 85%, more preferably at least 90%, more preferably at least 95%, more preferably at least 96%, more preferably at least 97%, more preferably at least 98%, more preferably at least 99% sequence identity with the sequences of SEQ ID NO's: 106 and 110, respectively. An isolated, synthetic or recombinant antibody or functional part or functional equivalent thereof that competes with antibody AT15-011 for binding to a HCV E1E2 protein is also herewith provided.

Another preferred antibody is AT15-015. As shown in the Examples, antibody AT15-015 is able to bind to protein E1E2 of many HCV genotypes, i.e. it is able to bind at least HCV genotypes 1a, 3a, 4a, 4d and 5. AT15-015 is further preferred because it binds to a conformational epitope in the E1E2 protein. Conformational epitopes are generally conserved, which indicates that AT15-015 offers broad therapeutic application for ameliorating or preventing HCV infection. As demonstrated in the Examples, AT15-015 does not bind to denatured E1E2. It is further demonstrated that AT15-015 specifically binds an epitope in the H77 E1E2 protein comprising amino acids R657 and D698. AT15-015 can be advantageously combined with antibodies that specifically bind to an epitope of hepatitis C virus (HCV) protein E2 which epitope does not comprise amino acids corresponding to amino acids R657 and D698 of the H77 E2 amino acid sequence. A preferred combination is that of AT15-015 and an antibody selected from the group consisting of AT12-011, AT12-007, AT12-009, AT12-010, AT13-021, AT15-009, AT15-012, CBH2, HC11, HC1, AR3A, AR3B, AR3C, AR3D, A8, 1:7, e20 and e137, preferably selected from the group consisting of AT12-011, AT12-007, AT12-009, AT12-010, AT13-021, AT15-009 and AT15-012. Advantages of such combinations are the reduced amount of each antibody needed and the achievement of a more potent HCV treatment because different epitopes of the E2 protein are targeted with the same treatment. Antibody AT15-015 is further preferred because it is capable of neutralizing HCV genotypes 1a and 3a with a high neutralizing activity as shown in Example 2. Provided is therefore an isolated, synthetic or recombinant antibody or functional part or functional equivalent thereof comprising a heavy chain CDR1 having the sequence of SEQ ID NO:84, a heavy chain CDR2 having the sequence of SEQ ID NO:88, a heavy chain CDR3 having the sequence of SEQ ID NO:92, a light chain CDR1 having the sequence of SEQ ID NO:96, a light chain CDR2 having the sequence of SEQ ID NO:100 and a light chain CDR3 having the sequence of SEQ ID NO:104. Said antibody or functional part or functional equivalent preferably specifically binds to a conformational epitope of a HCV E1E2 protein comprising amino acids corresponding to amino acids R657 and D698 of the H77 E2 amino acid sequence as depicted in FIG. 1, and/or has HCVpp neutralizing activity in vitro. Also provided are antibodies and functional parts and functional equivalents comprising heavy chain CDR1, CDR2 and CDR3 sequences and light chain CDR1, CDR2 and CDR3 sequences that have at least 80%, preferably at least 85%, more preferably at least 90%, more preferably at least 95%, more preferably at least 96%, more preferably at least 97%, more preferably at least 98%, more preferably at least 99% sequence identity with the sequences of SEQ ID NOs: 84, 88, 92, 96, 100 and 104. Also provided are antibodies and functional parts and functional equivalents thereof comprising heavy chain CDR1, CDR2 and CDR3 sequences and light chain CDR1, CDR2 and CDR3 sequences that differ in at most three, preferably in at most two, more preferably in at most one amino acid from the heavy chain CDR1, CDR2 and CDR3 sequences and the light chain CDR1, CDR2 and CDR3 sequences of antibody AT15-015. An antibody or functional part or functional equivalent according to the invention preferably has the entire heavy chain variable region and light chain variable region sequences of antibody AT15-015, comprising the sequences of SEQ ID NO:108 and SEQ ID NO:112. Also provided are antibodies and functional parts and functional equivalents thereof comprising a heavy chain variable region and a light chain variable region that have at least 80%, preferably at least 85%, more preferably at least 90%, more preferably at least 95%, more preferably at least 96%, more preferably at least 97%, more preferably at least 98%, more preferably at least 99% sequence identity with the sequences of SEQ ID NOs: 108 and 112, respectively. An isolated, synthetic or recombinant antibody or functional part or functional equivalent thereof that competes with antibody AT15-015 for binding to a HCV E1E2 heterodimer is also herewith provided.

Another preferred antibody is AT15-012. As shown in the Examples, antibody AT15-012 is able to bind to protein E1E2 of all tested HCV genotypes, i.e. it is able to bind at least HCV genotypes 1a, 2b, 3a, 4a, 4d, 5 and 6. AT15-012 is further preferred because it binds to a conformational epitope in the E2 protein. Conformational epitopes are generally conserved, which indicates that AT15-012 offers broad therapeutic application for ameliorating or preventing HCV infection. As demonstrated in the Examples, AT15-012 does not bind to denatured E1E2. It is further demonstrated that AT15-012 specifically binds an epitope in the H77 E2 protein comprising at least amino acid G530. AT15-012 can be advantageously combined with antibodies that specifically bind to another epitope of HCV protein E2 or E1E2, such as for instance antibody AT12-011, AT15-011, AT15-015 and AT15-009. Advantages of such combinations are the reduced amount of each antibody needed and the achievement of a more potent HCV treatment because different epitopes of the E2 protein are targeted with the same treatment. Antibody AT15-012 is further preferred because it has a particularly high affinity for the E2 protein. As demonstrated in the examples, AT15-012 has a $K_D$ of 0.015 nM for the E2 protein of HCV genotype 1a under the SPR experimental conditions of Example 2. Furthermore, AT15-012 is a preferred antibody because it is capable of neutralizing HCV genotypes 1a, 3a, 4a and 4d with a high neutralizing activity as shown in the Examples. Provided is therefore an isolated, synthetic or recombinant antibody or functional part or functional equivalent thereof comprising a heavy chain CDR1 having the sequence of SEQ ID NO:83, a heavy chain CDR2 having the sequence of SEQ ID NO:87, a heavy chain CDR3 having the sequence of SEQ ID NO:91, a light chain CDR1 having the sequence of SEQ ID NO:95, a light chain CDR2 having the sequence of SEQ ID NO:99 and a light chain CDR3 having the sequence of SEQ ID NO:103. Said antibody or functional part or functional equivalent preferably specifically binds to a conformational epitope of HCV protein E2 comprising at least amino acid G530 of the H77 E2 amino acid sequence as depicted in FIG. 1, and/or has HCVpp neutralizing activity in vitro. Also provided are antibodies and functional parts and functional equivalents comprising heavy chain CDR1, CDR2 and CDR3 sequences and light chain CDR1, CDR2 and CDR3 sequences that have at least 80%, preferably at least 85%, more preferably at least 90%, more preferably at least 95%, more preferably at least 96%, more preferably at least 97%, more preferably at least 98%, more preferably at least 99% sequence identity with the sequences of SEQ ID NOs: 83, 87, 91, 95, 99 and 103. Also provided are antibodies and functional parts and functional equivalents thereof comprising heavy chain CDR1, CDR2 and CDR3 sequences and light chain CDR1, CDR2 and CDR3 sequences that differ in at most three, preferably in at most two, more preferably in at most one amino acid from the heavy chain CDR1, CDR2 and CDR3 sequences and the light chain CDR1, CDR2 and CDR3 sequences of antibody AT15-012. An antibody or functional part or functional equivalent according to the invention preferably has the entire heavy chain variable region and light chain variable region sequences of antibody AT15-012, comprising the sequences of SEQ ID NO:107 and SEQ ID NO:111. Also provided are antibodies and functional parts and functional equivalents thereof comprising a heavy chain variable region and a light chain variable region that have at least 80%, preferably at least 85%, more preferably at least 90%, more preferably at least 95%, more preferably at least 96%, more preferably at least 97%, more preferably at least 98%, more preferably at least 99% sequence identity with the sequences of SEQ ID NOs: 107 and 111, respectively. An isolated, synthetic or recombinant antibody or functional part or functional equivalent thereof that competes with antibody AT15-012 for binding to HCV protein E2 is also herewith provided.

The invention further provides an isolated, synthetic or recombinant nucleic acid molecule, or a functional equivalent thereof, encoding at least one CDR sequence of an antibody, functional part or functional equivalent thereof according to the invention. Preferred nucleic acid molecules encode at least the heavy chain CDR1, CDR2 and CDR3 and the light chain CDR1, CDR2 and CDR3 of the same antibody as depicted in Table 1. An "isolated, synthetic or recombinant nucleic acid molecule, or a functional equivalent thereof, encoding at least one CDR sequence of an antibody according to the invention" is herein also referred to as "a nucleic acid molecule according to the invention". Preferably a nucleic acid molecule according to the invention has a length of at least 15 nucleotides, more preferably at least 30 nucleotides, more preferably at least 50 nucleotides, more preferably at least 75 nucleotides. A nucleic acid molecule according to the invention is for instance isolated from a B cell which is capable of producing an antibody according to the invention. Alternatively, a nucleic acid molecule according to the invention is produced recombinantly. Preferably, a nucleic acid molecule according to the invention encodes an antibody or functional part or functional equivalent according to the invention. A nucleic acid molecule according to the invention preferably encodes an antibody or functional part or functional equivalent comprising the heavy and light chain CDR1-3 sequences of an antibody selected from the group consisting of AT12-011, AT12-007, AT12-009, AT12-010, AT13-021, AT15-009, AT15-011, AT15-012 and AT15-015. In some embodiments, a nucleic acid molecule according to the invention encodes a heavy chain variable region and/or a light chain variable region of antibody AT12-011, AT12-007, AT12-009, AT12-010, AT13-021, AT15-009, AT15-011, AT15-012 or AT15-015 as depicted in Table 1. Nucleic acid sequences encoding heavy chain and light chain CDRs of antibodies AT12-011, AT12-007, AT12-009, AT12-010 and AT13-021 are depicted in table 1. However, nucleic acid molecules encoding a heavy or a light chain CDR of an antibody according to the invention comprising nucleic acid sequences which differ from the CDR nucleic acid sequences depicted in Table 1, but which comprise nucleic acid codons encoding the amino acid sequence of said heavy chain or light chain CDRs as depicted in Table 1 are also encompassed by the invention. Nucleic acid molecules encoding one or more heavy or light chain CDRs of a single antibody depicted in Table 1 are preferred. Nucleic acid molecules encoding a heavy and/or light chain CDR of an antibody according to the invention that is modified, for instance by conservative amino acid substitution, are also encompassed by the invention, as long as the resulting CDR sequence has at least 80%, preferably at least 85%, more preferably at least 90%, more preferably at least 95%, more preferably at least 96%, more preferably at least 97%, more preferably at least 98% or 99%, sequence identity with a CDR sequence as depicted in Table 1.

As used herein, a nucleic acid molecule or nucleic acid sequence of the invention preferably comprises a chain of nucleotides, more preferably DNA and/or RNA. In other embodiments a nucleic acid molecule or nucleic acid sequence of the invention comprises other kinds of nucleic acid structures such as for instance a DNA/RNA helix, peptide nucleic acid (PNA), locked nucleic acid (LNA) and/or a ribozyme. Such other nucleic acid structures are referred to as functional equivalents of a nucleic acid sequence. The term "functional equivalent of a nucleic acid molecule" also encompasses a chain comprising non-natural nucleotides, modified nucleotides and/or non-nucleotide building blocks which exhibit the same function as natural nucleotides.

A preferred nucleic acid molecule according to the invention comprises:
- a heavy chain CDR1 sequence comprising a sequence which has at least 80% sequence identity to a sequence selected from the group consisting of SEQ ID NO:41-45 and SEQ ID NO: 113-116, and/or
- a heavy chain CDR2 sequence comprising a sequence which has at least 80% sequence identity to a sequence selected from the group consisting of SEQ ID NO:46-50 and SEQ ID NO: 117-120, and/or
- a heavy chain CDR3 sequence comprising a sequence which has at least 80% sequence identity to a sequence selected from the group consisting of SEQ ID NO:51-55 and SEQ ID NO: 121-124, and/or
- a light chain CDR1 sequence comprising a sequence which has at least 80% sequence identity to a sequence selected from the group consisting of SEQ ID NO:56-60 and SEQ ID NO:125-128, and/or
- a light chain CDR2 sequence comprising a sequence which has at least 80% sequence identity to a sequence selected from the group consisting of SEQ ID NO:61-65 and SEQ ID NO: 129-132, and/or
- a light chain CDR3 sequence comprising a sequence which has at least 80% sequence identity to a sequence selected from the group consisting of SEQ ID NO:66-70 and SEQ ID NO: 133-136. A nucleic acid molecule according to the invention preferably comprises a sequence which has at least 85%, more preferably at least 90%, more preferably at least 95%, more preferably at least 96%, more preferably at least 97%, more preferably at least 98%, more preferably at least 99% sequence identity to said CDR sequences. Preferably, said nucleic acid molecule comprises the sequences of SEQ ID NOs: 41, 46, 51, 56, 61 and 66 or the sequences of SEQ ID NOs; 42, 47, 52, 57, 62 and 67, or the sequences of SEQ ID NOs: 43, 48, 53, 58, 63 and 68, or the sequences of SEQ ID NOs: 44, 49, 54, 59, 63 and 69 or the sequences of SEQ ID NO's: 45, 50, 55, 60, 65 and 70. In some embodiments, said nucleic acid molecule comprises the sequences of SEQ ID NOs: 113, 117, 121, 125, 129 and 133. In some embodiments, said nucleic acid molecule comprises the sequences of SEQ ID NO's: 114, 118, 122, 126, 130 and 134. In some embodiments, said nucleic acid molecule comprises the sequences of SEQ ID NO's: 115, 119, 123, 127, 131 and 135. In some embodiments, said nucleic acid molecule comprises the sequences of SEQ ID NO's: 116, 120, 124, 128, 132 and 136.

Further provided is a nucleic acid molecule or functional equivalent thereof comprising a sequence which has at least 70% sequence identity, preferably at least 75%, more preferably at least 80%, more preferably at least 85%, more preferably at least 90%, more preferably at least 95%, more preferably at least 96%, more preferably at least 97%, more preferably at least 98%, more preferably at least 99% sequence identity with at least one nucleic acid sequence selected from SEQ ID NOs:41-70 and SEQ ID NOs: 113-136, said nucleic acid molecule or functional equivalent having at least 15 nucleotides.

A nucleic acid molecule according to the present invention preferably encodes an amino acid sequence which has at least 80% sequence identity to the amino acid sequence of a heavy chain variable region and/or a light chain variable region of an antibody selected from the group consisting of antibodies AT12-011, AT12-007, AT12-009, AT12-010, AT13-021, AT15-009, AT15-011, AT15-012 and AT15-015 as depicted in Table 1. Thus, a preferred nucleic acid molecule according to the invention comprises a sequence which has at least 80% sequence identity to a sequence selected from the group consisting of SEQ ID NOs: 71-75 and SEQ ID NOs: 137-140 and/or a sequence which has at least 80% sequence identity to a sequence selected from the group consisting of SEQ ID NOs:76-80 and SEQ ID NOs: 141-144. More preferably, a nucleic acid molecule according to the invention comprises a heavy chain variable region encoding sequence and a light chain variable region encoding sequence which resemble the heavy and the light chain variable region encoding sequences of the same antibody depicted in Table 1. Thus, a preferred nucleic acid molecule according to the invention comprises a heavy chain variable region encoding sequence of antibody AT12-011, comprising the sequence of SEQ ID NO:71 and a light chain variable region encoding sequence of antibody AT12-011, comprising the sequence of SEQ ID NO:76, or a sequence that is at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical thereto.

Another preferred nucleic acid molecule according to the invention comprises a heavy chain variable region encoding sequence of antibody AT12-007, comprising the sequence of SEQ ID NO:72 and a light chain variable region encoding sequence of antibody AT12-007, comprising the sequence of SEQ ID NO:77, or a sequence that is at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical thereto.

Another preferred nucleic acid molecule according to the invention comprises a heavy chain variable region encoding sequence of antibody AT12-009, comprising the sequence of SEQ ID NO:73 and a light chain variable region encoding sequence of antibody AT12-009, comprising the sequence of SEQ ID NO:78, or a sequence that is at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical thereto.

Another preferred nucleic acid molecule according to the invention comprises a heavy chain variable region encoding sequence of antibody AT12-010, comprising the sequence of SEQ ID NO:74 and a light chain variable region encoding sequence of antibody AT12-010, comprising the sequence of SEQ ID NO:79, or a sequence that is at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical thereto.

Another preferred nucleic acid molecule according to the invention comprises a heavy chain variable region encoding sequence of antibody AT13-021, comprising the sequence of SEQ ID NO:75 and a light chain variable region encoding sequence of antibody AT13-021, comprising the sequence of SEQ ID NO:80, or a sequence that is at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical thereto.

Another preferred nucleic acid molecule according to the invention comprises a heavy chain variable region encoding sequence of antibody AT15-009, comprising the sequence of SEQ ID NO:137, and a light chain variable region encoding sequence of antibody AT15-009, comprising the sequence of SEQ ID NO:141, or a sequence that is at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% identical thereto.

Another preferred nucleic acid molecule according to the invention comprises a heavy chain variable region encoding sequence of antibody AT15-011, comprising the sequence of SEQ ID NO:138, and a light chain variable region encoding sequence of antibody AT15-011, comprising the sequence of SEQ ID NO:142, or a sequence that is at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical thereto.

Another preferred nucleic acid molecule according to the invention comprises a heavy chain variable region encoding sequence of antibody AT15-012, comprising the sequence of SEQ ID NO:139 and a light chain variable region encoding sequence of antibody AT15-012, comprising the sequence of SEQ ID NO:143, or a sequence that is at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical thereto.

Another preferred nucleic acid molecule according to the invention comprises a heavy chain variable region encoding sequence of antibody AT15-015, comprising the sequence of SEQ ID NO:140, and a light chain variable region encoding sequence of antibody AT15-015, comprising the sequence of SEQ ID NO:144, or a sequence that is at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical thereto.

The invention further provides a vector comprising a nucleic acid molecule according to the invention. As used herein "a vector comprising a nucleic acid molecule according to the invention" is also referred to as "a vector according to the invention". Methods for constructing a vector comprising a nucleic acid molecule or a nucleic acid sequence of a nucleic acid molecule according to the invention are well known in the art. Non-limiting examples of vectors suitable for generating a vector of the invention are retroviral and lentiviral vectors. A vector according to the invention is suitable for a variety of applications. For instance, a vector according to the invention can be used for in vitro expression of a nucleic acid molecule of interest in a cell, i.e. for the generation of antibodies, functional parts or functional equivalents according to the invention. Further, a vector of the invention comprising the nucleic acid sequence of a therapeutically beneficial nucleic acid molecule is suitable for prophylactic or therapeutic applications against HCV. Administration of such vector to an individual, preferably a human, in need thereof results in expression of said prophylactic or therapeutic nucleic acid molecule in vivo resulting in treatment or prophylaxis of HCV infection.

A nucleic acid molecule or vector according to the invention is particularly useful for generating antibodies or functional parts, or immunoglobulin chains or functional equivalents, which are specific for HCV, in particular for the E2 protein of HCV. This is for instance done by introducing such nucleic acid molecule or vector into a cell so that the cell's nucleic acid translation machinery will produce the encoded antibodies or functional parts, immunoglobulin chains or functional equivalents. In one embodiment, a nucleic acid molecule or vector according to the invention is expressed in so called producer cells, such as for instance cells of a Chinese hamster ovary (CHO), NSO (a mouse myeloma) or 293(T) cell line, some of which are adapted to commercial antibody production. Proliferation of such producer cells results in a producer cell line capable of producing antibodies according to the invention. Preferably, said producer cell line is suitable for producing antibodies for use in humans. Hence, said producer cell line is preferably free of pathogenic agents such as pathogenic micro-organisms. Preferably, antibodies consisting of human sequences are generated using a nucleic acid molecule or vector according to the invention. Also provided is therefore an isolated or recombinant cell comprising a nucleic acid molecule or a vector according to the invention. Such isolated or recombinant cell is herein also referred to as an "antibody producing cell" and is defined herein as a cell which is capable of producing and/or secreting antibodies or functional parts or functional equivalents thereof, and/or which is capable of developing into a cell which is capable of producing and/or secreting antibodies or functional parts or functional equivalents thereof. A method for producing an antibody or functional part or functional equivalent according to the invention is also provided, said method comprising providing a cell, preferably an antibody producing cell, with a nucleic acid molecule or a vector according to the invention, and allowing said cell to translate a nucleic acid sequence of said nucleic acid molecule or vector, thereby producing antibodies, functional parts or functional equivalents according to the invention. A method according to the invention preferably further comprises a step of harvesting, purifying and/or isolating the antibodies, functional parts or functional equivalents. Obtained antibodies, functional parts or functional equivalents according to the invention are preferably used in diagnosis or in human prophylactic or therapeutic therapy, optionally after additional purifying, isolation or processing steps.

Antibodies according to the invention are capable of binding and/or neutralizing HCV, in particular the E2 protein of HCV. Antibodies according to the invention are therefore particularly suitable for use in diagnosis. The invention therefore provides an antibody or functional part or functional equivalent according to invention for use in diagnosis, preferably of a HCV infection. Also provided is the use of an antibody or functional part or functional equivalent according to the invention for the preparation of a diagnostic agent for diagnosis of HCV infection. Also provided is the use of an antibody or functional part or functional equivalent according to the invention for determining whether a sample comprises HCV or HCV protein E2 or a HCV E1E2 heterodimer. Antibodies and functional parts and functional equivalents according to the invention are further particularly suitable as a medicament or prophylactic agent. The invention therefore further provides an antibody or functional part or functional equivalent according to the invention for use as a medicament or prophylactic agent. Also provided is the use of an antibody or functional part or functional equivalent according to the invention for the preparation of a medicament or prophylactic agent for the treatment or prevention of HCV infection. Also provided are a nucleic acid molecule or functional equivalent according to the invention, or a vector according to the invention for use as a medicament or prophylactic agent. Further provided is the use of a nucleic acid molecule or functional equivalent according to the invention, or a vector according to the invention for the preparation of a medicament or prophylactic agent for the treatment or prevention of HCV infection. Further provided is a use of antibody or functional part or functional equivalent, or a use of a nucleic acid molecule or functional equivalent thereof or a vector according to the invention for the preparation of a medicament or prophylactic agent for the treatment or prevention of a disorder caused by HCV infection, preferably wherein said disorder is selected from the group consisting of chronic liver disease, such as liver fibrosis, cirrhosis and hepatocellular carcinoma, and extra-hepatic manifestations of chronic HCV infection, such as insuline resistance, mixed cryoglobulinemia, membranoproliferative glomerulonephritis, porphyria cutaneous tarda, lichen planus and vitiligo.

The invention further provides a method for determining whether HCV is present in a sample comprising:
contacting said sample with an antibody or functional part or functional equivalent according to the invention,
allowing said antibody or functional part or functional equivalent to bind HCV if present, and
determining whether HCV is bound to said antibody or functional part or functional equivalent, thereby determining whether HCV is present.

Preferably it is determined whether an individual is suffering from a HCV infection and/or from a disorder caused by HCV infection. Provided is therefore a method for determining whether an individual is suffering from a HCV infection, comprising:
contacting a sample from said individual with an antibody or functional part or functional equivalent according to the invention, and
allowing said antibody or functional part or functional equivalent to bind HCV, if present, and
determining whether or not HCV is bound to said antibody or functional part or functional equivalent, thereby determining whether or nor said individual is suffering from HCV infection. Preferably said individual is a human.

Preferred antibodies for use in diagnosis are antibodies AT12-011, AT12-007, AT12-009, AT12-010, AT13-021, AT15-009, AT15-011, AT15-012 and AT15-015, which have heavy and light chain sequences as depicted in Table 1 or a functional part or functional equivalent thereof as defined herein. Provided is thus antibody AT12-011, comprising a heavy chain variable region sequence of SEQ ID NO:31 and a light chain variable region sequence of SEQ ID NO:36, for use in diagnosis. Also provided is antibody AT12-007, comprising a heavy chain variable region sequence of SEQ ID NO:32 and a light chain variable region sequence of SEQ ID NO:37, for use in diagnosis. Also provided is antibody AT12-009, comprising a heavy chain variable region sequence of SEQ ID NO:33 and a light chain variable region sequence of SEQ ID NO:38, for use in diagnosis. Also provided is antibody AT12-010, comprising a heavy chain variable region sequence of SEQ ID NO:34 and a light chain variable region sequence of SEQ ID NO:39, for use in diagnosis. Also provided is antibody AT13-021, comprising a heavy chain variable region sequence of SEQ ID NO:35 and a light chain variable region sequence of SEQ ID NO:40, for use in diagnosis. Also provided is antibody AT15-009, comprising a heavy chain variable region sequence of SEQ ID NO:105 and a light chain variable region sequence of SEQ ID NO:109, for use in diagnosis. Also provided is antibody AT15-011, comprising a heavy chain variable region sequence of SEQ ID NO:106 and a light chain variable region sequence of SEQ ID NO:110, for use in diagnosis. Also provided is antibody AT15-012, comprising a heavy chain variable region sequence of SEQ ID NO:107 and a light chain variable region sequence of SEQ ID NO:111, for use in diagnosis. Also provided is antibody AT15-015, comprising a heavy chain variable region sequence of SEQ ID NO:108 and a light chain variable region sequence of SEQ ID NO:112, for use in diagnosis.

HCV may be detected using the antibodies of the invention when present in any type of sample. Any sample containing a detectable amount of HCV can be used. Non-limiting examples of a sample are blood, serum, liver tissue, urine and faeces. In a preferred embodiment, such sample is a blood, serum or liver sample. Most preferably such sample is a blood or serum sample. Preferably, a sample is from an individual, preferably a human, that is suspected of suffering from HCV infection.

Diagnosis using an antibody of the invention can be performed by conventional methods known in the art, such as enzyme-linked immunosorbent assays (ELISA) or radio-immuno assays (RIA). For such methods, the antibody can be labelled directly and immune complexes of antibody and antigen can be detected via the label. Examples of labels which can be used include enzymes, fluorescent compounds, radioisotopes, chemiluminescent compounds and bioluminescent compounds. Alternatively, the antibody is unlabelled and the antibody-antigen complex can be detected with an labelled antibody, for instance an enzyme-conjugated antibody, directed against the antibody of the invention.

Kits of parts for performing diagnosis using antibodies according to the invention are also provided. Such kit of part comprises at least one antibody according to the invention, and one or more of the following compounds or parts: an antigen immobilizing material, a labelled antibody, such as an enzyme-conjugated antibody, against the antibody of the invention, an appropriate substrate, a suitable buffer for dilution and washing, and instructions for carrying out a diagnostic test.

An antibody according to the invention for use as a medicament or prophylactic agent preferably consists of human sequences, in order to reduce the chance of adverse side effects when human individuals are treated. Such human sequences can be isolated from a human or synthetically or recombinantly produced based on the sequence of human antibodies. Provided is an antibody according to the invention for use as a medicament and/or prophylactic agent. Also provided is a nucleic acid molecule or functional equivalent thereof according to the invention or a vector according to the invention comprising such nucleic acid molecule for use as a medicament and/or prophylactic agent. When a nucleic acid molecule according to the invention is administered, it will be translated in situ by the host's machinery into an antibody according to the invention. Produced antibodies according to the invention are capable of preventing and/or counteracting HCV infection. Preferred antibodies for use as a medicament or prophylactic agent are antibodies AT12-011, AT12-007, AT12-009, AT12-010, AT13-021, AT15-009, AT15-011, AT15-012 and AT15-015, which have heavy and light chain CDR and variable region sequences as depicted in Table for a functional part or functional equivalent thereof. Provided is thus antibody AT12-011, comprising a heavy chain variable region sequence of SEQ ID NO:31 and a light chain variable region sequence of SEQ ID NO:36, for use as a medicament and/or prophylactic agent. Also provided is antibody AT12-007, comprising a heavy chain variable region sequence of SEQ ID NO:32 and a light chain variable region sequence of SEQ ID NO:37, for use as a medicament and/or prophylactic agent. Also provided is antibody AT12-009, comprising a heavy chain variable region sequence of SEQ ID NO:33 and a light chain variable region sequence of SEQ ID NO:38, for use as a medicament and/or prophylactic agent. Also provided is antibody AT12-010, comprising a heavy chain variable region sequence of SEQ ID NO:34 and a light chain variable region sequence of SEQ ID NO:39, for use as a medicament and/or prophylactic agent. Also provided is antibody AT13-021, comprising a heavy chain variable region sequence of SEQ ID NO:35 and a light chain variable region sequence of SEQ ID NO:40, for use as a medicament and/or prophylactic agent. Also provided is antibody AT15-009, comprising a heavy chain variable region sequence of SEQ ID NO:105 and a light chain variable region sequence of SEQ ID NO:109, for use as a medicament and/or prophylactic agent. Also provided is antibody AT15-011, comprising a heavy chain variable region sequence of SEQ ID NO:106 and a light chain variable region sequence of SEQ ID NO:110, for use as a medicament and/or prophylactic agent. Also provided is antibody AT15-012, comprising a heavy chain variable region sequence of SEQ ID NO:107 and a light chain variable region sequence of SEQ ID NO:111, for use as a medicament and/or prophylactic agent. Also provided is antibody AT15-015, comprising a heavy chain variable region sequence of SEQ ID NO:108 and a light chain variable region sequence of SEQ ID NO:112, for use as a medicament and/or prophylactic agent.

Also provided is a use of antibody AT12-011, comprising a heavy chain variable region sequence of SEQ ID NO:31 and a light chain variable region sequence of SEQ ID NO:36, for the preparation of a medicament and/or prophylactic agent. Also provided is a use of antibody AT12-007, comprising a heavy chain variable region sequence of SEQ ID NO:32 and a light chain variable region sequence of SEQ ID NO:37, for the preparation of a medicament and/or prophylactic agent. Also provided is a use of antibody AT12-009, comprising a heavy chain variable region sequence of SEQ ID NO:33 and a light chain variable region sequence of SEQ ID NO:38, for the preparation of a medicament and/or prophylactic agent. Also provided is a use of antibody AT12-010, comprising a heavy chain variable region sequence of SEQ ID NO:34 and a light chain variable region sequence of SEQ ID NO:39, for the preparation of a medicament and/or prophylactic agent. Also provided is a use of antibody AT13-021, comprising a heavy chain variable region sequence of SEQ ID NO:35 and a light chain variable region sequence of SEQ ID NO:40, for the preparation of a medicament and/or prophylactic agent. Also provided is a use of antibody AT15-009, comprising a heavy chain variable region sequence of SEQ ID NO:105 and a light chain variable region sequence of SEQ ID NO:109, for the preparation of a medicament and/or prophylactic agent. Also provided is a use of antibody AT15-011, comprising a heavy chain variable region sequence of SEQ ID NO:106 and a light chain variable region sequence of SEQ ID NO:110, for the preparation of a medicament and/or prophylactic agent. Also provided is a use of antibody AT15-012, comprising a heavy chain variable region sequence of SEQ ID NO:107 and a light chain variable region sequence of SEQ ID NO:111, for the preparation of a medicament and/or prophylactic agent. Also provided is a use of antibody AT15-015, comprising a heavy chain variable region sequence of SEQ ID NO:108 and a light chain variable region sequence of SEQ ID NO:112, for the preparation of a medicament and/or prophylactic agent.

Also provided is an antibody according to the invention, or a nucleic acid molecule or functional equivalent thereof according to the invention, or a vector according to the invention, for use in a method of at least in part treating and/or preventing a disorder caused by HCV infection, preferably wherein said disorder is selected from the group consisting of chronic liver disease, such as liver fibrosis, cirrhosis and hepatocellular carcinoma, and extra-hepatic manifestations of chronic HCV infection, such as insuline resistance, mixed cryoglobulinemia, membranoproliferative glomerulonephritis, porphyria cutaneous tarda, lichen planus and vitiligo.

Some embodiments provide a use of antibody AT12-011, comprising a heavy chain variable region sequence of SEQ ID NO:31 and a light chain variable region sequence of SEQ ID NO:36, for the preparation of a medicament and/or prophylactic agent against a disorder caused by a HCV infection. Also provided is a use of antibody AT12-007, comprising a heavy chain variable region sequence of SEQ ID NO:32 and a light chain variable region sequence of SEQ ID NO:37, for the preparation of a medicament and/or prophylactic agent against a disorder caused by a HCV infection. Also provided is a use of antibody AT12-009, comprising a heavy chain variable region sequence of SEQ ID NO:33 and a light chain variable region sequence of SEQ ID NO:38, for the preparation of a medicament and/or prophylactic agent against a disorder caused by a HCV infection. Also provided is a use of antibody AT12-010, comprising a heavy chain variable region sequence of SEQ ID NO:34 and a light chain variable region sequence of SEQ ID NO:39, for the preparation of a medicament and/or prophylactic agent against a disorder caused by a HCV infection. Also provided is a use of antibody AT13-021, comprising a heavy chain variable region sequence of SEQ ID NO:35 and a light chain variable region sequence of SEQ ID NO:40, for the preparation of a medicament and/or prophylactic agent against a disorder caused by a HCV infection. Also provided is a use of antibody AT15-009, comprising a heavy chain variable region sequence of SEQ ID NO:105 and a light chain variable region sequence of SEQ ID NO:109, for the preparation of a medicament and/or prophylactic agent against a disorder caused by a HCV infection. Also provided is a use of antibody AT15-011, comprising a heavy chain variable region sequence of SEQ ID NO:106 and a light chain variable region sequence of SEQ ID NO:110, for the preparation of a medicament and/or prophylactic agent against a disorder caused by a HCV infection. Also provided is a use of antibody AT15-012, comprising a heavy chain variable region sequence of SEQ ID NO:107 and a light chain variable region sequence of SEQ ID NO:111, for the preparation of a medicament and/or prophylactic agent against a disorder caused by a HCV infection. Also provided is a use of antibody AT15-015, comprising a heavy chain variable region sequence of SEQ ID NO:108 and a light chain variable region sequence of SEQ ID NO:112, for the preparation of a medicament and/or prophylactic agent against a disorder caused by a HCV infection.

The invention further provides a pharmaceutical composition comprising an antibody according to the invention, and a pharmaceutical acceptable carrier, diluent and/or excipient. Also provided is a pharmaceutical composition comprising a nucleic acid molecule according to the invention, or a vector according to the invention comprising such nucleic acid molecule, and a pharmaceutical acceptable carrier, diluent and/or excipient. Examples of suitable carriers for instance comprise a solution, like for example saline, keyhole limpet haemocyanin (KLH), serum albumin (e.g. BSA or RSA) and ovalbumin. A pharmaceutical composition according to the invention is preferably suitable for human use. A "pharmaceutical composition comprising an antibody or functional part or functional equivalent, or a nucleic acid molecule, or a vector according to the invention and a pharmaceutically acceptable carrier, diluent and/or excipient" is herein also referred to as a pharmaceutical composition according to the invention.

A pharmaceutical composition according to the invention may further comprise an adjuvant. Examples of adjuvants which can be incorporated in tablets, capsules and the like are a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

The invention further provides a method for treating and/or preventing HCV infection or a HCV related disorder, comprising administering to an individual in need thereof a therapeutically effective amount of an antibody or functional part or functional equivalent according to the invention, or a nucleic acid molecule or functional equivalent according to the invention, or a vector according to the invention, or a pharmaceutical composition according to the invention. Further provided is a method for treating and/or preventing a disorder caused by HCV infection, preferably wherein said disorder is selected from the group consisting of chronic liver disease, such as liver fibrosis, cirrhosis and hepatocellular carcinoma, and extra-hepatic manifestations of chronic HCV infection, such as insuline resistance, mixed cryoglobulinemia, membranoproliferative glomerulonephritis, porphyria cutaneous tarda, lichen planus and vitiligo, comprising administering to an individual in need thereof a therapeutically effective amount of an antibody or functional part or functional equivalent according to the invention, or a nucleic acid molecule or functional equivalent according to the invention, or a vector according to the invention, or a pharmaceutical composition according to the invention. As used herein, an "individual" is a human or an animal, preferably an animal that can be infected by HCV. In a preferred embodiment of the invention said individual is a human.

Features may be described herein as part of the same or separate aspects or embodiments of the present invention for the purpose of clarity and a concise description. It will be appreciated by the skilled person that the scope of the invention may include embodiments having combinations of all or some of the features described herein as part of the same or separate embodiments.

The invention will be explained in more detail in the following, non-limiting examples.

TABLE 1

Amino acid and nucleotide sequences of preferred
HCV specific antibodies according to the invention
(CDR numbering according to Kabat et al (1991))

| SEQ ID NO | Antibody | Identity | Sequence |
|---|---|---|---|
| 1 | AT12-011 | Heavy chain CDR1 | GYGIT |
| 2 | AT12-007 | Heavy chain CDR1 | ELSMH |
| 3 | AT12-009 | Heavy chain CDR1 | THAIS |
| 4 | AT12-010 | Heavy chain CDR1 | YAIN |
| 5 | AT13-021 | Heavy chain CDR1 | THAFS |
| 6 | AT12-011 | Heavy chain CDR2 | TIIPVSATETYAQRLQG |
| 7 | AT12-007 | Heavy chain CDR2 | SFDPADGERLYAQKFQG |
| 8 | AT12-009 | Heavy chain CDR2 | GTVRQAPGDGLELLGGFVPILAPANDAQKFQG |
| 9 | AT12-010 | Heavy chain CDR2 | EISPVFGTTHYAQKFQG |
| 10 | AT13-021 | Heavy chain CDR2 | GISPMSGTPNYAQKFQG |
| 11 | AT12-011 | Heavy chain CDR3 | HDYFWGTPLDI |
| 12 | AT12-007 | Heavy chain CDR3 | APRMTMFGVIMALDS |
| 13 | AT12-009 | Heavy chain CDR3 | SLSEPIPRSCRGGRCYSGPFDAFGV |
| 14 | AT12-010 | Heavy chain CDR3 | DRAPRLCSGGRCHSPPDH |
| 15 | AT13-021 | Heavy chain CDR3 | ELIGYCTGGNCYSFGDF |
| 16 | AT12-011 | Light chain CDR1 | RASQSIGSNLH |
| 17 | AT12-007 | Light chain CDR1 | RASQNINKYLA |
| 18 | AT12-009 | Light chain CDR1 | RASQSIGTNLA |
| 19 | AT12-010 | Light chain CDR1 | RASQGFGNWLA |
| 20 | AT13-021 | Light chain CDR1 | RASQSVSSHLA |
| 21 | AT12-011 | Light chain CDR2 | YASQSFS |
| 22 | AT12-007 | Light chain CDR2 | KASNLQS |
| 23 | AT12-009 | Light chain CDR2 | GASTRAT |
| 24 | AT12-010 | Light chain CDR2 | GASTLQN |
| 25 | AT13-021 | Light chain CDR2 | GASTRAV |
| 26 | AT12-011 | Light chain CDR3 | HQSYNLP |
| 27 | AT12-007 | Light chain CDR3 | QQYTTYSA |
| 28 | AT12-009 | Light chain CDR3 | QQYNNWP |
| 29 | AT12-010 | Light chain CDR3 | LQTNTFP |
| 30 | AT13-021 | Light chain CDR3 | HQYNTWP |
| 31 | AT12-011 | Heavy chain | QVQLVQSGAEVKKPGSSVKVSCKASGGTFSGYGITWVRQAPGQGLEWMGTIIPVSATETYAQR LQGRVTISADEHSTTSYMEVSSLKSEDTALYYCARHDYFWGTPLDIWGQGTMV TABLE 1-continued Amino acid and nucleotide sequences of preferred
HCV specific antibodies according to the invention
(CDR numbering according to Kabat et al (1991))

| SEQ ID NO | Antibody | Identity | Sequence |
|---|---|---|---|
| 35 | AT13-021 | Heavy chain | QVQLVQSGAEVKKPGSSVKVSCKASGGTENTHAFSWVRQAPGEGLEWMGGISPMSGTPNYAQK<br>FQGRLTITADESTSTGYMELRSLTSEDTAVYYCARELIGYCTGGNCYSFGDFWGQGTLITVSS |
| 36 | AT12-011 | Light chain | EIVLTQSPDFQSVTPKEKVTITCRASQSIGSNLHWYQQKPGQSPKLLIKYASQSFSGVPSRFS<br>GSGSGTDFTLTINSLEAEDAATYFCHQSYNLPRTFGGGTKVEIKRTVAA |
| 37 | AT12-007 | Light chain | DIQMTQSPSTLSASLGDRVTITCRASQNINKYLAWYQQKPGKAPKLLIYKASNLQSGVPSRFS<br>GSGSGTDFILTISSLQPDDFATYYCQQYTTYSAWTFGQGTNVDIKRTVA |
| 38 | AT12-009 | Light chain | ETMLTQSPVTLSVSPGERATLSCRASQSIGTNLAWYQQKPGQAPRLLIHGASTRATGVPVSFS<br>GSGSGTEFTLTISSLQSEDFAVYYCQQYNNWPLTFGGGTKVDFKRTVAA |
| 39 | AT12-010 | Light chain | DIQMTQSPSSVSASVGDRVTITCRASQGFNWLAWYQQKPGRAPKLLIFGASTLQNGVPSRFS<br>GSASGTDFTLTITSLQPEDFATYYCLQTNTFPYTFGQGTKVEIKRTVAA |
| 40 | AT13-021 | Light chain | EIVMTQSPATLSVSPGERATLSCRASQSVSSHLAWYQHKPGQAPRLLISGASTRAVGVPARFS<br>GSGSGTEFTLTISSLQSEDFAVYYCHQYNTWPRGFGQGTKVDFKRTVAA |
| 41 | AT12-011 | Heavy chain CDR1 | gga tat ggt atc acc |
| 42 | AT12-007 | Heavy chain CDR1 | gag tta tcc atg cac |
| 43 | AT12-009 | Heavy chain CDR1 | act cat gcc atc agt |
| 44 | AT12-010 | Heavy chain CDR1 | tat gct atc aac |
| 45 | AT13-021 | Heavy chain CDR1 | acc cat gca ttc agc |
| 46 | AT12-011 | Heavy chain CDR2 | aca atc atc cct gtt tct gct acg gaa acc tac gca cag agg ttg cag ggc |
| 47 | AT12-007 | Heavy chain CDR2 | agt ttt gat cct gca gat ggt gaa aga ctt tac gca cag aag ttc cag gga |
| 48 | AT12-009 | Heavy chain CDR2 | ggg acc gtg cga cag gcc ccc gga gac ggg ctt gag ttg ctg gga ggg<br>ttc gtc ccc atc ctt gct cca gcg aac gac gcc cag aag ttc cag ggc |
| 49 | AT12-010 | Heavy chain CDR2 | gag atc agc cct gtc ttt gga aca aca cac tac gca cag aag ttc cag ggc |
| 50 | AT13-021 | Heavy chain CDR2 | ggg atc agc cct atg tct ggc aca cca aac tac gca cag aaa ttc cag ggc |
| 51 | AT12-011 | Heavy chain CDR3 | cac gac tac ttt tgg ggg act ccg ctt gat at c |
| 52 | AT12-007 | Heavy chain CDR3 | gcc cca cgt atg acg atg ttt ggg gtg ata atg gcc tta gac tcc |
| 53 | AT12-009 | Heavy chain CDR3 | tcg ctt tca gaa ccc ata cca agg tct tgt cgt ggt ggt aga tgc tac<br>tcc ggc cct ttt gat gct ttt ggt gtt |
| 54 | AT12-010 | Heavy chain CDR3 | gat agg gcc cct aga ttg tgt agt ggt ggt cgc tgc cac tcc ccc cct gac cac |
| 55 | AT13-021 | Heavy chain CDR3 | gag ttg atc ggg tat tgc act ggt ggt aac tgc tac tca ttc ggt gac ttt |
| 56 | AT12-011 | Light chain CDR1 | cgg gcc agt cag agc att ggt agt aat tta cac |
| 57 | AT12-007 | Light chain CDR1 | cgg gcc agt cag aat att aat aaa tat ttg gcc |
| 58 | AT12-009 | Light chain CDR1 | agg gcc agt cag agt att ggt acc aac tta gcc |
| 59 | AT12-010 | Light chain CDR1 | cgg gcg agt cag ggt ttt ggc aac tgg tta gcc |
| 60 | AT13-021 | Light chain CDR1 | agg gcc agt cag agt gtt agc agc cac tta gcc |
| 61 | AT12-011 | Light chain CDR2 | tat gct tcc cag tcc ttc tca |
| 62 | AT12-007 | Light chain CDR2 | aag gcg tct aat tta caa agt |
| 63 | AT12-009 | Light chain CDR2 | ggt gca tct acc agg gcc act |

TABLE 1-continued

Amino acid and nucleotide sequences of preferred
HCV specific antibodies according to the invention
(CDR numbering according to Kabat et al (1991))

| SEQ ID NO | Antibody | Identity | Sequence |
|---|---|---|---|
| 64 | AT12-010 | Light chain CDR2 | ggt gca tcc act ttg caa aat |
| 65 | AT13-021 | Light chain CDR2 | ggt gca tcc acc agg gcc gtt |
| 66 | AT12-011 | Light chain CDR3 | cat cag agt tat aat tta ccg |
| 67 | AT12-007 | Light chain CDR3 | caa cag tat act act tat tcc gcg |
| 68 | AT12-009 | Light chain CDR3 | cag cag tat aat aac tgg cct |
| 69 | AT12-010 | Light chain CDR3 | cta caa act aac acc ttc cct |
| 70 | AT13-021 | Light chain CDR3 | cac cag tat aat acc tgg ccc |
| 71 | AT12-011 | Heavy chain | cag gtg cag ctg gtg cag tct ggg gct gag gtg aag aag ccc ggg tcc tcg gtg aag gtc tcc tgc aag gcc tct gga ggc acc ttc agc gga tat ggt atc acc tgg gtg cga cag gcc cct gga caa ggg ctt gag tgg atg gga aca atc atc cct gtt tct gct acg gaa acc tac gca cag agg ttg cag ggc agg gtc aca att tcc gcg gac gaa cat tca acc acg tcc tat atg gag gtg agc agc ctg aaa tct gaa gac acg gcc ctt tat tac tgt gcg aga cac gac tac ttt tgg ggg act ccg ctt gat atc tgg ggc caa ggg acg atg gtc atc gtc tct tca |
| 72 | AT12-007 | Heavy chain | cag gtc caa ctg gaa cag tct ggg gct gag gtg aag aag cct ggg gcc tca gtg aag gtc tcc tgc aag gtg tcc gga tac acc ctc act gag tta tcc atg cac tgg gtg cga cag gct cct gga aaa ggg ctt gag tgg atg ggc agt ttt gat cct gca gat ggt gaa aga ctt tac gca cag aag ttc cag gga aga gtc atc atg agc gaa gac aca tct aca gac aca gcc tac atg gag ttg agc agc ctg aga tct gag gac gcg gcc gtg tat tac tgt gcg act gcc cca cgt atg acg atg ttt ggg gtg ata atg gcc tta gac tcc tgg ggc cag gga acc ctg gtc acc gtc tcc tca |
| 73 | AT12-009 | Heavy chain | cag gag cgc ctg gtg cag tct ggg gct gag gtg aag aag cct ggg tcc tcg gtg agg gtc tcc tgc aag gct tct gga gac acc ttc aag act cat gcc atc agt act cat gcc atc agt ggg acc atc gcc gtg cga cag gcc ccc gga gac ggg ctt gag ttg ctg gga ggg ttc gtc ccc atc ctt gct cca gcg aac gac gcc cag aag ttc cag ggc aga gtc acg atc acc gcg gac ggg tcc acg ggc cca gtc tac atg gac ctg agc acc ctg aca tct gag gac acg gcc atg tat tac tgt gtg aca tcg ctt tca gaa ccc ata cca agg tct tgt cgt ggt ggt aga tgc tac tcc ggc cct ttt gat gct ttt ggt gtt tgg ggc caa ggg aca atg gtc acc gtc tct tca |
| 74 | AT12-010 | Heavy chain | caa ctg caa ttg gtg cag tct ggg gct gag gtg aag aag cct ggg tcc tcg gtg aag gtc tcc tgc aag gct tct gga ggc acc ttc acc agc tat gct atc aac tgg gtg cga cag gtc cct gga caa gga ctt gag tgg atg gga gag atc agc cct gtc ttt gga aca aca cac tac gca cag aag ttc cag ggc aga ctc aag att acc gcg gac aaa tcc gcg gac aca gcc tac atg gag ctg agc agc ctg aga tct gat gac acg gcc gtt tat tat tgt ggg aga gat agg gcc cct aga ttg tgt agt ggt ggt cgc tgc cac tcc ccc cct gac cac tgg ggc cag ggg acc ctg gtc acc gtc tcc tca |
| 75 | AT13-021 | Heavy chain | cag gtg caa ctg gtg cag tct ggg gct gag gtg aag aag cct ggg tct tcg gtg aag gtc tcc tgc aag gct tct gga ggc acc ttc aac acc cat gca ttc agc tgg gtg cga cag gcc cct gga gaa ggg ctt gag tgg atg ggg ggg atc agc cct atg tct ggc aca cca aac tac gca cag aaa ttc cag ggc aga ctc acc att acc gcg gac gaa tcc acg agc aca ggc tac atg gag ctg aga agc ctg aca tct gag gac acg gcc gtg tat tac tgt gcg aga gag ttg atc ggg tat tgc act ggt ggt aac tgc tac tca ttc ggt gac ttt tgg ggc cag gga acc ctg att acc gtc tcg tca |
| 76 | AT12-011 | Light chain | gaa att gtg ctg act cag tct cca gac ttt cag tct gtg act cca aag gag aaa gtc acc atc acc tgc cgg gcc agt cag agc att ggt agt aat tta cac tgg tac cag cag aaa cca ggt cag tct cca aag ctc ctc atc aag tat gct tcc agt tca ggg gtc ccc tcg agg ttc agt ggc agt gga tct ggg act gat ttc acc ctc acc atc aat agc ctg gaa gct gaa gat gct gca acg tat ttc tgt cat cag agt tat aat tta ccg agg act ttc ggc ggg ggg acc aag gtg gag atc aaa cga act gtg gct gca |
| 77 | AT12-007 | Light chain | gac atc cag atg acc cag tct cct tcc acc ctg tct gca tct tta gga gac aga gtt acc atc act tgc cgg gcc agt cag aat att aat aaa tat ttg gcc tgg tat cag cag aaa cca ggg aaa gcc cct aaa ctc ctc atc tat aag gcg tct aat tta caa agt ggg gtc ccg tca agg ttc agc ggc agt ggt tct ggg aca gac ttc att ctc acc atc agc agc ctg caa cct |

TABLE 1-continued

Amino acid and nucleotide sequences of preferred
HCV specific antibodies according to the invention
(CDR numbering according to Kabat et al (1991))

| SEQ ID NO | Antibody | Identity | Sequence |
|---|---|---|---|
| | | | gat gat ttt gca act tat tac tgc caa cag tat act act tat tcc gcg tgg act ttc ggc caa ggg acc aac gtg gac atc aaa cga act gtg gct gca |
| 78 | AT12-009 | Light chain | gag aca atg ttg acg cag tct cca gtc acc ctg tct gtg tct cca ggg gaa aga gcc acc ctc tcc tgc agg gcc agt cag agt att ggt acc aac tta gcc tgg tac cag cag aag cct ggc cag gct ccc agg ctc ctc att cat ggt gca tct acc agg gcc act ggt gtc cca gtc agt ttc agt ggc agt ggg tct ggg aca gag ttc act ctc acc atc agc agc ctg cag tct gaa gat ttt gca gtc tat tac tgc cag cag tat aat aac tgg cct ctc act ttt ggc gga ggg acc aag gtg gac ttc aaa cga act gtg gct gca |
| 79 | AT12-010 | Light chain | gac atc cag atg acc cag tct cct tct tcc gtg tct gca tct gta ggc gac aga gtc acc atc act tgt cgg gcg agt cag ggt ttt ggc aac tgg tta gcc tgg tat cag cag aaa cca ggg agg gcc cct aag ctc ctg atc ttt ggt gca tcc act ttg caa aat ggg gtc cca tca agg ttc agc ggc agt gcg tct ggg aca gat ttc act ctc acc atc acc agc ctg cag cct gaa gat ttt gca acc tac tat tgt cta caa act aac acc ttc cct tat act ttt ggc cag ggg acc aag gtg gag atc aaa cga act gtg gct gca |
| 80 | AT13-021 | Light chain | gaa ata gtg atg acg cag tct cca gcc acc ctg tct gtg tct cca ggg gaa aga gcc acc ctc tcc tgc agg gcc agt cag agt gtt agc agc cac tta gcc tgg tac cag cac aaa cct ggc cag gct ccc agg ctc ctc atc tct ggt gca tcc acc agg gcc gtt ggt gtc cca gcc agg ttc agt ggc agt ggg tct ggg aca gag ttc act ctc acc atc agc agc ctg cag tct gag gat ttt gca gtt tat tac tgt cac cag tat aat acc tgg ccc cgg ggg ttc ggc caa ggg acc aag gtg gac ttc aaa cga act gtg gct gca |
| 81 | AT15-009 | Heavy chain CDR1 | TYAIS |
| 82 | AT15-011 | Heavy chain CDR1 | KYYWS |
| 83 | AT15-012 | Heavy chain CDR1 | IFPIT |
| 84 | AT15-015 | Heavy chain CDR1 | KYYWS |
| 85 | AT15-009 | Heavy chain CDR2 | GIVPMFGITNYAQHFQG |
| 86 | AT15-011 | Heavy chain CDR2 | FIYYSGNTNYNPSLKS |
| 87 | AT15-012 | Heavy chain CDR2 | EIIPMLGTPEYAQKFQG |
| 88 | AT15-015 | Heavy chain CDR2 | FIYYSGSTNYNPSLKS |
| 89 | AT15-009 | Heavy chain CDR3 | DLRSGGTFFSRGFDL |
| 90 | AT15-011 | Heavy chain CDR3 | GARGASGYYTDSFFDS |
| 91 | AT15-012 | Heavy chain CDR3 | TETTLPGTLFFVYYFHF |
| 92 | AT15-015 | Heavy chain CDR3 | GARGSSGYYTDSFFDS |
| 93 | AT15-009 | Light chain CDR1 | RASQSVSSSFLT |
| 94 | AT15-011 | Light chain CDR1 | RASQGFSNCLA |
| 95 | AT15-012 | Light chain CDR1 | RASQSVSSSLA |
| 96 | AT15-015 | Light chain CDR1 | RASQGISNYLA |
| 97 | AT15-009 | Light chain CDR2 | DASTRAT |
| 98 | AT15-011 | Light chain CDR2 | ATSPLQS |
| 99 | AT15-012 | Light chain CDR2 | GASTRAT |
| 100 | AT15-015 | Light chain CDR2 | AASPLQS |
| 101 | AT15-009 | Light chain CDR3 | QQFDSSP |
| 102 | AT15-011 | Light chain CDR3 | QKYNRAP |
| 103 | AT15-012 | Light chain CDR3 | QQYNDRPP |

TABLE 1-continued

Amino acid and nucleotide sequences of preferred
HCV specific antibodies according to the invention
(CDR numbering according to Kabat et al (1991))

| SEQ ID NO | Antibody | Identity | Sequence |
|---|---|---|---|
| 104 | AT15-015 | Light chain CDR3 | QNYNRAP |
| 105 | AT15-009 | Heavy chain | QVLLVQSGAEVKKPGSSVKVSCKASGGTFSTYAISWLRQAPGQGPEWMGGIVPMFGITNYAQHFQGRITITADKSTSTAYMELSSLGSEDTAVYFCARDLRSGGTFFSRGFDLWGPGTKVTVSS |
| 106 | AT15-011 | Heavy chain | QVQLQESGPGLVKPSETLSLTCTVSGDSISKYYWSWVRQPPGKGLEWIGFIYYSGNTNYNPSLKSRVTISVDTSNNKFSLKLSSATAADTAVYYCARGARGASGYYTDSFFDSWGQGALVTVSS |
| 107 | AT15-012 | Heavy chain | QVQLVQSGAEVKKPGSSVKVSCKASGGNFNIFPITWVRQAPGQGLEWMGEIIPMLGTPEYAQKFQGRVTITADKSTGTAFMELSSLRSEDTAVYYCARTETTLPGTLFFVYYFHFWGQGTPVTVSS |
| 108 | AT15-015 | Heavy chain | QVQLQESGPGLVKPSETLSLTCTVSGDSISKYYWSWVRQPPGKGLEWIGFIYYSGSTNYNPSLKSRVTISVDTSNNKFSLKVTSATAADTAVYYCARGARGSSGYYTDSFFDSWGQGALVTVSS |
| 109 | AT15-009 | Light chain | EIVLTQSPGTLSLSPGERATLSCRASQSVSSSFLTWYQQKPGQAPRLLIFDASTRATGVPDRFSGSGSGTDFTLTISRLEPEDFGVYYCQQFDSSPTFGGGTKVEIK |
| 110 | AT15-011 | Light chain | DIQMTQSPSSLSASVGDRITITCRASQGFSNCLAWCQQKPGTVLKLLIYATSPLQSGVPSRFSDSGSGTDFTLTISSLQPEDVATYYCQKYNRAPLPGTTVDIK |
| 111 | AT15-012 | Light chain | EIVMTQSPVTLSVSPGERAILSCRASQSVSSSLAWYQQKPGQAPRLLIYGASTRATGVPARFSGSGSGTEFTLTISSVQSEDYAIYFCQQYNDRPPWTFGQGTKVEIK |
| 112 | AT15-015 | Light chain | DIQMTQSPSSLSASVGDRITITCRASQGISNYLAWYQQKPGAVLNLPIYAASPLQSGVPSRFSDSGSGTDFTLTITSLQPEDVATYYCQNYNRAPLPGTKVDIK |
| 113 | AT15-009 | Heavy chain CDR1 | acc tat gct atc agc |
| 114 | AT15-011 | Heavy chain CDR1 | aaa tac tac tgg agc |
| 115 | AT15-012 | Heavy chain CDR1 | att ttt cct atc acc |
| 116 | AT15-015 | Heavy chain CDR1 | aaa tac tac tgg agc |
| 117 | AT15-009 | Heavy chain CDR2 | ggg atc gtc cct atg ttt ggt att aca aac tac gca cag cat ttc cag ggc |
| 118 | AT15-011 | Heavy chain CDR2 | ttt atc tat tac agt ggg aac acc aac tac aac ccc tcc ctc aag agt |
| 119 | AT15-012 | Heavy chain CDR2 | gag atc atc cct atg tta ggg aca cct gag tac gca cag aag ttc cag ggc |
| 120 | AT15-015 | Heavy chain CDR2 | ttt atc tat tac agt ggg agc acc aac tac aac ccc tcc ctc aag agt |
| 121 | AT15-009 | Heavy chain CDR3 | gat ctg cgt agt ggt ggg act ttt tct cgt ggt ttt gat tta |
| 122 | AT15-011 | Heavy chain CDR3 | ggt gcc cga ggt gct agt ggt tat tac acc gat tct ttt ttt gac tcc |
| 123 | AT15-012 | Heavy chain CDR3 | acg gaa aca act cta cct gga aca ctc ttt ttc gtt tac tac ttt cac ttc |
| 124 | AT15-015 | Heavy chain CDR3 | ggt gcc cga ggt agt agt ggt tat tac acc gat tct ttt ttt gac tcc |
| 125 | AT15-009 | Light chain CDR1 | agg gcc agt cag agt gtt agc agc agc ttc tta acc |
| 126 | AT15-011 | Light chain CDR1 | cgg gcg agt cag ggc ttt agc aat tgt tta gcc |
| 127 | AT15-012 | Light chain CDR1 | agg gcc agt cag agt gtt agc agc agc tta gcc |
| 128 | AT15-015 | Light chain CDR1 | cgg gcg agt cag ggc att agc aat tat tta gcc |
| 129 | AT15-009 | Light chain CDR2 | gat gca tcc acc agg gcc act |
| 130 | AT15-011 | Light chain CDR2 | gct aca tcc cct ttg caa tca |
| 131 | AT15-012 | Light chain CDR2 | ggt gca tcc acc agg gcc act |
| 132 | AT15-015 | Light chain CDR2 | gct gca tcc cct ttg caa tca |
| 133 | AT15-009 | Light chain CDR3 | cag cag ttt gat agt tct ccc |
| 134 | AT15-011 | Light chain CDR3 | caa aag tat aac aga gcc ccc |

TABLE 1-continued

Amino acid and nucleotide sequences of preferred
HCV specific antibodies according to the invention
(CDR numbering according to Kabat et al (1991))

| SEQ ID NO | Antibody | Identity | Sequence |
|---|---|---|---|
| 135 | AT15-012 | Light chain CDR3 | caa cag tat aat gac agg cct ccg |
| 136 | AT15-015 | Light chain CDR3 | caa aac tat aac aga gcc ccc |
| 137 | AT15-009 | Heavy chain | cag gtg ctt ctg gtg cag tct ggg gct gag gtg aag aag cct ggg tcc tcg gtg aaa gtc tcc tgt aag gct tct gga ggc acc ttc agc acc tat gct atc agc tgg ctg cga cag gcc cct ggc caa ggg cct gag tgg atg gga ggg atc gtc cct atg ttt ggt att aca aac tac gca cag cat ttc cag ggc aga atc acc att acc gcg gac aaa tcc acg agc aca gcc tac atg gaa ctg agc agc ctg gga tct gag gac acg gcc gtg tat ttt tgt gcg aga gat ctg cgt agt ggt ggg act ttt ttc tct cgt ggt ttt gat tta tgg ggc cca ggg aca aag gtc acc gtc tct tca |
| 138 | AT15-011 | Heavy chain | cag gtg cag ctg cag gag tcg ggc cca gga ctg gtg aag cct tcg gag acc ctg tcc ctc acc tgc acg gtc tct ggt gac tcc atc agt aaa tac tac tgg agc tgg gtc cgg cag ccc cca ggg aag gga ctg gag tgg att ggt ttt atc tat tac agt ggg aac acc aac tac aac ccc tcc ctc aag agt cga gtc acc ata tca gta gac acg tcc aac aac aag ttc tcc ctg aaa ctg agc tct gcg acc gct gcg gac acg gcc gtg tat tac tgt gcg aga ggt gcc cga ggt gct agt ggt tat tac acc gat tct ttt ttt gac tcc tgg ggc cag gga gcc ctg gtc acc gtc tcc tca |
| 139 | AT15-012 | Heavy chain | cag gtg cag ctg gtg cag tct ggg gct gag gtg aag aag cct ggg tcc tcg gtg aag gtc tcc tgc aag gct tct gga ggc aac ttc aac att ttt cct atc acc tgg gtg cga cag gcc cct gga caa ggg ctt gag tgg atg ggc gag atc atc cct atg tta ggg aca cct gag tac gca cag aag ttc cag ggc aga gtc acg ata acc gcg gac aaa tcc acg gga ctg gcc ttc atg gag ctg agc agc ctg aga tct gag gac acg gcc gtt tat tac tgt gct aga acg gaa aca act cta cct gga aca ctc ttt ttc gtt tac tac ttt cac ttc tgg ggc cag gga acc ccg gtc acc gtc tcc tca |
| 140 | AT15-015 | Heavy chain | cag gtg cag ctg cag gag tcg ggc cca gga ctg gtg aag cct tcg gag acc ctg tcc ctc acc tgc act gtc tct ggt gac tcc atc agt aaa tac tac tgg agc tgg gtc cgg cag ccc cca ggg aag gga ctg gag tgg att ggg ttt atc tat tac agt ggg agc acc aac tac aac ccc tcc ctc aag agt cga gtc acc ata tca gta gac acg tcc aac aac aag ttc tcc ctg aag gtg acc tct gcg acc gct gcg gac acg gcc gtg tat tac tgt gcg aga ggt gcc cga ggt agt agt ggt tat tac acc gat tct ttt ttt gac tcc tgg ggc cag gga gcc ctc gtc acc gtc tcc tca |
| 141 | AT15-009 | Light chain | gaa att gtg ttg acg cag tct cca ggc acc ctg tct ttg tct cca ggg gaa aga gcc acc ctc tcc tgc agg gcc agt cag agt gtt agc agc agc ttc tta acc tgg tac cag cag aaa cct ggc cag gct ccc agg ctc ctc atc ttt gat gca tcc acc agg gcc act ggc gtc cca gac agg ttc agt ggc agt ggg tct ggg aca gac ttc act ctc acc atc agc aga ctg gag cct gaa gat ttt gga gtc tat tac tgt cag cag ttt gat agt tct ccc act ttc ggc gga ggg acc aag gtg gag atc aaa |
| 142 | AT15-011 | Light chain | gac atc cag atg acc cag tct cca tcc tcc ctg tct gca tct gta gga gac aga atc acc atc act tgc cgg gcg agt cag ggc ttt agc aat tgt tta gcc tgg tat cag cag aaa cca ggg aca gtt ctt aag ctt ctg atc tat gct aca tcc cct ttg caa tca ggg gtc cca tct cgg ttc agt gac agt gga tct ggg aca gat ttc act ctc acc atc agc agc ctg cag cct gaa gat gtt gca act tat tac tgt caa aag tat aac aga gcc ccc ctc cct ggg acc aca gtg gat atc aaa |
| 143 | AT15-012 | Light chain | gaa ata gtg atg acg cag tct cca gtc acc ctg tct gtg tct cca ggg gaa aga gcc atc ctc tcc tgc agg gcc agt cag agt gtt agc agc agc tta gcc tgg tac cag cag aaa cct ggc cag gct ccc agg ctc ctc atc tat ggt gca tcc acc agg gcc act ggt gtc cca gcc agg ttc agt ggc agt ggg tct ggg aca gag ttc act ctc acc atc agc agc gtg cag tct gaa gat tac gca att tat ttc tgt caa cag tat aat gac agg cct ccg tgg acg ttc ggc caa ggg acc aag gtg gag atc aaa |
| 144 | AT15-015 | Light chain | gac atc cag atg acc cag tct cca tcc tcc ctg tct gca tct gta gga gac aga atc acc atc act tgc cgg gcg agt cag ggc att agc aat tat tta gcc tgg tat cag cag aaa cca ggg aca gct ctt aac ctt ccg atc tat gct gca tcc cct ttg caa tca ggg gtc cca tct cgg ttc agt gac agt gga tct ggg aca gat ttc act ctc acc atc acc agc ctg cag cct gaa gat gtt gca act tat tac tgt caa aac tat aac aga gcc ccc ctc cct ggg acc aaa gtg gat atc aaa |

BRIEF DESCRIPTION OF THE DRAWINGS

FIG. 1. Amino acid sequence of the E2 protein (corresponding to residues 384-746 of the polyprotein) from HCV genotype 1a, strain H77 (SEQ ID NO: 145) and the E2 protein of HCV genotype 2b, isolate AMS.2b.20876551.kloon21 (SEQ ID NO: 146)

The H77 sequence corresponds to Genbank accession number AAB67037 with three amino acid changes: R564C, V566A, and G650E.

Figure 2:
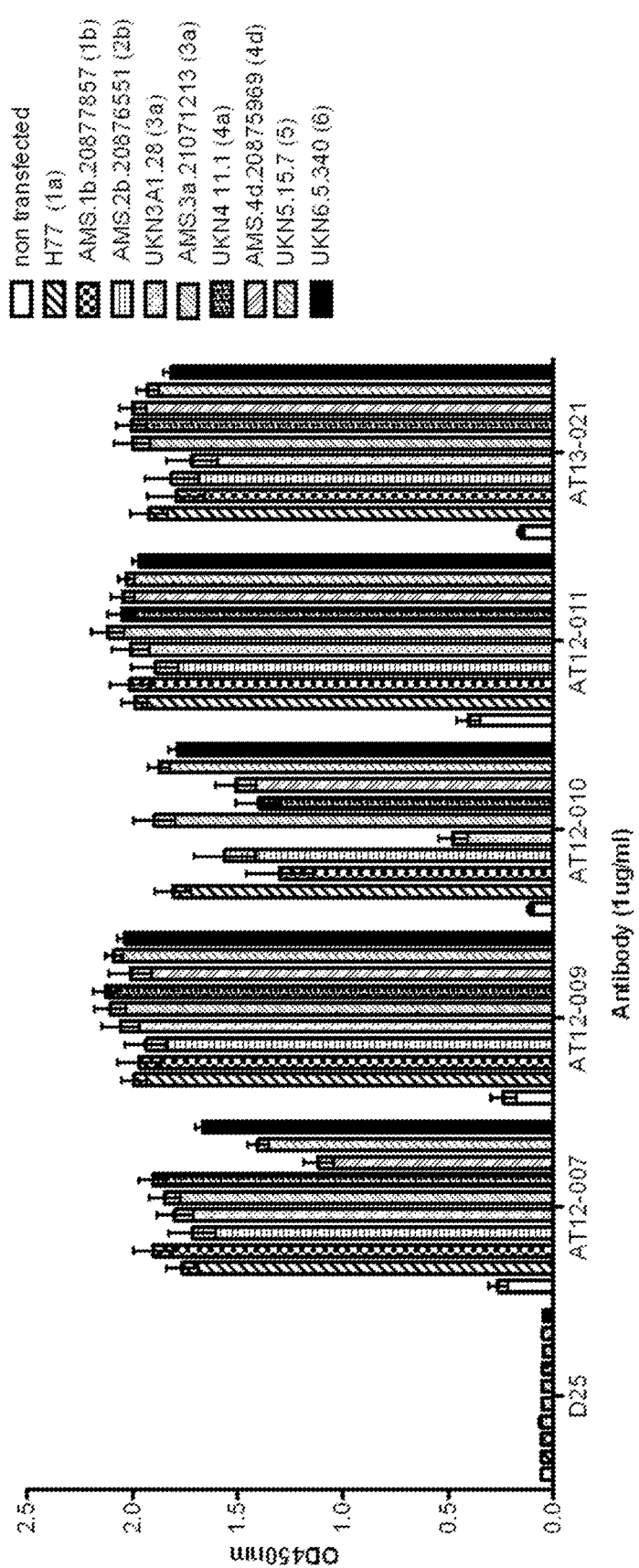

FIG. 2. Antibody binding to E1E2 protein from different HCV genotypes by ELISA.

Cell lysates of 293T cells transfected with different E1E2 constructs were incubated (1:5 diluted) on GNA pre-coated plates before addition of antibodies (1 µg/mL). Next to a lysate of non-transfected 293T cells, the RSV-F protein specific mAb D25 was used as a negative control. On the Y-axis the mean optical density (OD450 nm) is depicted and the standard errors of the means (SEM) is included. The E1E2 sequences are indicated between brackets and the assay was performed in duplicate and repeated twice.

Figure 3:
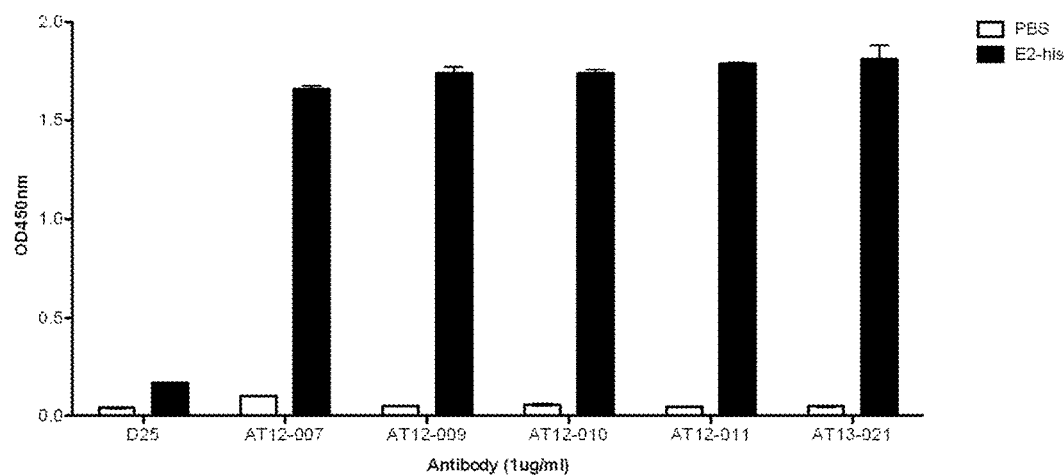

FIG. 3. Antibody binding to soluble E2 protein determined by ELISA.

The antibodies were added to E2-his6-ST pre-coated wells at 1 µg/mL. PBS treated and the RSV-F protein specific mAb D25 were used as negative controls. On the Y-axis the mean optical density (OD450 nm) is depicted and the standard errors of the means (SEM) is included. The assay was performed in duplicate and performed twice.

Figure 4:
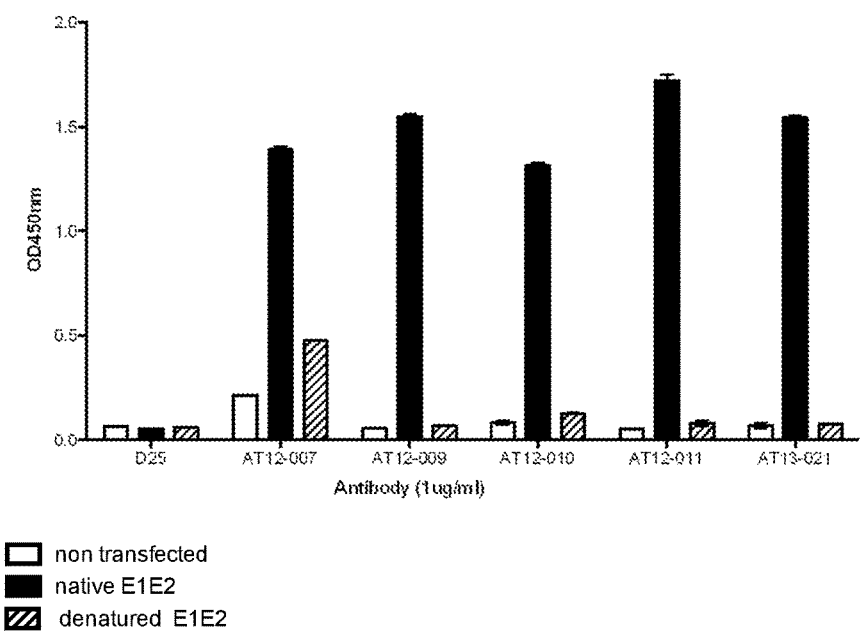

FIG. 4. Antibody binding to denatured E1E2 protein determined by ELISA.

Cell lysate containing H77 derived E1E2 was denatured with DTT and SDS and added (diluted 1:5) to GNA pre-coated plates before the antibodies were added at 1 µg/mL. Non-transfected cell lysate was used as a control for non-E1E2 specific binding and native E1E2 lysate as positive control for the binding of antibodies. The RSV-F protein specific mAb D25 was used as negative control. On the Y-axis the mean optical density (OD450 nm) is depicted and the standard errors of the means (SEM) is included. The assay was performed in duplicate and performed twice.

Figure 5:
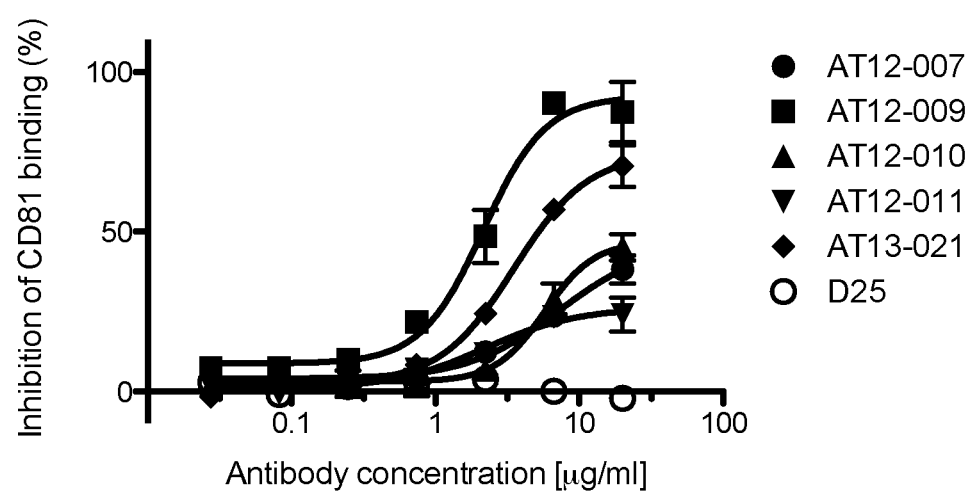

FIG. 5. Inhibition of CD81 binding to E1E2 protein by antibodies.

E1E2 transfected 293T cells were pre-incubated with different concentrations of antibody before CD81-LEL was added. D25 was used as negative control. The y-axis indicates the percentage of CD81 binding inhibition and the errors bars represent one standard error of the mean (SEM). The assay was performed in duplicate and repeated in one separate experiment.

Figure 6:
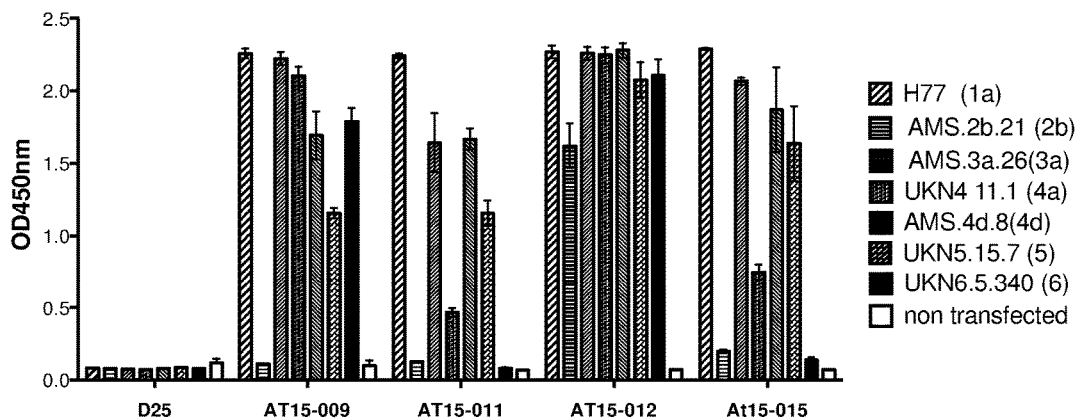

FIG. 6. Antibody binding to E1E2 proteins from different HCV genotypes by ELISA.

Cell lysates of 293T/17 cells transfected with different E1E2 constructs were incubated (1:5 diluted) on GNA pre-coated plates before addition of B cell supernatant containing antibodies (0.2n/mL). Next to a lysate of non-transfected 293T/17 cells, the RSV-F protein specific mAb D25 was used as a negative control. On the Y-axis the mean optical density (OD450 nm) is depicted and the standard deviation (SD) is included. The E1E2 sequences are indicated between brackets and the assay was performed in duplicate.

Figure 7:
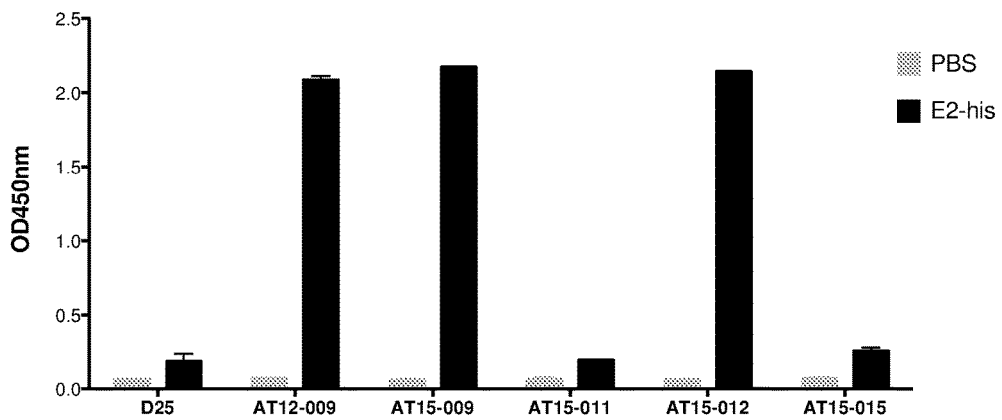

FIG. 7. Antibody binding to soluble E2 protein determined by ELISA.

Supernatants from B cell cultures containing antibodies were added to E2-his6-ST pre-coated wells. PBS treated wells and the RSV-F protein specific mAb D25 were used as negative controls. On the Y-axis the mean OD450 nm is depicted and the SD is included. The assay was performed in duplicate.

Figures 8, 9:
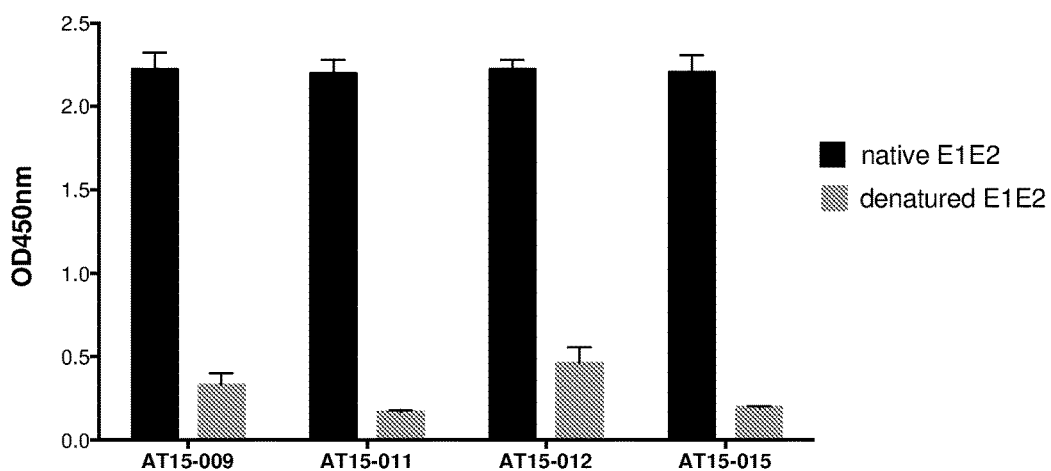

FIG. 8. Antibody binding to denatured E1E2 proteins determined by ELISA.

A cell lysate from 293T/17 cells transfected with H77 derived E1E2 was denatured with DTT and SDS and added (diluted 1:5) to GNA pre-coated plates before the B cell supernatants containing antibodies were added. Native E1E2 lysate was used as positive control for antibody binding. The RSV-F protein specific mAb D25 was used as negative control. On the Y-axis the mean OD450 nm is depicted and the SD is included. The assay was performed in duplicate.

FIG. 9. Amino acid sequence of the E1 protein (corresponding to residues 192-383 of the HCV polyprotein) from HCV genotype 1a, strain H77 (Genbank accession number AAB67037) (SEQ ID NO: 147).

EXAMPLES

Example 1

Materials and Methods

Cells and Plasmids

293T/17 and Huh-7 cells were maintained in Dulbecco's modified essential medium (DMEM, Invitrogen) supplemented with 8% fetal bovine serum (FBS). To generate HCV pseudotyped particles (HCVpp) we transfected 293T/17 cells with 3 plasmids:

i) pcDNA3.1 or pcDNA3.3 vector (Invitrogen) expressing E1E2 of isolate H77 (Genbank accession no AAB67037, with three amino acid changes; R564C, V566A, and G650E, Albecka, 2011 Journal of virology) or patient derived E1E2 sequences ii) the phCMV vector containing gag/pol and iii) the phCMV vector containing the Luciferase gene.

Isolation of cDNA Encoding E1E2 from Patients

HCV RNA from patients infected with different genotypes of HCV was isolated from stored patient plasma using the Boom extraction method (Boom et al. 1990) and cDNA was synthesized by random hexamer priming. The region containing the C-terminal part of Core (the signal sequence for ER targeting of E1), E1 and E2 was amplified with specific primers. Subsequently, the polymerase chain reaction (PCR) product was cloned into pcDNA3.3 using the TOPO PCR cloning kit (Invitrogen). All sequences were confirmed by Sanger sequencing.

Cloning of Published E1E2 Sequences

E1E2 sequences for the isolates UKN3A 1.28 (Genbank accession no. AY734984), UKN4.11.1 (Genbank accession no. AY7349986), UKN6.5.340 (Genbank accession no. AY736194) and UKN5.15.7 (Genbank accession no. EF427672) (Lavillette, 2005, Hepatology; Johansson, 2007, PNAS) were synthetized by GeneArt (Invitrogen). Subsequently, they were cloned into the pcDNA3.1 vector (Invitrogen).

Production of Soluble E2-His6-Sortase Tag

The sequences of the E2 ectodomain (corresponding to residues 384-717 of the polyprotein) from isolate H77 (sequence in FIG. 1) and isolate AMS.2b.20876551.kloon21 (sequence in FIG. 1) (SEQ ID NO: 146) were amplified by PCR before being cloned into the pCPEO-His6-ST expression vector. To produce the soluble E2, 293T/17 cells were transiently transfected with the expression plasmid using XtremeGENE 9 (Roche). After harvest of the culture supernatant, the E2-his6-ST was purified using a HisTrap FF column on an ÄKTA Explorer 10s (GE healthcare).

Generation of Immortalized B Cells

Human memory B cells were immortalized using the AIMSelect technology (Kwakkenbos et al. 2010 and Kwakkenbos et al. 2013). In brief, human CD27+IgG+ memory B cells were isolated from peripheral blood mononuclear cells of donors who spontaneously cleared a HCV infection. After stimulation with CD40L and interleukin (IL)-21, the cells were transduced with a retroviral vector containing the transgenes BCL6, Bcl-xL and the marker gene GFP. Transduced B cells were maintained in culture with irradiated CD40 Ligand expressing L-cells and recombinant mouse IL-21. The transduced B cells resemble germinal center B cells. They are characterized by the surface expression of the immunoglobulin (the B Cell Receptor (BCR)) and secrete immunoglobulin into the culture supernatant. HCV specific B cells were discovered by directly staining and FACS sorting of fluorescently labeled E2 specific B cells and/or by screening antibodies present in supernatant of B cells cultured in serial dilution for binding to 293T cells expressing E1 and E2.

Isolation of Cross-Binding Antibodies

To isolate B cells secreting E1E2 specific antibodies, two approaches were used.

i) Bcl6 and Bcl-xL transduced polyclonal B cells were seeded at 100 cells per well and maintained in culture for 2 to 3 weeks. The supernatants of B cell cultures were screened for binding to 293T cells expressing E1E2 genotype 1a isolate H77 by flow cytometry. Cultures that showed reactivity to E1E2 were sorted single cell using the FACSAria instrument (BD) in order to obtain monoclonal B cell cultures. To retrieve the positive monoclonal B cell cultures, culture supernatants were screened after 3 weeks for binding to 293T cells E1E2 of H77 by flow cytometry. Positive supernatants were tested for binding to cells transfected with E1E2 from different genotypes by flow cytometry. Subsequently, the antibody variable heavy (VH) and light (VL) chain sequences from these B cell clones were obtained.

ii) Bcl6 and Bcl-xL total transduced B cells were incubated with the soluble E2-his6-sortase tag (ST) from isolate AMS.2b.20876551.kloon21 (genotype 2b). B cells recognizing E2-his6-ST (detected with an anti-his antibody) were sorted by FACSAria and maintained in culture for 2 weeks. These E2 sorted B cells were further enriched for HCV E2 specificity by another round of single cell sorting using soluble E2-his6-ST from isolate H77 (genotype 1a). The latter sorting strategy results in selection of B cells recognizing E2 from genotypes 1 and 2. The sorted B cells were maintained in culture for 3 weeks before the culture supernatants were screened for E2-his6-ST binding by enzyme-linked immunosorbent assay (ELISA). Supernatants that showed reactivity were tested for binding to E1E2 cell lysates by ELISA and HCVpp neutralization. Finally, the VH and VL sequences from B cell clones that showed persistent broad reactivity were obtained.

Flow Cytometry

To test the binding of the B cell supernatants to the HCV envelope glycoproteins E1 and E2 or E2 only, 293T cells were transfected with an E1E2 expression plasmid using X-tremeGENE 9 (Roche). Two days after transfection, the cells were fixed with 4% paraformaldehyde (PFA) and frozen in FBS+10% DMSO at −80° C. Immediately after thawing, the transfected cells were permeabilized with Perm/wash Buffer (BD) for 15 min at 4° C. before being incubated with IgG containing B cell supernatants for 30 min at 4° C. After three wash steps with perm/wash buffer the cells were incubated with goat anti human IgG-PE (Southern biotech) for 30 min at 4° C. After washing, the cells were re-suspended in 4% PFA solution. Fluorescence was measured using Guava EasyCyte (Millipore). Non-transfected GFP expressing 293T/17 cells were used as control for non-E1E2 specific binding and unstained cells were used as negative control.

To determine whether the antibodies interfere with binding of CD81 to E1E2; E1E2 transfected cells were pre-incubated with the antibodies before the large extracellular loop (LEL) of CD81 (Sino Biological; 0.1 μg/mL) was added. Since the CD81 peptide is expressed on a mouse Fc tail, intracellular binding of CD81 was detected using an alexa647 conjugated anti-mouse Fc antibody (Jackson ImmunoResearch). After washing, the cells were re-suspended in 4% PFA solution. Fluorescence was measured using the FACS canto (BD Biosciences). The level of inhibition are calculated by dividing the percentage of Alexa 647 positive cells from each well by the mean percentage of Alexa 647 positive cells from wells where the cells were incubated without antibody. D25, a Respiratory Syncytial Virus F protein specific antibody was used as negative control.

E2 Specific Cell Sorting

To sort E2 specific B cells, cells were incubated with soluble E2-his (1 μg/mL) for 1 hour at 4° C. The cells were washed three times with Iscove's Modified Dulbecco's Media (IMDM) containing 8% FBS (wash buffer) before being incubated with anti his antibody Alexa 647 (Qiagen) for 30 min at 4° C. After washing the cells three times with wash buffer, the fluorescence was measured and the positive cells were sorted using FACSAria (BD). Cells from a HCV naive patient was used as negative control.

ELISA

To test the binding of antibodies and antibodies in B cell supernatants to soluble E2, plates were coated with E2-his6-ST (5 μg/mL) overnight at 4° C. After washing with Phosphate buffered saline (PBS), the plates were blocked with 1% fish skin gelatin (Sigma) for 1 hour at room temperature. After incubation the plates were washed 5 times with PBS containing 0.05% tween (PBS-T). To detect bound antibodies, the plates were incubated with HRP conjugated anti-human IgG (Jackson) for 1 hour at room temperature. After washing, bound antibodies were detected using 3,3',5,5' tetramethyl benzidine (TMB) and the reaction was stopped using H2SO4. Optical density (OD) at 450 nm was measured with an EnVision Multilabel Reader (PerkinElmer). PBS coated wells were used as control for non-specific binding and D25 an RSV-F specific antibody was used as negative control.

To study antibody specificity across different HCV genotypes, 293T/17 cells were transfected with E1E2 expression plasmid using XtremeGENE 9 (Roche). Two days after transfection, the cells were lysed with 1% triton (Sigma). The cell lysate was clarified and frozen at −80° C. To prepare the ELISA plate, G. nivalis (GNA) lectin (Sigma) was coated at 5 μg/mL and after washing with PBS, the plate was blocked with 1% fish skin gelatin (Sigma) for 1 hour at room temperature. The plate was emptied before the E1E2 containing cell lysate (1:5 diluted in blocking buffer) was added for 1 hour at room temperature. After 5 washes with PBS-T, the antibody solutions or antibodies from B-cell supernatant were incubated for 1 hour at room temperature. The plate was washed 5 times with PBS-T and HRP-conjugated anti-human IgG antibody (Jackson) was incubated for 1 hour at room temperature. After washing, bound antibodies were detected using TMB substrate buffer and the reaction was stopped using $H_2SO_4$. OD450 nm was measured using an EnVision® Multilabel Reader (PerkinElmer). Lysate from non-transfected 293T/17 cells was used as control for non-E1E2 specific binding and D25 was used as negative control.

To determine if antibodies recognize continuous or discontinuous epitopes, E1 and E2 were denatured by incubating E1E2 cell lysate with 0.4% sodium dodecyl sulfate and 20 mM dithiotreitol at 75° C. After 15 min, the lysate was diluted 5 times before being added to GNA lectin coated wells. The subsequent steps of the assay were performed in a similar fashion as described above.

To determine which amino acids of E2 are crucial for antibody binding, E1E2 sequences of HCV isolate H77 were synthetized with single alanine mutations. The E2 mutants were designated X123Y, where 123 is the residue position, X indicates the amino acid in H77 sequence and Y indicates the replacing amino acid. For the positions N415, S424, L441, F442, Y443, Y485, Y527, W529, G530, D535 and W616, E1E2 sequences of HCV isolate H77 were synthetized with single alanine mutations by GeneArt (Invitrogen) and cloned into pcDNA3.1. For the positions T435, G436, A439, T526, R657 and D698, single alanine mutations were introduced in the E1E2 H77 sequence using primers coding the specific mutation (Biolegio) and by use of the QuickChange II XL Site-Directed Mutagenesis Kit (Agilent) according the manufacturer's protocol. Subsequently, the PCR product was cloned into pcDNA3.3 using the TOPO PCR cloning kit (Invitrogen). All sequences were confirmed by Sanger sequencing. If the residue to change was an alanine, it was substituted by a glycine.

The 1:5 diluted lysate of 293T cells transfected with the different E1E2 alanine mutants, were added to GNA lectin coated plates before antibodies were added in a dilution range of 1000 to 0.2 ng/mL. The lysate preparation and ELISA were performed in a similar fashion as described before. Antibody binding to E1E2 alanine mutants was compared to the wild type E1E2. Antibody concentration to achieve 50% binding (EC50) in µg/mL was determined using non-linear regression analysis (Prism software). The relative binding of an antibody was calculated by dividing the EC50 obtained against the wild type vs the alanine protein mutant. The assay was performed in duplicate and repeated at least once.

Cloning and Production of Selected Antibodies

To obtain antibody VH and VL chain sequences total RNA was isolated with TriPure RNA extraction buffer (Roche) and cDNA was generated using SuperScript III reverse transcriptase (Invitrogen). The antibody VH and VL regions were amplified by PCR and sequences analyzed using the cognate forward and reverse primers. Subsequently the variable regions were cloned in frame between a secretion leader sequence and the human IgG1 and kappa constant regions into a pcDNA3.1 (Invitrogen) based vector. To produce recombinant antibodies the VH and VL vectors were transiently transfected into 293T/17 cells. Recombinant antibodies were purified from culture supernatant using a MabSelect Sure column on an ÄKTA Explorer 10s (GE healthcare).

HCV Neutralization Assay

To study the neutralization capacity of the newly discovered antibodies, HCVpp was produced in 293T/17 cells by co-transfecting plasmids (vector containing E1E2 sequence, phCMV-gag/pol and phCMV-Luciferase) in ratio 1:2:2. After 2 days, the culture supernatants containing HCVpp were harvested and incubated with serial antibody dilutions (from 50 µg/mL to 0.0008 µg/mL) for 1 hour at 37° C. The antibody/HCVpp mixture was added to Huh-7 cells and spin-inoculated for 45 minutes at 2000 g. After 3 days, the huh-7 cells were lysed using Bright Glo luciferase kit (Promega). The luciferase activity was measured using an EnVision Multilabel Reader (PerkinElmer).

To determine the background of the assay, 293T cells were transfected only with phCMV-gag/pol and phCMV-Luciferase. HCVpp supernatants that generated luciferase signals 10 times higher compared to the background were used. Of the relative light value of each well, the background was first subtracted. Then the percentage of neutralization was calculated by dividing the relative light units of each well by the mean of relative light units from wells incubated with HCVpp supernatant only. Antibody concentrations to achieve 50% neutralization (IC50) and antibody concentration to achieve 90% neutralization (IC90) in µg/mL were determined using nonlinear regression analysis. VSV-G (vesicular stomatitis virus G protein) pp was used as a positive control and D25 was used as a negative control. The assay was performed in triplicate.

SPR Analysis

Surface plasma resonance (SPR) analysis was performed on an IBIS MX96 SPR imaging system (IBIS Technologies BV) as described (Lokate et al. 2007). In short, one SPR analysis cycle consists of one (or more) injection steps in which analytes are flushed over a sensor that is coated with different ligands (i.e. antibodies). This is followed by a regeneration step in which any bound analyte is removed from the sensor. Multiple cycles can be performed in one experiment. Data was analyzed using Sprint software (version 1.6.8.0, IBIS Technologies BV).

To determine the affinity of the antibodies for ectodomain of HCV envelope glycoprotein E2, the SPR sensor was coated with anti-HCV antibodies on an amine-specific EasySpot gold-film gel-type SPR-chip (Ssens BV) by spotting them on the sensor surface using a continuous flow microspotter device (Wasatch Microfluidics) in coupling buffer (10 mM MES-NaOH, pH 4.5+0.05% Tween20). After spotting for 40 minutes the sensor was deactivated with 0.1 M ethanolamine, pH 8.5 and washed three times with system buffer (PBS+0.05% Tween20+0.05% NaN3). Before starting the analysis, the coupled sensor was briefly washed with regeneration buffer (10 mM glycine-HCl, pH 2), followed by three wash steps with system buffer. Then, the sensor was injected with a concentration series of soluble HCV E2-his (isolate H77 or isolate AMS.2b.20876551.kloon21) ranging from 0.1 to 1.6 µg/ml, diluted in system buffer and incubated for 10 minutes to measure binding kinetics. To measure complex dissociation the sensor was washed with system buffer and incubated for 15 minutes. $K_D$ was calculated as kd/ka. The assay was performed in triplicate and repeated in one separate experiment.

To determine if the antibodies recognize an identical region on E2, SPR assay was performed in a similar fashion as described above. After the injection of soluble E2-his6-ST (isolate H77), the chip was incubated with another antibody for 15 min to measure association, briefly washed with system buffer to remove unbound E2 and then incubated for another 15 min to measure complex dissociation.

Results

Isolation of E1E2 Specific Monoclonal Antibodies

PBMC (70E6 cells) were obtained from a donor who spontaneously cleared a HCV infection. CD27+IgG+ memory B cells were isolated (8.4E5 cells) and immortalized using the AIMSelect technology. Immortalized B cells secrete antibodies and express surface immunoglobulin.

To isolate B cells secreting E1E2 specific antibodies, two approaches were used. The first approach was based on screening of B cell supernatants for binding to E1E2 transfected cells. Immortalized polyclonal B cells (7.7E05 cells) were seeded at 100 cells per well and tested for binding to 293T cells expressing H77 derived E1E2 by flow cytometry, Eleven B cell cultures were selected for single cell sorting to obtain monoclonal B cell cultures. Monoclonal B cell cultures that again recognized H77 derived E1E2 expressed in 293T cells were isolated from 6 cultures and sequenced. Subsequently, the binding of these monoclonal B cell cultures to a panel of E1E2 derived from different genotypes 1a (H77), 1b (AMS.1b.20877857), 2b (AMS.2b.20876551.kloon21), 3a (UKN3A 1.28 and AMS.3a.21071213), 4 (UKN4.11.1), 4d (AMS.4d.20875969) was tested by ELISA. Two of the antibodies showed binding only to E1E2 derived from genotype 1a whereas the four other supernatants showed binding to E1E2 derived from genotypes 1, 2, 3 and 4. In total four different cross-genotype HCV E1E2 antibodies were isolated using this strategy.

In Parallel, B Cells Directly Recognizing Fluorescent Labelled E2

(AMS.2b.20876551.kloon21, genotype 2b) were sorted, cultured and in a second round of sorting, cells were retrieved that recognized soluble E2-his from isolate H77 (genotype 1a) in order to get for B cells specific for at least genotype 1 and 2. Culture supernatants of these selected B cells (approximately 672 cells) were screened for E2 binding bodies to E2 (to exclude binding to E1) was determined by ELISA using soluble recombinant E2 from isolate H77 (FIG. 3), it was found that all five antibodies were directed against an epitope present on soluble E2. Furthermore we found that all antibodies recognize a non-linear, discontinuous epitope (FIG. 4). This was determined by testing the antibodies (1 μg/mL) in ELISA to native and denatured H77 derived E1E2 derived from transfected 293T cell lysate. The denatured E1E2 proteins were obtained by DTT and SDS treatment.

Finally, as shown in Table 2, we determined the affinity (KD) of the antibodies for E2 from isolate H77 (genotype 1a) and isolate AMS.2b.20876551.kloon21 (genotype 2b). Of all antibodies tested AT12-011 showed the highest affinity for E2, namely 0.3 nM for genotype 1 and 0.2 nM for genotype 2b. AT12-009 bound E2 genotype 1 and E2 genotype 2b with similar affinities of 1.3 nM and 2.3 nM, respectively. AT12-010 bound E2 genotype 1 and E2 genotype 2b at 39.3 nM and 22.8 nM, respectively. In contrast to AT12-009 and AT12-011, AT12-007 and AT13-021 showed enhanced binding to E2 genotype 2 (3.8 nM and 2 nM for AT12-007 and AT13-021, respectively) compared to binding of AT12-007 (44 nM) and AT13-021 (14 nM) to E2 from genotype 1.

TABLE 2

Affinity of the antibodies for E2. The binding kinetics of the antibodies were measured for E2 from isolate H77 (genotype 1a) and isolate AMS.2b.20876551.clone21 (genotype 2b) by direct SPR. Means of KD are shown (+/− variance).

| | E2 genotype 1a | | | E2 genotype 2b | | |
|---|---|---|---|---|---|---|
| Antibody | $K_a$ ($10^{-5}$ s$^{-1}$ M$^{-1}$) | $K_d$ ($10^{-5}$ S$^{-1}$) | $K_D$ (nM) | $K_a$ ($10^{-5}$ s$^{-1}$ M$^{-1}$) | $K_d$ ($10^{-5}$ s$^{-1}$) | $K_D$ (nM) |
| AT12-007 | 4.6 (±0.9) | 184 (±31) | 44 (±16) | 5.0 (±0.3) | 19 (±0.6) | 3.8 (±0.1) |
| AT12-009 | 8.6 (±0.8) | 11 (±1.6) | 1.3 (±0.3) | 8.9 (±1.6) | 20 (±1.5) | 2.3 (±0.5) |
| AT12-010 | 3.6 (±0.5) | 142 (±43) | 39.3 (±6.4) | 4.6 (±1.2) | 98 (±4.2) | 22.8 (±4.2) |
| AT12-011 | 13.6 (±3.9) | 3.9 (±1.7) | 0.3 (±0.1) | 8.8 (±3.4) | 1.1 (±0.5) | 0.2 (±0.1) |
| AT13-021 | 2.9 (±0.6) | 36 (±8.9) | 14.2 (±6.2) | 5.3 (±0.4) | 10 (±0.3) | 2.0 (±0.1) | by ELISA and were tested for binding to E1E2 cell lysates of different genotypes by ELISA and for neutralization potency. VH VL sequencing of several clones revealed 2 distinct sequences. One antibody sequence was unique compared to the sequences obtained from the first screening strategy.

Together, the two screenings methods resulted in the selection of 5 unique E2 specific clones that show broad binding and neutralization.

The variable regions VH and VL of the five cross-genotype antibodies were cloned into a vector containing the human IgG1 and kappa constant regions to produce recombinant antibodies.

Binding Properties

To study binding properties of the selected antibodies AT12-007, AT12-009, AT12-010, AT12-011 and AT13-021, the recombinant antibodies were first tested for binding at 1 μg/mL to a panel of E1E2 derived from six different genotypes 1a (H77), 1b (AMS.1b.20877857), 2b (AMS.2b.20876551.kloon21), 3a (UKN3A 1.28 and AMS.3a.21071213), 4 (UKN4.11.1), 4d (AMS.4d.20875969), 5 (UKN5.15.7) and 6 (UKN6.5.340) by ELISA. An antibody was considered specific for E1E2 when the optical density (OD) at 450 nm was three times the standard deviation compared to the background OD on non-transfected cell lysate. All recombinant antibodies showed binding to the E1E2 from all genotypes tested (FIG. 2). In addition when the binding of the recombinant anti- Epitope Mapping To identify the region of E2 recognized by the antibodies, SPR competition experiments were performed using E2-his from isolate 1177. After the primary antibody was immobilized on chip and bound to E2, the secondary antibody was injected. When no signal was obtained with the secondary antibody this suggested that both antibodies recognized an identical epitope or at least an epitope in close proximity. As shown in table 3, AT12-007, AT12-009, AT12-010 and AT13-021 compete for binding. In contrast, AT12-011 did not compete for binding with any other antibody, which indicates that AT12-011 binds a different non-linear domain on E2 than antibodies AT12-007, AT12-009, AT12-010 and AT13-021.

TABLE 3

Antibody competition assay for binding to E2 by SPR. The competition assay was performed by SPR using E2-his6-ST from isolate H77 (genotype 1a).

| | | Immobilized Antibody | | | | |
|---|---|---|---|---|---|---|
| | | AT12-007 | AT12-009 | AT12-010 | AT12-011 | AT13-021 |
| Injected Antibody | AT12-007 | N | N | N | Y | N |
| | AT12-009 | N | N | N | Y | N |
| | AT12-007 | N | N | N | Y | N |

TABLE 3-continued

Antibody competition assay for binding to E2 by SPR. The competition assay was performed by SPR using E2-his6-ST from isolate H77 (genotype 1a).

| | Immobilized Antibody | | | | |
|---|---|---|---|---|---|
| | AT12-007 | AT12-009 | AT12-010 | AT12-011 | AT13-021 |
| AT12-010 | Y | Y | Y | N | Y |
| AT13-021 | N | N | N | Y | N |

Categories indicated with "N": no binding of secondary antibody (competition); categories indicated with "Y": binding of secondary antibody (no competition).

To determine which amino acid residues in E2 are important for binding of our antibody panel, we generated a panel of H77 E2 alanine mutants, which have been shown to affect binding of known neutralizing antibodies. Antibody binding was determined by ELISA using E1E2 transfected 293T cell lysates. Table 4 presents the ratio of antibody binding to E2 mutants compared the binding to the wild-type protein. As could be expected from the competition results (table 3), AT12-007, AT12-009, AT12-010 and AT13-021 share an antigen binding domain on E2 that is at least composed of the residues F442A, Y527A, W529A, G530A, D535A, W616A since mutation of these residues resulted in ≤25% binding. Alanine substitutions of the residues S424A, T435A, G436A, L441A, Y443A and T526A, decreased (sometimes partially) binding of some or all antibodies. However, none of the alanine mutations affected binding of AT12-011. Suggesting that the binding domain of AT12-011 is completely different compared to the antibodies AR3, AR4A, AR5A, HC-1, HC-11, CBH-2, CBH-5, HC84, e20 and e137 as described in literature (Law et al. Nature Medicine, 2007; Giang et al., PNAS, 2012: Owsianka et al, Journal of general virology, 2008; Keck et al, Journal of virology, 2011: Keck et al, Plos pathogens, 2012; Perotti et al, Journal of virology, 2008; Mancini et al, plos one, 2009).

TABLE 4

Epitope mapping of the antibodies.
The binding of antibodies to E2 alanine-mutants was tested by ELISA. Shown is the relative antibody binding to the mutant sequences compared the wild type sequence. When the EC50 could not be calculated because of very weak binding this is indicated by <10%.

| | AT12-007 | AT12-009 | AT12-010 | AT12-011 | AT13-021 |
|---|---|---|---|---|---|
| N415A | 115% | 104% | 117% | 82% | 119% |
| S424A | 34% | 25% | 16% | 114% | 17% |
| T435A | 84% | 85% | 47% | 118% | 21% |
| G436A | 35% | 51% | <10% | 103% | <10% |
| A439G | 67% | 71% | 45% | 108% | 53% |
| L441A | <10% | 32% | <10% | 110% | 7% |
| F442A | <10% | 18% | <10% | 107% | 9% |
| Y443A | <10% | 64% | <10% | 105% | 87% |
| Y485A | 114% | 111% | 107% | 98% | 114% |
| T526A | 31% | 35% | 29% | 116% | 27% |
| Y527A | 24% | 23% | 19% | 121% | 21% |
| W529A | <10% | 18% | <10% | 120% | 13% |
| G530A | <10% | 6% | <10% | 108% | <10% |
| D535A | 15% | 5% | 5% | 118% | <10% |
| W616A | <10% | 20% | <10% | 125% | <10% |
| R657A | 116% | 104% | 99% | 100% | 88% |
| D698A | 103% | 98% | 86% | 87% | 80% |

Antibody Neutralization of HCVpp

To study neutralizing capacity of the antibodies, HCVpp from isolates H77 (gt 1a), AMS.1b.20877857 (gt 1b), AMS.2b.20876551.kloon21 (gt 2b), AMS.3a.21071213 (gt 3a), UKN4.11.1 (gt 4) and AMS.4d.20875969 (gt4d) were generated. The supernatants containing HCVpp were incubated with antibodies ranging from 50 μg/mL to 0.0008 μg/mL before being added on Huh-7 cells. 50% and 90% inhibitory concentrations (IC) neutralization values are shown in Table 5. Potency of the antibodies varied between genotypes. AT12-009 and AT13-021 neutralized all HCVpp within an IC50 range of 1 to 940 ng/ml, while AT12-007, AT12-010 and AT12-011 showed a more restricted neutralization. AT12-007 and AT12-010 neutralized all HCVpp tested except genotype 4d or 4a and 4d respectively. AT12-011 which showed the highest affinity of all antibodies neutralized HCVpp from genotype 1a, 1b and 2b.

TABLE 5

Neutralization of HCVpp expressing different genotypes.
Antibody IC50 and IC90 inhibitory concentrations in μg/mL.

| | | AT12-007 | | AT12-009 | | AT12-010 | | AT12-011 | | AT13-021 | |
|---|---|---|---|---|---|---|---|---|---|---|---|
| Isolate | Genotype | IC50 | IC90 | IC50 | IC90 | IC50 | IC90 | IC50 | IC90 | IC50 | IC90 |
| H77 | 1a | 2.67 | >50 | 0.07 | 7.85 | 1.06 | >50 | 4.41 | >50 | 0.30 | 9.98 |
| AMS.1b.20877857.kloon2 | 1b | 0.04 | 0.50 | 0.001 | 0.13 | 0.47 | 8.51 | 4.31 | >50 | 0.09 | 5.67 |
| AMS.2b.20876551.kloon21 | 2b | 0.26 | 9.41 | 0.06 | 6.17 | 0.61 | 20.4 | 27.5 | >50 | 0.12 | 8.84 |
| AMS.3a.21071213.kloon26 | 3a | 1.42 | 21.74 | 0.14 | 5.34 | 1.41 | >50 | >50 | >50 | 0.25 | 12.3 |
| UKN4 11.1 | 4a | 1.87 | >50 | 0.19 | 14.1 | >50 | >50 | >50 | >50 | 0.94 | 13.9 |
| AMS.4d.20875969.kloon8 | 4d | >50 | >50 | 0.72 | 47.4 | >50 | >50 | >50 | >50 | 0.94 | >50 |

Antibody Inhibition of CD81 Binding to E1E2 Protein

HCV E1E2 interacts with the Large Extracellular Loop (LEL) of CD81 on the target cell. To determine if the antibodies interfere with CD81 binding, we used a CD81 competition assay by flow cytometry. E1E2 transfected cells were pre-incubated with different concentrations of antibody before CD81-LEL was added and detected. The reduction in CD81 binding by the antibodies ranged from 10 μg/mL to 0.03 μg/mL (FIG. 5). Interestingly, all antibodies interfered with CD81 binding to E1E2 although potencies differed between antibodies. As for the neutralization assay, AT12-009 and AT13-021 were the most potent with IC50 values of between 1 and 10 μg/mL.

Example 2

Materials and Methods

Cells and Plasmids

Freestyle™ 293-F cells were maintained in Freestyle Medium (Invitrogen) whereas 293T/17 and Huh-7 cells were maintained in Dulbecco's modified essential medium (DMEM, Invitrogen) supplemented with 8% fetal bovine serum (FBS). To generate HCV pseudotyped particles (HCVpp) we transfected 293T/17 cells with 3 plasmids:
i) pcDNA3.1 or pcDNA3.3 vector (Invitrogen) expressing E1E2 of isolate H77 (Genbank accession no AAB67037, with three amino acid changes; R564C, V566A, and G650E, Albecka, 2011 Journal of virology) or patient derived E1E2 sequences
ii) the phCMV vector containing gag/pol and iii) the phCMV vector containing the Luciferase gene. E1E2 sequences for the isolates UKN4.11.1 (Genbank accession no. AY7349986), UKN6.5.340 (Genbank accession no. AY736194) and UKN5.15.7 (Genbank accession no. EF427672) (Lavillette, 2005, Hepatology; Johansson, 2007, PNAS) were made as described in example 1 in paragraph "Cloning of published E1E2 sequences". pcDNA3.3 E1E2 AMS.2b.20876551.kloon21 and pcDNA3.3 E1E2 AMS.3a.21071213 were made as described in Example 1 in paragraph "isolation of cDNA encoding E1E2 from patients".

Production of Soluble E2-His6-Sortase Tag

Production of soluble E2-His6-sortase tag was performed as described in Example 1.

Generation of Immortalized B Cells

B Cells were Immortalized in a Similar Fashion as Described in Example 1

The transduced B cells resemble germinal center B cells. They are characterized by the surface expression of the immunoglobulin (the B Cell Receptor (BCR)) and secrete immunoglobulin into the culture supernatant. HCV specific B cells were discovered by screening antibodies present in supernatant of B cells for HCVpp neutralization.

Isolation of HCV Neutralizing Antibodies

Immortalized B cells from donor 130 were seeded 1 cell per well using the FACS Aria III (BD). After 3 weeks of culture, B cell supernatants were tested for neutralization of HCVpp from isolate H77 (genotype 1a). B cell supernatants neutralizing 50% of HCVpp infection in two independent experiments were selected for further experiments. In order to determine the antibody binding epitope antibodies were tested in an ELISA using a cell lysate of Freestyle™ 293-F cells transfected with 12 different E1E2 alanine mutants. In addition, antibody titrations of B cell supernatants were tested for neutralization of HCVpp from isolate H77 (genotype 1a) in order to estimate the potency of the antibodies. Neutralizing B cell cultures and/or antibodies with unique binding properties were selected for sequencing and further experiments.

IgG ELISA

The concentration of antibodies in the B cell supernatant was determined using ELISA. After coating overnight with 5 µg/mL anti human IgG (Jackson), plates were blocked with 1% Fish skin gelatin. After at least 1 hour blocking, titration of purified antibodies or standard antibody (Jackson) were added. HRP conjugated anti-human IgG (Jackson) was used to detect human IgG antibodies. After washing, bound antibodies were detected using TMB and the reaction was stopped using $H_2SO_4$. OD at 450 nm was measured with an EnVision Multilabel Reader (PerkinElmer). Antibody concentrations were determined using nonlinear regression analysis. The mean of antibody concentration from three independent experiments was used.

ELISA

ELISA assays were performed in a similar fashion as described in Example 1. Cell lysates containing E1E2 alanine mutants were produced in a similar fashion as described in Example 1 with the following modifications. E1E2 sequences of HCV isolate H77 were synthetized with single alanine mutations. The E1 E2 mutants were designated XabcY, where abc is the residue position, X indicates the amino acid in H77 sequence and Y indicates the replacing amino acid. For the positions N415, 5424, L441, F442, Y443, Y485, Y527, W529, G530, D535 and W616, E1E2 sequences of HCV isolate H77 were synthetized with single alanine mutations by GeneArt (Invitrogen) and cloned into pcDNA3.1. For the positions N209A, N325A, L413, G418, W420, N423, G436, N448, T526, Y527, N532, D533, T534, V538, P612, P664, P676, T435, G436, A439, T526, R657 and D698, single alanine mutations were introduced in the E1E2 H77 sequence using primers coding the specific mutation (Biolegio) and by use of the QuickChange II XL Site-Directed Mutagenesis Kit (Agilent) according the manufacturer's protocol. Subsequently, the PCR product was cloned into pcDNA3.3 using the TOPO PCR cloning kit (Invitrogen). All sequences were confirmed by Sanger sequencing. If the residue to change was an alanine, it was substituted by a glycine. Freestyle™ 293-F cells cells were transfected with E1E2 expression plasmid using Polyethylenimine (Polysciences). Two days after transfection, cells were lysed with 1% triton (Sigma). The cell lysate was clarified and frozen at −80° C.

HCV Neutralization Assay

HCV neutralization assays were performed in a similar fashion as described in Example 1 with the following modifications. The culture supernatants containing HCVpp were incubated with serial antibody dilutions (from 10 µg/mL to 0.04 µg/mL) or 3 fold serial dilution of B cell supernatants with starting concentration varying between 4 and 1 µg/mL for 1 hour at 37° C. The assay was performed at least in duplicates.

SPR Analysis

SPR affinity measurements were performed in a similar fashion as described in Example 1 with the following major modification. B cell supernatants (containing anti-HCV antibodies) or purified antibody controls are captured on a Gel-type anti-human-IgG-Fc SensEye SPR-chip (Ssens BV) and they were not as described in Example 1 spotted directly on the chip. Prior to capture, B cell supernatants are 1:1 diluted in system buffer (PBS+0.05% Tween20+0.02% sodium azide). After capture has completed, antibody—anti-human-IgG complexes are cross-linked using a Fix-It capture-crosslink kit (Ssens BV).

Results

Isolation of Neutralizing Antibodies

From donor 130, 40,000 memory IgG+CD27+ B cells were isolated and 24,000 cells were immortalized using the AIMSelect™ technology (as described in the Materials & Methods of Examples 1 and 2). Five thousand immortalized B cells from donor 130 were seeded 1 cell per well. After 2 separate HCVpp neutralization assays (isolate 1177), 66 B cell supernatants that could neutralize HCV H77≥50% were selected and further tested in ELISA using cell lysates of E1E2 alanine mutants and the potency of these supernatants was retested in a HCVpp H77 neutralization assay. Thirteen monoclonal B cell cultures originally showed equal to better neutralization compared to AT12-009. When studying the binding pattern on the E1E2 alanine mutants, we found 6 clones that were not affected by any of the mutations and a relatively large panel that was epitope II binding only. By sequencing of these cultures, 4 different antibody sequences (AT15-009, AT15-011, AT15-012 and AT15-015) were identified. The heavy and light chain CDR and variable region sequences of these antibodies are depicted in Table 1.

Binding Properties

To study binding properties of the selected antibodies AT15-009, AT15-011, AT15-012 and AT15-015, B cell culture supernatant containing antibodies were first tested for binding to E1E2 from six different genotypes: 1a (H77), 2b (AMS.2b.20876551.kloon21), 3a (AMS.3a.21071213), 4 (UKN4.11.1), 4d (AMS.4d.20875969), 5 (UKN5.15.7) and 6 (UKN6.5.340) by ELISA at 0.2 µg/mL. An antibody was considered specific for E1E2 when the OD at 450 nm was three times the background compared to the OD of a lysate of non-transfected 293T/17 cells. AT15-012 recognized E1E2 from all genotypes (FIG. 6), while AT15-009, AT15-011 and AT15-015 showed binding to the E1E2 from genotype 1, 3, 4 and 5. In addition to those genotypes, AT15-009 also recognized E1E2 from genotype 6. When the binding of the B cell supernatant to E2 (to exclude binding to E1) was determined by ELISA using soluble recombinant E2 from isolate H77 (FIG. 7), it was found that AT15-009 and AT15-012 recognize an epitope present on soluble E2 whereas the epitope of AT15-011 and AT15-015 is only present in the E1E2 protein complex and is not on soluble E2. Furthermore we found that all antibodies recognize a non-linear, discontinous epitope on E1E2 (FIG. 8). This was determined by testing the B cell supernatant (1 µg/mL) in ELISA to native and denatured H77 derived E1E2 derived from transfected 293T/17 cell lysate. To denature the E1E2 proteins the sample was treated with DTT and SDS.

We determined the affinity ($K_D$) of the antibodies for E2 from isolate H77 (genotype 1a)(Table 6). AT15-012 showed the highest affinity for E2, namely 0.015 nM whereas we measured an affinity of 0.242 nM for AT15-009. As can be seen for antibodies AT12-009 and AT12-011, the $K_D$ values measured in this Example differ from the $K_D$ values measured in Example 1. This is due to differences in the experimental set up between the two Examples. In Example 1, purified antibodies are directly immobilized on the chip; in this experiment, non-purified antibodies are captured, directly from B cell supernatant, on an anti-human-IgG-Fc coated chip and then immobilized. In the latter setup, all antibodies are immobilized in the same orientation, and possibly with a higher antibody density. Antibody orientation and density influence the observed binding kinetics (Schasfoort et al., 2012), and this could be the cause for deviations in observed affinity between Example 1 and Example 2.

TABLE 6

Affinity of the antibodies AT15-009 and AT15-012 for E2. The binding kinetics of the antibodies was measured for E2 from isolate H77 (genotype 1a) by SPR. The $K_D$ value is the mean of $K_D$ from two independent experiments.

| Antibody | KD (nM) | KD (nM) Example 1 |
|---|---|---|
| AT12-009 | 0.05 | 1.3 |
| AT12-011 | 0.015 | 0.3 |
| AT15-009 | 0.242 | |
| AT15-012 | 0.015 | |

Since AT15-011 and AT15-015 do not bind soluble E2, their affinity could not be determined by SPR using soluble E2. We measured the binding of AT15-011 and AT15-015 to a lysate of 293T/17 cells transfected with E1E2 from H77 (genotype 1a) by ELISA. E1E2 was captured on a GNA lectin coated plate and antibodies were added (0.5 µg/mL to 0.00001 µg/mL). The 50% effective concentration (EC) was determined using non-linear regression analysis (Table 7). AT15-015 showed the highest binding for E1E2, namely 0.0009 µg/mL whereas we determined an EC50 of 0.0019 µg/mL for AT15-011.

TABLE 7

EC50 of the antibodies AT15-011 and AT15-015 for E1E2. The binding of the antibodies was measured using 293T/17 cell lysate containing E1E2 from isolate H77 (genotype 1a) ELISA. The assay was performed by in duplicate.
EC50 (µg/mL)

| AT15-011 | AT15-015 |
|---|---|
| 0.0019 | 0.0009 |

Neutralization Activity

To study the neutralizing capacity of the antibodies, HCVpp from isolates H77 (genotype 1a), AMS.3a.21071213 (genotype 3a), UKN4.11.1 (genotype 4) and AMS.4d.20875969 (genotype 4d) were generated. The B cell culture supernatants containing HCVpp were incubated with a dilution range of B cell supernatants before being added on Huh-7 cells. 50% inhibitory concentrations (IC) neutralization values are shown in Table 8. Potency of the antibodies varied between genotypes. AT15-009 and AT15-012 neutralized all HCVpp (genotype 1, 3 and 4) within an IC50 range of 1 to 0.1 µg/mL, while AT15-011 and AT15-015 showed a more restricted neutralization. AT15-011 and AT15-015 neutralized all HCVpp tested except genotype 4a and 4d using concentrations lower than 1.5 µg/mL and 1.65 µg/mL.

TABLE 8

Neutralization of HCVpp expressing different genotypes by the antibodies. Antibody IC50 in µg/mL.

| Isolate | Genotype | AT15-009 | AT15-011 | AT15-012 | AT15-015 |
|---|---|---|---|---|---|
| H77 | 1a | 0.14 | 0.19 | 0.26 | 0.41 |
| AMS.3a.21071213.kloon26 | 3a | 0.71 | 1.48 | 0.90 | 1.65 |
| UKN4 11.1 | 4a | 1.33 | >1.5 | 1.66 | >1.65 |
| AMS.4d. 20875969. kloon8 | 4d | 2.26 | >1.5 | 1.16 | >1.65 |

Epitope Mapping

To determine which E2 or E1 amino acid residues are important for antibody binding, we generated a panel of H77 E2 alanine mutants, which have been shown to affect binding of known neutralizing antibodies as for instance HC-1, HC-11, CBH-2, CBH-5, e20, e137, HC33 antibodies, AR3 antibodies, AR4A, AR5A and HC84 antibodies family (Keck et al, Journal of virology, 2012; Keck et al, Journal of virology, 2011; Owsianka et al, Journal of general virology, 2008; Perotti et al, Journal of virology, 2008; Mancini et al, plos one, 2009; Law et al. Nature Medicine, 2007; Giang et al., PNAS, 2012, Keck et al, Plos pathogens, 2012). E1 alanine mutants were also generated. Antibody binding was determined by ELISA using a lysate of E1E2 transfected Freestyle™ 293-F cells. The data in Table 9 represents the ratio of antibody binding to E1 or E2 mutants compared to the binding of wild-type protein.

AT15-011 and AT15-015 share an antigen-binding domain on the E2 stem region that is at least composed of the residues R657A and D698A since mutation of these residues resulted in ≤25% binding. Although these residues are present in the soluble E2 protein, AT15-011 and AT15-015 do not bind soluble E2 suggesting that the antibody epitope comprises more residues in E2 and/or include residues in E1 and that the antibody epitope is present after the formation of the E1E2 complex. AT15-009 binding to E2 was (partially) decreased when amino acids F442A and W616A (≤50% binding) were mutated. For AT15-012, we could determine that the antigen binding domain is at least composed of G530 since mutation of this residue resulted in ≤50% binding.

TABLE 9

Epitope mapping of the antibodies. The binding of antibodies to E1 or E2 alanine-mutants was tested by ELISA. N209A and N325A are E1 alanine-mutants (the E1 sequence from HCV genotype 1a, strain H77 is shown in Figure 9) (SEQ ID NO: 147).Shown is the relative antibody binding to the mutant sequences compared to the wild type sequence. When the EC50 could not be calculated because of very weak binding this is indicated by <10%. The assay was performed in duplicate.

|       | AT15-009 | AT15-011 | AT15-012 | AT15-015 |
|-------|----------|----------|----------|----------|
| N209A | 105%     | 70%      | 99%      | 59%      |
| N325A | 103%     | 127%     | 94%      | 81%      |
| L413A | 112%     | 171%     | 132%     | 166%     |
| N415A | 116%     | 98%      | 101%     | 103%     |
| G418A | 112%     | 148%     | 124%     | 124%     |
| W420A | 102%     | 243%     | 111%     | 237%     |
| N423A | 111%     | 158%     | 132%     | 125%     |
| S424A | 106%     | 88%      | 67%      | 91%      |
| T435A | 101%     | 169%     | 99%      | 136%     |
| G436A | 93%      | 132%     | 91%      | 92%      |
| A439G | 97%      | 137%     | 94%      | 122%     |
| L441A | 57%      | 91%      | 83%      | 108%     |
| F442A | 27%      | 86%      | 60%      | 91%      |
| Y443A | 64%      | 78%      | 103%     | 93%      |
| N448A | 113%     | 261%     | 129%     | 183%     |
| T526A | 87%      | 140%     | 82%      | 122%     |
| Y527A | 84%      | 86%      | 76%      | 100%     |
| W529A | 82%      | 109%     | 77%      | 111%     |
| G530A | 52%      | 53%      | 48%      | 71%      |
| N532A | 118%     | 173%     | 125%     | 134%     |
| D533A | 94%      | 116%     | 82%      | 73%      |
| T534A | 93%      | 117%     | 95%      | 104%     |
| D535A | 55%      | 80%      | 52%      | 96%      |
| V538A | 126%     | 111%     | 103%     | 99%      |
| P612A | 94%      | 132%     | 81%      | 116%     |
| W616A | 29%      | 87%      | 71%      | 105%     |
| R657A | 123%     | 2%       | 138%     | <10%     |
| P664A | 101%     | 167%     | 83%      | 119%     |
| P676A | 102%     | 67%      | 92%      | 78%      |
| D698A | 116%     | <10%     | 117%     | 6%       |

Example 3

Material and Methods

Production of the Antibodies

Production of the antibodies AT12-007, AT12-009, AT12-010 and AT13-021 was performed as described in Example 1.

ELISA

Cell lysates containing E1E2 alanine mutants were produced in a similar fashion as described in Example 2.

ELISA assays were performed in a similar fashion as described in Example 2.

Results

Epitope Mapping

In Example 1, we used alanine mutants of eighteen E2 residues to determine residues important for antibody binding of AT12-007, AT12-009, AT12-010, AT12-011 and AT13-021. To determine if additional E2 amino acid residues are important for antibody binding of AT12-007, AT12-009, AT12-010, AT12-011 and AT13-021, we generated a new panel of H77 E2 alanine mutants, which have been shown to affect binding of known neutralizing antibodies as for instance HC33 antibodies, AR3 antibodies, CBH-5, e20 and e137 (Keck et al, Journal of virology, 2012; Law et al. Nature Medicine, 2007; Owsianka et al, Journal of general virology, 2008; Perotti et al, Journal of virology, 2008; Mancini et al, plos one, 2009). Antibody binding was determined by ELISA using a lysate of E1E2 transfected Freestyle™ 293-F cells. The data in Table 10 represents the ratio of antibody binding to E2 mutants compared to the binding of wild-type protein. In Example 1, we showed that AT12-007, AT12-009, AT12-010 and AT13-021 share an antigen binding domain on E2 that is at least composed of the residues F442, Y527, W529, G530, D535, W616. Of these 4 antibodies, only AT12-010 showed ≤25% binding to W420A, suggesting that W420 is part of the epitope of AT12-010. In contrast to AT12-007, AT12-009, AT12-010 and AT13-021, none of the alanine mutations affected binding of AT12-011 in Example 1 and Example 2. This suggests that the binding domain of AT12-011 is completely different compared to known antibodies like, but not limited to, the HC33 antibodies, AR3 antibodies, CBH-5, e20 and e137.

TABLE 10

Extention of epitope mapping of the antibodies from Example 1. Binding of antibodies to E2 alanine-mutants was tested by ELISA. Shown is the relative antibody binding to the mutant sequences compared to the wild type sequence. When the EC50 could not be calculated because of very weak binding this is indicated by <10%. The assaywas performed in duplicate. ND: not done.

| | AT12-009 | AT12-011 | AT12-007 | AT12-010 | AT13-021 |
|---|---|---|---|---|---|
| N209A | 83% | 130% | ND | ND | ND |
| N325A | 87% | 114% | ND | ND | ND |
| L413A | 147% | 86% | 187% | 217% | 185% |
| G418A | 128% | 63% | 130% | 203% | 131% |
| W420A | 120% | 152% | 87% | <10% | 103% |
| N423A | 118% | 181% | ND | ND | ND |
| N448A | 127% | 179% | ND | ND | ND |
| T526A | 57% | 150% | ND | ND | ND |
| Y527A | 52% | 125% | ND | ND | ND |
| N532A | 114% | 145% | ND | ND | ND |
| D533A | 71% | 133% | ND | ND | ND |
| T534A | 100% | 76% | ND | ND | ND |
| V538A | 93% | 121% | ND | ND | ND |
| P612A | 67% | 110% | ND | ND | ND |
| P664A | 73% | 131% | ND | ND | ND |
| P676A | 81% | 154% | ND | ND | ND |

REFERENCES

Albecka A, Montserret R, Krey T, Tarr A W, Diesis E, Ball J K, Descamps V, Duverlie G, Rey F, Penin F, Dubuisson J. Identification of new functional regions in hepatitis C virus envelope glycoprotein E2, J Virol. 2011, 85, 1777-92.

Barretto N., D. N. Martin, N. Hiraga, M. Imamura, S. Hussain, K. A. Marsh, X. Yu, K. Chayama, W. A. Alrefai, B. Sainz, and S. L. Uprichard, Identification of the Niemann-Pick C1-like 1 cholesterol absorption receptor as a new hepatitis C virus entry factor, Nature Medicine, pp. 1-6, January 2012.

Boom R, Sol C J, Salimans M M, Jansen C L, Wertheim-van Dillen P M, van der Noordaa. Rapid and simple method for purification of nucleic acids. J.J Clin Microbiol. 1990, 28, 495-503.

Brimacombe C. L., J. Grove, L. W. Meredith, K. Hu, A. J. Syder, M. V. Flores, J. M. Timpe, S. E. Krieger, T. F. Baumert, T. L. Tellinghuisen, F. Wong-Staal, P. Balfe, and J. A. Mckeating, Neutralizing antibody resistant hepatitis C virus cell-to-cell transmission, J Virol, October 2010.

Chen Y, Wiesmann C, Fuh G, Li B, Christinger H W, McKay P, de Vos A M, Lowman H B. Selection and analysis of an optimized anti-VEGF antibody: crystal structure of an affinity-matured Fab in complex with antigen. J Mol Biol. 1999; 293(4):865-81.

Evans, M. J. et al. Claudin-1 is a hepatitis C virus co-receptor required for a late step in entry. Nature 446, 801-805 (2007).

Giang E, Dorner M, Prentoe J C, Dreux M, Evans M J, Bukh J, Rice C M, Ploss A, Burton D R, Law M. Human broadly neutralizing antibodies to the envelope glycoprotein complex of hepatitis C virus. Proc Natl Acad Sci USA. 2012, 109, 6205-10

Johansson D X, Voisset C, Tarr A W, Aung M, Ball J K, Dubuisson J, Persson M A. Human combinatorial libraries yield rare antibodies that broadly neutralize hepatitis C virus. Proc Natl Acad Sci USA. 2007; 104, 16269-74.

Kabat et al. Sequences of Proteins of Immunological interest, 5th Ed. Public Health Service, National Institute of Health, Bethesda, Md. (1991).

Keck Z Y, Saha A, Xia J, Wang Y, Lau P, Krey T, Rey F A, Foung S K. Mapping a region of hepatitis C virus E2 that is responsible for escape from neutralizing antibodies and a core CD81-binding region that does not tolerate neutralization escape mutations J Virol. 2011, 85, 10451-63.

Keck Z Y, Xia J, Wang Y, Wang W, Krey T, Prentoe J, Carlsen T, Li A Y, Patel A H, Lemon S M, Bukh J, Rey F A, Foung S K. Human monoclonal antibodies to a novel cluster of conformational epitopes on HCV E2 with resistance to neutralization escape in a genotype 2a isolate. PLoS Pathog. 2012; 8

Keck Z., Wang W., Wang Y., Lau P., Carlsen T H., Prentoe J., Xia J., Patel A H., Bukh J., Foung S K. (2013) Cooperativity in Virus Neutralization by Human Monoclonal Antibodies to Two Adjacent Regions Located at the Amino Terminus of Hepatitis C Virus E2 Glycoprotein Journal of virology 87 (1): 37-51

Khan A. G., J. Whidby, M. T. Miller, H. Scarborough, A. V. Zatorski, A. Cygan, A. A. Price, S. A. Yost, C. D. Bohannon, J. Jacob, A. Grakoui, and J. Marcotrigiano, "Structure of the core ectodomain of the hepatitis C virus envelope glycoprotein 2," Nature, pp. 1-15, 2014.

Kong L., E. Giang, T. Nieusma, R. U. Kadam, K. E. Cogburn, Y. Hua, X. Dai, R. L. Stanfield, D. R. Burton, A. B. Ward, I. A. Wilson, and M. Law, "Hepatitis C Virus E2 Envelope Glycoprotein Core Structure," Science, vol. 342, no. 6162, pp. 1090-1094, 2013

Kwakkenbos M J, Diehl S A, Yasuda E, et al. Generation of stable monoclonal antibody-producing B cell receptor-positive human memory B cells by genetic programming. Nature Medicine. 2010; 16(1):123-128.

Kwakkenbos M J, Bakker A Q, van Helden P M, et al. Genetic manipulation of B cells for the isolation of rare therapeutic antibodies from the human repertoire. Methods. 2013; 1-6.

Lavillette D, Tarr A W, Voisset C, Donot P, Bartosch B, Bain C, Patel A H, Dubuisson J, Ball J K, Cosset F L. Characterization of host-range and cell entry properties of the major genotypes and subtypes of hepatitis C virus. Hepatology. 2005, 41, 265-74.

Law M, Maruyama T, Lewis J, Giang E, Tarr A W, Stamataki Z, Gastaminza P, Chisari F V, Jones I M, Fox R I, Ball J K, McKeating J A, Kneteman N M, Burton D R. Broadly neutralizing antibodies protect against hepatitis C virus quasispecies challenge. Nature Medicine. 2008,14, 25-7.

Liang, T. J. & Ghany, M. G. Current and Future Therapies for Hepatitis C Virus Infection. N Engl J Med 368, 1907-1917 (2013].

Lokate A M, Beusink J B, Besselink G A, Pruijn G J, Schasfoort R B. Biomolecular interaction monitoring of autoantibodies by scanning surface plasmon resonance microarray imaging. J Am Chem Soc. 2007, 129, 14013-14018.

Mancini N, Diotti R A, Perotti M, Sautto G, Clementi N, Nitti G, Patel A H, Ball J K, Clementi M, Burioni R. Hepatitis C virus (HCV) infection may elicit neutralizing antibodies targeting epitopes conserved in all viral genotypes. PLoS One. 2009, 4

Owsianka A M, Tarr A W, Keck Z Y, Li T K, Witteveldt J, Adair R, Foung S K, Ball J K, Patel A H. Broadly neutralizing human monoclonal antibodies to the hepatitis C virus E2 glycoprotein. J Gen Virol. 2008, 89, 653-9.

Perotti M, Mancini N, Diotti R A, Tarr A W, Ball J K, Owsianka A, Adair R, Patel A H, Clementi M, Burioni R. Identification of a broadly cross-reacting and neutralizing human monoclonal antibody directed against the hepatitis C virus E2 protein. J Virol. 2008; 82, 1047-52.

Pileri, P. et al. Binding of hepatitis C virus to CD81. Science 282, 938-941 (1998).

Ploss, A. et al. Human occludin is a hepatitis C virus entry factor required for infection of mouse cells. Nature 457, 882-886 (2009).

Poordad, F. et al. ABT-450/r-Ombitasvir and Dasabuvir with Ribavirin for Hepatitis C with Cirrhosis. N Engl J Med 370, 1973-1982 (2014).

Scarselli, E. et al. The human scavenger receptor class B type I is a novel candidate receptor for the hepatitis C virus. EMBO J. 21, 5017-5025 (2002).

Schasfoort R. B. M., de Lau, W., van der Kooi, A., Clevers, H., Engbers, G. H. M. (2012) Method for estimating the single molecular affinity Analytical Biochemistry 421(2): 794-796

Sulkowski, M. S. et al. Daclatasvir plus Sofosbuvir for Previously Treated or Untreated Chronic HCV Infection. N Engl J Med 370, 211-221 (2014).

Xiao, F. et al. Hepatitis C Virus Cell-Cell Transmission and Resistance to Direct-Acting Antiviral Agents. PLoS Pathog 10, e1004128 (2014).

Wang Y, Keck Z Y, Foung S K. Neutralizing antibody response to hepatitis C virus. Viruses. 2011 November; 3(11):2127-45.

---

The invention claimed is:

1. A synthetic or recombinant antibody or an antigen binding fragment thereof that specifically binds HCV E2 or HCV E1E2, comprising the CDR sequences of:
SEQ ID NOs 1, 6, 11, 16, 21 and 26;
SEQ ID NOs 2, 7, 12, 17, 22 and 27;
SEQ ID NOs 3, 8, 13, 18, 23 and 28;
SEQ ID NOs 4, 9, 14, 19, 24 and 29;
SEQ ID NOs 5, 10, 15, 20, 25 and 30;
SEQ ID NOs 81, 85, 89, 93, 97 and 101;
SEQ ID NOs 82, 86, 90, 94, 98 and 102;
SEQ ID NOs 83, 87, 91, 95, 99 and 103; or
SEQ ID NOs 84, 88, 92, 96, 100 and 104.

2. The antibody or antigen binding fragment thereof of claim 1, further comprising at least one of:

a heavy chain variable region sequence comprising a sequence which has at least 80% sequence identity with a sequence selected from the group consisting of SEQ ID NOs:31-35 and SEQ ID NOs 105-108; or a light chain variable region sequence which has at least 80% sequence identity with a sequence selected from the group consisting of SEQ ID NOs:36-40 and SEQ ID NOs: 109-112.

3. The antibody or antigen binding fragment thereof of claim 1, wherein said antibody or antigen binding fragment thereof specifically binds to an epitope of hepatitis C virus (HCV) protein E2, said epitope comprising amino acids corresponding to amino acids F442, Y527, W529, G530, D535 and W616 of the H77 E2 amino acid sequence (SEQ ID NO: 145), and wherein said antibody or antigen binding fragment thereof inhibits binding of HCV protein E1E2 to CD81.

4. A method of treating an HCV infection in a patient in need thereof, comprising administering a synthetic or recombinant antibody, or an antigen binding fragment thereof according to claim 1, to said patient.

5. A method for determining whether an individual is suffering from a HCV infection, comprising:
contacting a sample from said individual with the antibody or antigen binding fragment thereof of claim 1 and
allowing said antibody or antigen binding fragment thereof to bind HCV, if present, and
determining whether or not HCV is bound to said antibody or antigen binding fragment thereof, thereby determining whether or nor said individual is suffering from HCV infection.

6. A method of inhibiting binding of HCV protein E1E2 to CD81 comprising:
administering to a patient a synthetic or recombinant antibody, or an antigen binding fragment thereof, according to claim 1.

7. A method for producing the antibody or an antigen binding fragment thereof of claim 1, the method comprising:
providing a cell with a nucleic acid molecule or a vector, said nucleic acid molecule or vector comprising sequences encoding the CDRs of the antibody or antigen binding fragment thereof of claim 1;
allowing said cell to translate the nucleic acid sequence comprised by said nucleic acid molecule or vector, thereby producing said antibody or antigen binding fragment thereof of claim 1;
harvesting, purifying and/or isolating said antibody or antigen binding fragment thereof of claim 1.

* * * * *

SEQUENCE LISTING

```
<160> NUMBER OF SEQ ID NOS: 147

<210> SEQ ID NO 1
<211> LENGTH: 5
<212> TYPE: PRT
<213> ORGANISM: Artificial Sequence
<220> FEATURE:
<223> OTHER INFORMATION: AT12-011 Heavy chain CDR1

<400> SEQUENCE: 1

Gly Tyr Gly Ile Thr
1               5

<210> SEQ ID NO 2
<211> LENGTH: 5
<212> TYPE: PRT
<213> ORGANISM: Artificial Sequence
<220> FEATURE:
<223> OTHER INFORMATION: AT12-007 Heavy chain CDR1

<400> SEQUENCE: 2

Glu Leu Ser Met His
1               5

<210> SEQ ID NO 3
<211> LENGTH: 5
<212> TYPE: PRT
<213> ORGANISM: Artificial Sequence
<220> FEATURE:
<223> OTHER INFORMATION: AT12-009 Heavy chain CDR1

<400> SEQUENCE: 3

Thr His Ala Ile Ser
1               5

<210> SEQ ID NO 4
<211> LENGTH: 4
<212> TYPE: PRT
<213> ORGANISM: Artificial Sequence
<220> FEATURE:
<223> OTHER INFORMATION: AT12-010 Heavy chain CDR1

<400> SEQUENCE: 4

Tyr Ala Ile Asn
1

<210> SEQ ID NO 5
<211> LENGTH: 5
<212> TYPE: PRT
<213> ORGANISM: Artificial Sequence
<220> FEATURE:
<223> OTHER INFORMATION: AT13-021 Heavy chain CDR1

<400> SEQUENCE: 5
```

Thr His Ala Phe Ser
1               5

<210> SEQ ID NO 6
<211> LENGTH: 17
<212> TYPE: PRT
<213> ORGANISM: Artificial Sequence
<220> FEATURE:
<223> OTHER INFORMATION: AT12-011 Heavy chain CDR2

<400> SEQUENCE: 6

Thr Ile Ile Pro Val Ser Ala Thr Glu Thr Tyr Ala Gln Arg Leu Gln
1               5                   10                  15

Gly

<210> SEQ ID NO 7
<211> LENGTH: 17
<212> TYPE: PRT
<213> ORGANISM: Artificial Sequence
<220> FEATURE:
<223> OTHER INFORMATION: AT12-007 Heavy chain CDR2

<400> SEQUENCE: 7

Ser Phe Asp Pro Ala Asp Gly Glu Arg Leu Tyr Ala Gln Lys Phe Gln
1               5                   10                  15

Gly

<210> SEQ ID NO 8
<211> LENGTH: 32
<212> TYPE: PRT
<213> ORGANISM: Artificial Sequence
<220> FEATURE:
<223> OTHER INFORMATION: AT12-009 Heavy chain CDR2

<400> SEQUENCE: 8

Gly Thr Val Arg Gln Ala Pro Gly Asp Gly Leu Glu Leu Leu Gly Gly
1               5                   10                  15

Phe Val Pro Ile Leu Ala Pro Ala Asn Asp Ala Gln Lys Phe Gln Gly
                20                  25                  30

<210> SEQ ID NO 9
<211> LENGTH: 17
<212> TYPE: PRT
<213> ORGANISM: Artificial Sequence
<220> FEATURE:
<223> OTHER INFORMATION: AT12-010 Heavy chain CDR2

<400> SEQUENCE: 9

Glu Ile Ser Pro Val Phe Gly Thr Thr His Tyr Ala Gln Lys Phe Gln
1               5                   10                  15

Gly

<210> SEQ ID NO 10
<211> LENGTH: 17
<212> TYPE: PRT
<213> ORGANISM: Artificial Sequence
<220> FEATURE:
<223> OTHER INFORMATION: AT13-021 Heavy chain CDR2

<400> SEQUENCE: 10

Gly Ile Ser Pro Met Ser Gly Thr Pro Asn Tyr Ala Gln Lys Phe Gln
1               5                   10                  15

Gly

<210> SEQ ID NO 11
<211> LENGTH: 11
<212> TYPE: PRT
<213> ORGANISM: Artificial Sequence
<220> FEATURE:
<223> OTHER INFORMATION: AT12-011 Heavy chain CDR3

<400> SEQUENCE: 11

His Asp Tyr Phe Trp Gly Thr Pro Leu Asp Ile
1               5                   10

<210> SEQ ID NO 12
<211> LENGTH: 15
<212> TYPE: PRT
<213> ORGANISM: Artificial Sequence
<220> FEATURE:
<223> OTHER INFORMATION: AT12-007 Heavy chain CDR3

<400> SEQUENCE: 12

Ala Pro Arg Met Thr Met Phe Gly Val Ile Met Ala Leu Asp Ser
1               5                   10                  15

<210> SEQ ID NO 13
<211> LENGTH: 25
<212> TYPE: PRT
<213> ORGANISM: Artificial Sequence
<220> FEATURE:
<223> OTHER INFORMATION: AT12-009 Heavy chain CDR3

<400> SEQUENCE: 13

Ser Leu Ser Glu Pro Ile Pro Arg Ser Cys Arg Gly Gly Arg Cys Tyr
1               5                   10                  15

Ser Gly Pro Phe Asp Ala Phe Gly Val
            20                  25

<210> SEQ ID NO 14
<211> LENGTH: 18
<212> TYPE: PRT
<213> ORGANISM: Artificial Sequence
<220> FEATURE:
<223> OTHER INFORMATION: AT12-010 Heavy chain CDR3

<400> SEQUENCE: 14

Asp Arg Ala Pro Arg Leu Cys Ser Gly Gly Arg Cys His Ser Pro Pro
1               5                   10                  15

Asp His

<210> SEQ ID NO 15
<211> LENGTH: 17
<212> TYPE: PRT
<213> ORGANISM: Artificial Sequence
<220> FEATURE:
<223> OTHER INFORMATION: AT13-021 Heavy chain CDR3

<400> SEQUENCE: 15

Glu Leu Ile Gly Tyr Cys Thr Gly Gly Asn Cys Tyr Ser Phe Gly Asp
1               5                   10                  15

Phe

<210> SEQ ID NO 16
<211> LENGTH: 11
<212> TYPE: PRT
<213> ORGANISM: Artificial Sequence
<220> FEATURE:

<223> OTHER INFORMATION: AT12-011 Light chain CDR1

<400> SEQUENCE: 16

Arg Ala Ser Gln Ser Ile Gly Ser Asn Leu His
1               5                   10

<210> SEQ ID NO 17
<211> LENGTH: 11
<212> TYPE: PRT
<213> ORGANISM: Artificial Sequence
<220> FEATURE:
<223> OTHER INFORMATION: AT12-007 Light chain CDR1

<400> SEQUENCE: 17

Arg Ala Ser Gln Asn Ile Asn Lys Tyr Leu Ala
1               5                   10

<210> SEQ ID NO 18
<211> LENGTH: 11
<212> TYPE: PRT
<213> ORGANISM: Artificial Sequence
<220> FEATURE:
<223> OTHER INFORMATION: AT12-009 Light chain CDR1

<400> SEQUENCE: 18

Arg Ala Ser Gln Ser Ile Gly Thr Asn Leu Ala
1               5                   10

<210> SEQ ID NO 19
<211> LENGTH: 11
<212> TYPE: PRT
<213> ORGANISM: Artificial Sequence
<220> FEATURE:
<223> OTHER INFORMATION: AT12-010 Light chain CDR1

<400> SEQUENCE: 19

Arg Ala Ser Gln Gly Phe Gly Asn Trp Leu Ala
1               5                   10

<210> SEQ ID NO 20
<211> LENGTH: 11
<212> TYPE: PRT
<213> ORGANISM: Artificial Sequence
<220> FEATURE:
<223> OTHER INFORMATION: AT13-021 Light chain CDR1

<400> SEQUENCE: 20

Arg Ala Ser Gln Ser Val Ser Ser His Leu Ala
1               5                   10

<210> SEQ ID NO 21
<211> LENGTH: 7
<212> TYPE: PRT
<213> ORGANISM: Artificial Sequence
<220> FEATURE:
<223> OTHER INFORMATION: AT12-011 Light chain CDR2

<400> SEQUENCE: 21

Tyr Ala Ser Gln Ser Phe Ser
1               5

<210> SEQ ID NO 22
<211> LENGTH: 7
<212> TYPE: PRT
<213> ORGANISM: Artificial Sequence
<220> FEATURE:
<223> OTHER INFORMATION: AT12-007 Light chain CDR2

```
<400> SEQUENCE: 22

Lys Ala Ser Asn Leu Gln Ser
1               5

<210> SEQ ID NO 23
<211> LENGTH: 7
<212> TYPE: PRT
<213> ORGANISM: Artificial Sequence
<220> FEATURE:
<223> OTHER INFORMATION: AT12-009 Light chain CDR2

<400> SEQUENCE: 23

Gly Ala Ser Thr Arg Ala Thr
1               5

<210> SEQ ID NO 24
<211> LENGTH: 7
<212> TYPE: PRT
<213> ORGANISM: Artificial Sequence
<220> FEATURE:
<223> OTHER INFORMATION: AT12-010 Light chain CDR2

<400> SEQUENCE: 24

Gly Ala Ser Thr Leu Gln Asn
1               5

<210> SEQ ID NO 25
<211> LENGTH: 7
<212> TYPE: PRT
<213> ORGANISM: Artificial Sequence
<220> FEATURE:
<223> OTHER INFORMATION: AT13-021 Light chain CDR2

<400> SEQUENCE: 25

Gly Ala Ser Thr Arg Ala Val
1               5

<210> SEQ ID NO 26
<211> LENGTH: 7
<212> TYPE: PRT
<213> ORGANISM: Artificial Sequence
<220> FEATURE:
<223> OTHER INFORMATION: AT12-011 Light chain CDR3

<400> SEQUENCE: 26

His Gln Ser Tyr Asn Leu Pro
1               5

<210> SEQ ID NO 27
<211> LENGTH: 8
<212> TYPE: PRT
<213> ORGANISM: Artificial Sequence
<220> FEATURE:
<223> OTHER INFORMATION: AT12-007 Light chain CDR3

<400> SEQUENCE: 27

Gln Gln Tyr Thr Thr Tyr Ser Ala
1               5

<210> SEQ ID NO 28
<211> LENGTH: 7
<212> TYPE: PRT
<213> ORGANISM: Artificial Sequence
<220> FEATURE:
<223> OTHER INFORMATION: AT12-009 Light chain CDR3
```

```
<400> SEQUENCE: 28

Gln Gln Tyr Asn Asn Trp Pro
1               5

<210> SEQ ID NO 29
<211> LENGTH: 7
<212> TYPE: PRT
<213> ORGANISM: Artificial Sequence
<220> FEATURE:
<223> OTHER INFORMATION: AT12-010 Light chain CDR3

<400> SEQUENCE: 29

Leu Gln Thr Asn Thr Phe Pro
1               5

<210> SEQ ID NO 30
<211> LENGTH: 7
<212> TYPE: PRT
<213> ORGANISM: Artificial Sequence
<220> FEATURE:
<223> OTHER INFORMATION: AT13-021 Light chain CDR3

<400> SEQUENCE: 30

His Gln Tyr Asn Thr Trp Pro
1               5

<210> SEQ ID NO 31
<211> LENGTH: 120
<212> TYPE: PRT
<213> ORGANISM: Artificial Sequence
<220> FEATURE:
<223> OTHER INFORMATION: AT12-011 Heavy chain

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Gly Tyr
            20                  25                  30

Gly Ile Thr Trp Val Arg Gln Ala Pro Gly Gln Gly Leu Glu Trp Met
        35                  40                  45

Gly Thr Ile Ile Pro Val Ser Ala Thr Glu Thr Tyr Ala Gln Arg Leu
    50                  55                  60

Gln Gly Arg Val Thr Ile Ser Ala Asp Glu His Ser Thr Thr Ser Tyr
65                  70                  75                  80

Met Glu Val Ser Ser Leu Lys Ser Glu Asp Thr Ala Leu Tyr Tyr Cys
                85                  90                  95

Ala Arg His Asp Tyr Phe Trp Gly Thr Pro Leu Asp Ile Trp Gly Gln
            100                 105                 110

Gly Thr Met Val Ile Val Ser Ser
        115                 120

<210> SEQ ID NO 32
<211> LENGTH: 124
<212> TYPE: PRT
<213> ORGANISM: Artificial Sequence
<220> FEATURE:
<223> OTHER INFORMATION: AT12-007 Heavy chain

<400> SEQUENCE: 32

Gln Val Gln Leu Glu Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
```

```
                20                  25                  30

Ser Met His Trp Val Arg Gln Ala Pro Gly Lys Gly Leu Glu Trp Met
            35                  40                  45

Gly Ser Phe Asp Pro Ala Asp Gly Glu Arg Leu Tyr Ala Gln Lys Phe
        50                  55                  60

Gln Gly Arg Val Ile Met Ser Glu Asp Thr Ser Thr Asp Thr Ala Tyr
65                  70                  75                  80

Met Glu Leu Ser Ser Leu Arg Ser Glu Asp Ala Ala Val Tyr Tyr Cys
                85                  90                  95

Ala Thr Ala Pro Arg Met Thr Met Phe Gly Val Ile Met Ala Leu Asp
            100                 105                 110

Ser Trp Gly Gln Gly Thr Leu Val Thr Val Ser Ser
            115                 120

<210> SEQ ID NO 33
<211> LENGTH: 149
<212> TYPE: PRT
<213> ORGANISM: Artificial Sequence
<220> FEATURE:
<223> OTHER INFORMATION: AT12-009 Heavy chain

<400> SEQUENCE: 33

Gln Glu Arg Leu Val Gln Ser Gly Ala Glu Val Lys Lys Pro Gly Ser
1               5                   10                  15

Ser Val Arg Val Ser Cys Lys Ala Ser Gly Asp Thr Phe Lys Thr His
            20                  25                  30

Ala Ile Ser Trp Val Arg Gln Ala Pro Gly Gln Gly Leu Glu Trp Val
            35                  40                  45

Gly Gly Thr Val Arg Gln Ala Pro Gly Asp Gly Leu Glu Leu Leu Gly
        50                  55                  60

Gly Phe Val Pro Ile Leu Ala Pro Ala Asn Asp Ala Gln Lys Phe Gln
65                  70                  75                  80

Gly Arg Val Thr Ile Thr Ala Asp Gly Ser Thr Gly Pro Val Tyr Met
                85                  90                  95

Asp Leu Ser Thr Leu Thr Ser Glu Asp Thr Ala Met Tyr Tyr Cys Val
            100                 105                 110

Thr Ser Leu Ser Glu Pro Ile Pro Arg Ser Cys Arg Gly Gly Arg Cys
            115                 120                 125

Tyr Ser Gly Pro Phe Asp Ala Phe Gly Val Trp Gly Gln Gly Thr Met
            130                 135                 140

Val Thr Val Ser Ser
145

<210> SEQ ID NO 34
<211> LENGTH: 127
<212> TYPE: PRT
<213> ORGANISM: Artificial Sequence
<220> FEATURE:
<223> OTHER INFORMATION: AT12-010 Heavy chain

<400> SEQUENCE: 34

Gln Leu Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Ser Tyr
            20                  25                  30

Ala Ile Asn Trp Val Arg Gln Val Pro Gly Gln Gly Leu Glu Trp Met
            35                  40                  45
```

Gly Glu Ile Ser Pro Val Phe Gly Thr Thr His Tyr Ala Gln Lys Phe
            50                  55                  60

Gln Gly Arg Leu Lys Ile Thr Ala Asp Glu Ser Ala Asp Thr Ala Tyr
65                  70                  75                  80

Met Glu Leu Ser Ser Leu Arg Ser Asp Thr Ala Val Tyr Tyr Cys
                85                  90                  95

Gly Arg Asp Arg Ala Pro Arg Leu Cys Ser Gly Arg Cys His Ser
                100                 105                 110

Pro Pro Asp His Trp Gly Gln Gly Thr Leu Val Thr Val Ser Ser
            115                 120                 125

<210> SEQ ID NO 35
<211> LENGTH: 126
<212> TYPE: PRT
<213> ORGANISM: Artificial Sequence
<220> FEATURE:
<223> OTHER INFORMATION: AT13-021 Heavy chain

<400> SEQUENCE: 35

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Thr His
            20                  25                  30

Ala Phe Ser Trp Val Arg Gln Ala Pro Gly Glu Gly Leu Glu Trp Met
        35                  40                  45

Gly Gly Ile Ser Pro Met Ser Gly Thr Pro Asn Tyr Ala Gln Lys Phe
    50                  55                  60

Gln Gly Arg Leu Thr Ile Thr Ala Asp Glu Ser Thr Ser Thr Gly Tyr
65                  70                  75                  80

Met Glu Leu Arg Ser Leu Thr Ser Glu Asp Thr Ala Val Tyr Tyr Cys
                85                  90                  95

Ala Arg Glu Leu Ile Gly Tyr Cys Thr Gly Gly Asn Cys Tyr Ser Phe
                100                 105                 110

Gly Asp Phe Trp Gly Gln Gly Thr Leu Ile Thr Val Ser Ser
            115                 120                 125

<210> SEQ ID NO 36
<211> LENGTH: 112
<212> TYPE: PRT
<213> ORGANISM: Artificial Sequence
<220> FEATURE:
<223> OTHER INFORMATION: AT12-011 Light chain

<400> SEQUENCE: 36

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Asn
            20                  25                  30

Leu His Trp Tyr Gln Gln Lys Pro Gly Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Phe Cys His Gln Ser Tyr Asn Leu Pro Arg
                85                  90                  95

Thr Phe Gly Gly Gly Thr Lys Val Glu Ile Lys Arg Thr Val Ala Ala
                100                 105                 110

<210> SEQ ID NO 37
<211> LENGTH: 112
<212> TYPE: PRT
<213> ORGANISM: Artificial Sequence
<220> FEATURE:
<223> OTHER INFORMATION: AT12-007 Light chain

<400> SEQUENCE: 37

Asp Ile Gln Met Thr Gln Ser Pro Ser Thr Leu Ser Ala Ser Leu Gly
1               5                   10                  15

Asp Arg Val Thr Ile Thr Cys Arg Ala Ser Gln Asn Ile Asn Lys Tyr
            20                  25                  30

Leu Ala Trp Tyr Gln Gln Lys Pro Gly Lys Ala Pro Lys Leu Leu Ile
        35                  40                  45

Tyr Lys Ala Ser Asn Leu Gln Ser Gly Val Pro Ser Arg Phe Ser Gly
    50                  55                  60

Ser Gly Ser Gly Thr Asp Phe Ile Leu Thr Ile Ser Ser Leu Gln Pro
65                  70                  75                  80

Asp Asp Phe Ala Thr Tyr Tyr Cys Gln Gln Tyr Thr Thr Tyr Ser Ala
                85                  90                  95

Trp Thr Phe Gly Gln Gly Thr Asn Val Asp Ile Lys Arg Thr Val Ala
            100                 105                 110

<210> SEQ ID NO 38
<211> LENGTH: 112
<212> TYPE: PRT
<213> ORGANISM: Artificial Sequence
<220> FEATURE:
<223> OTHER INFORMATION: AT12-009 Light chain

<400> SEQUENCE: 38

Glu Thr Met Leu Thr Gln Ser Pro Val Thr Leu Ser Val Ser Pro Gly
1               5                   10                  15

Glu Arg Ala Thr Leu Ser Cys Arg Ala Ser Gln Ser Ile Gly Thr Asn
            20                  25                  30

Leu Ala Trp Tyr Gln Gln Lys Pro Gly Gln Ala Pro Arg Leu Leu Ile
        35                  40                  45

His Gly Ala Ser Thr Arg Ala Thr Gly Val Pro Val Ser Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Asp Phe Lys Arg Thr Val Ala Ala
            100                 105                 110

<210> SEQ ID NO 39
<211> LENGTH: 112
<212> TYPE: PRT
<213> ORGANISM: Artificial Sequence
<220> FEATURE:
<223> OTHER INFORMATION: AT12-010 Light chain

<400> SEQUENCE: 39

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Phe Gly Asn Trp
            20                  25                  30

Leu Ala Trp Tyr Gln Gln Lys Pro Gly Arg Ala Pro Lys Leu Leu Ile
            35                  40                  45

Phe Gly Ala Ser Thr Leu Gln Asn Gly Val Pro Ser Arg Phe Ser Gly
 50                  55                  60

Ser Ala Ser Gly Thr Asp Phe Thr Leu Thr Ile Thr Ser Leu Gln Pro
 65                  70                  75                  80

Glu Asp Phe Ala Thr Tyr Tyr Cys Leu Gln Thr Asn Thr Phe Pro Tyr
                    85                  90                  95

Thr Phe Gly Gln Gly Thr Lys Val Glu Ile Lys Arg Thr Val Ala Ala
                100                 105                 110

<210> SEQ ID NO 40
<211> LENGTH: 112
<212> TYPE: PRT
<213> ORGANISM: Artificial Sequence
<220> FEATURE:
<223> OTHER INFORMATION: AT13-021 Light chain

<400> SEQUENCE: 40

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser His
                20                  25                  30

Leu Ala Trp Tyr Gln His Lys Pro Gly Gln Ala Pro Arg Leu Leu Ile
            35                  40                  45

Ser Gly Ala Ser Thr Arg Ala Val Gly Val Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys His Gln Tyr Asn Thr Trp Pro Arg
                    85                  90                  95

Gly Phe Gly Gln Gly Thr Lys Val Asp Phe Lys Arg Thr Val Ala Ala
                100                 105                 110

<210> SEQ ID NO 41
<211> LENGTH: 15
<212> TYPE: DNA
<213> ORGANISM: Artificial Sequence
<220> FEATURE:
<223> OTHER INFORMATION: AT12-011 Heavy chain CDR1

<400> SEQUENCE: 41
ggatatggta tcacc                                                     15

<210> SEQ ID NO 42
<211> LENGTH: 15
<212> TYPE: DNA
<213> ORGANISM: Artificial Sequence
<220> FEATURE:
<223> OTHER INFORMATION: AT12-007 Heavy chain CDR1

<400> SEQUENCE: 42
gagttatcca tgcac                                                     15

<210> SEQ ID NO 43
<211> LENGTH: 15
<212> TYPE: DNA
<213> ORGANISM: Artificial Sequence
<220> FEATURE:
<223> OTHER INFORMATION: AT12-009 Heavy chain CDR1

<400> SEQUENCE: 43

-continued

```
actcatgcca tcagt                                                       15

<210> SEQ ID NO 44
<211> LENGTH: 12
<212> TYPE: DNA
<213> ORGANISM: Artificial Sequence
<220> FEATURE:
<223> OTHER INFORMATION: AT12-010 Heavy chain CDR1

<400> SEQUENCE: 44
tatgctatca ac                                                          12

<210> SEQ ID NO 45
<211> LENGTH: 15
<212> TYPE: DNA
<213> ORGANISM: Artificial Sequence
<220> FEATURE:
<223> OTHER INFORMATION: AT13-021 Heavy chain CDR1

<400> SEQUENCE: 45
acccatgcat tcagc                                                       15

<210> SEQ ID NO 46
<211> LENGTH: 51
<212> TYPE: DNA
<213> ORGANISM: Artificial Sequence
<220> FEATURE:
<223> OTHER INFORMATION: AT12-011 Heavy chain CDR2

<400> SEQUENCE: 46
acaatcatcc ctgtttctgc tacggaaacc tacgcacaga ggttgcaggg c                51

<210> SEQ ID NO 47
<211> LENGTH: 51
<212> TYPE: DNA
<213> ORGANISM: Artificial Sequence
<220> FEATURE:
<223> OTHER INFORMATION: AT12-007 Heavy chain CDR2

<400> SEQUENCE: 47
agttttgatc ctgcagatgg tgaaagactt tacgcacaga agttccaggg a                51

<210> SEQ ID NO 48
<211> LENGTH: 96
<212> TYPE: DNA
<213> ORGANISM: Artificial Sequence
<220> FEATURE:
<223> OTHER INFORMATION: AT12-009 Heavy chain CDR2

<400> SEQUENCE: 48
gggaccgtgc gacaggcccc cggagacggg cttgagttgc tgggagggtt cgtccccatc       60
cttgctccag cgaacgacgc ccagaagttc cagggc                                 96

<210> SEQ ID NO 49
<211> LENGTH: 51
<212> TYPE: DNA
<213> ORGANISM: Artificial Sequence
<220> FEATURE:
<223> OTHER INFORMATION: AT12-010 Heavy chain CDR2

<400> SEQUENCE: 49
gagatcagcc tgtctttgg aacaacacac tacgcacaga agttccaggg c                 51

<210> SEQ ID NO 50
```

```
<211> LENGTH: 51
<212> TYPE: DNA
<213> ORGANISM: Artificial Sequence
<220> FEATURE:
<223> OTHER INFORMATION: AT13-021 Heavy chain CDR2

<400> SEQUENCE: 50
gggatcagcc ctatgtctgg cacaccaaac tacgcacaga aattccaggg c            51

<210> SEQ ID NO 51
<211> LENGTH: 33
<212> TYPE: DNA
<213> ORGANISM: Artificial Sequence
<220> FEATURE:
<223> OTHER INFORMATION: AT12-011 Heavy chain CDR3

<400> SEQUENCE: 51
cacgactact tttgggggac tccgcttgat atc                                33

<210> SEQ ID NO 52
<211> LENGTH: 45
<212> TYPE: DNA
<213> ORGANISM: Artificial Sequence
<220> FEATURE:
<223> OTHER INFORMATION: AT12-007 Heavy chain CDR3

<400> SEQUENCE: 52
gccccacgta tgacgatgtt tggggtgata atggccttag actcc                   45

<210> SEQ ID NO 53
<211> LENGTH: 75
<212> TYPE: DNA
<213> ORGANISM: Artificial Sequence
<220> FEATURE:
<223> OTHER INFORMATION: AT12-009 Heavy chain CDR3

<400> SEQUENCE: 53
tcgctttcag aacccatacc aaggtcttgt cgtggtggta gatgctactc cggccctttt   60
gatgcttttg gtgtt                                                    75

<210> SEQ ID NO 54
<211> LENGTH: 54
<212> TYPE: DNA
<213> ORGANISM: Artificial Sequence
<220> FEATURE:
<223> OTHER INFORMATION: AT12-010 Heavy chain CDR3

<400> SEQUENCE: 54
gatagggccc ctagattgtg tagtggtggt cgctgccact ccccccctga ccac         54

<210> SEQ ID NO 55
<211> LENGTH: 51
<212> TYPE: DNA
<213> ORGANISM: Artificial Sequence
<220> FEATURE:
<223> OTHER INFORMATION: AT13-021 Heavy chain CDR3

<400> SEQUENCE: 55
gagttgatcg ggtattgcac tggtggtaac tgctactcat tcggtgactt t            51

<210> SEQ ID NO 56
<211> LENGTH: 33
<212> TYPE: DNA
<213> ORGANISM: Artificial Sequence
<220> FEATURE:
<223> OTHER INFORMATION: AT12-011 Light chain CDR1
```

```
<400> SEQUENCE: 56
cgggccagtc agagcattgg tagtaattta cac                                33

<210> SEQ ID NO 57
<211> LENGTH: 33
<212> TYPE: DNA
<213> ORGANISM: Artificial Sequence
<220> FEATURE:
<223> OTHER INFORMATION: AT12-007 Light chain CDR1

<400> SEQUENCE: 57
cgggccagtc agaatattaa taaatatttg gcc                                33

<210> SEQ ID NO 58
<211> LENGTH: 33
<212> TYPE: DNA
<213> ORGANISM: Artificial Sequence
<220> FEATURE:
<223> OTHER INFORMATION: AT12-009 Light chain CDR1

<400> SEQUENCE: 58
agggccagtc agagtattgg taccaactta gcc                                33

<210> SEQ ID NO 59
<211> LENGTH: 33
<212> TYPE: DNA
<213> ORGANISM: Artificial Sequence
<220> FEATURE:
<223> OTHER INFORMATION: AT12-010 Light chain CDR1

<400> SEQUENCE: 59
cgggcgagtc agggttttgg caactggtta gcc                                33

<210> SEQ ID NO 60
<211> LENGTH: 33
<212> TYPE: DNA
<213> ORGANISM: Artificial Sequence
<220> FEATURE:
<223> OTHER INFORMATION: AT13-021 Light chain CDR1

<400> SEQUENCE: 60
agggccagtc agagtgttag cagccactta gcc                                33

<210> SEQ ID NO 61
<211> LENGTH: 21
<212> TYPE: DNA
<213> ORGANISM: Artificial Sequence
<220> FEATURE:
<223> OTHER INFORMATION: AT12-011 Light chain CDR2

<400> SEQUENCE: 61
tatgcttccc agtccttctc a                                             21

<210> SEQ ID NO 62
<211> LENGTH: 21
<212> TYPE: DNA
<213> ORGANISM: Artificial Sequence
<220> FEATURE:
<223> OTHER INFORMATION: AT12-007 Light chain CDR2

<400> SEQUENCE: 62
aaggcgtcta atttacaaag t                                             21

<210> SEQ ID NO 63
```

<211> LENGTH: 21
<212> TYPE: DNA
<213> ORGANISM: Artificial Sequence
<220> FEATURE:
<223> OTHER INFORMATION: AT12-009 Light chain CDR2

<400> SEQUENCE: 63
ggtgcatcta ccagggccac t                                          21

<210> SEQ ID NO 64
<211> LENGTH: 21
<212> TYPE: DNA
<213> ORGANISM: Artificial Sequence
<220> FEATURE:
<223> OTHER INFORMATION: AT12-010 Light chain CDR2

<400> SEQUENCE: 64
ggtgcatcca ctttgcaaaa t                                          21

<210> SEQ ID NO 65
<211> LENGTH: 21
<212> TYPE: DNA
<213> ORGANISM: Artificial Sequence
<220> FEATURE:
<223> OTHER INFORMATION: AT13-021 Light chain CDR2

<400> SEQUENCE: 65
ggtgcatcca ccagggccgt t                                          21

<210> SEQ ID NO 66
<211> LENGTH: 21
<212> TYPE: DNA
<213> ORGANISM: Artificial Sequence
<220> FEATURE:
<223> OTHER INFORMATION: AT12-011 Light chain CDR3

<400> SEQUENCE: 66
catcagagtt ataatttacc g                                          21

<210> SEQ ID NO 67
<211> LENGTH: 24
<212> TYPE: DNA
<213> ORGANISM: Artificial Sequence
<220> FEATURE:
<223> OTHER INFORMATION: AT12-007 Light chain CDR3

<400> SEQUENCE: 67
caacagtata ctacttattc cgcg                                       24

<210> SEQ ID NO 68
<211> LENGTH: 21
<212> TYPE: DNA
<213> ORGANISM: Artificial Sequence
<220> FEATURE:
<223> OTHER INFORMATION: AT12-009 Light chain CDR3

<400> SEQUENCE: 68
cagcagtata taactggcc t                                           21

<210> SEQ ID NO 69
<211> LENGTH: 21
<212> TYPE: DNA
<213> ORGANISM: Artificial Sequence
<220> FEATURE:
<223> OTHER INFORMATION: AT12-010 Light chain CDR3

<400> SEQUENCE: 69
ctacaaacta acaccttccc t                                               21

<210> SEQ ID NO 70
<211> LENGTH: 21
<212> TYPE: DNA
<213> ORGANISM: Artificial Sequence
<220> FEATURE:
<223> OTHER INFORMATION: AT13-021 Light chain CDR3

<400> SEQUENCE: 70
caccagtata atacctggcc c                                               21

<210> SEQ ID NO 71
<211> LENGTH: 360
<212> TYPE: DNA
<213> ORGANISM: Artificial Sequence
<220> FEATURE:
<223> OTHER INFORMATION: AT12-011 Heavy chain

<400> SEQUENCE: 71
caggtgcagc tggtgcagtc tggggctgag gtgaagaagc ccggtcctc ggtgaaggtc        60 tcctgcaagg cctctggagg caccttcagc ggatatggta tcacctgggt gcgacaggcc     120
cctggacaag gcttgagtg gatggggaca atcatccctg tttctgctac ggaaacctac      180
gcacagaggt tgcagggcag ggtcacaatt ccgcggacg aacattcaac acgtccctat      240
atggaggtga gcagcctgaa atctgaagac acggcccttt attactgtgc gagacacgac    300
tacttttggg ggactccgct tgatatctgg ggccaaggga cgatggtcat cgtctcttca    360

<210> SEQ ID NO 72
<211> LENGTH: 372
<212> TYPE: DNA
<213> ORGANISM: Artificial Sequence
<220> FEATURE:
<223> OTHER INFORMATION: AT12-007 Heavy chain

<400> SEQUENCE: 72
caggtccaac tggaacagtc tggggctgag gtgaagaagc ctggggcctc agtgaaggtc      60
tcctgcaagg tgtccggata caccctcact gagttatcca tgcactgggt gcgacaggct    120
cctggaaaag gcttgagtg gatgggcagt tttgatcctg cagatggtga aagactttac     180
gcacagaagt tccagggaag agtcatcatg agcgaagaca catctacaga cacagcctac   240
atggagttga gcagcctgag atctgaggac gcggccgtgt attactgtgc gactgcccca    300
cgtatgacga tgtttggggt gataatggcc ttagactcct ggggccaggg aaccctggtc    360
accgtctcct ca                                                        372

<210> SEQ ID NO 73
<211> LENGTH: 420
<212> TYPE: DNA
<213> ORGANISM: Artificial Sequence
<220> FEATURE:
<223> OTHER INFORMATION: AT12-009 Heavy chain

<400> SEQUENCE: 73
caggagcgcc tggtgcagtc tggggctgag gtgaagaagc ctgggtcctc ggtgagggtc      60
tcctgcaagg cttctggaga caccttcaag actcatgcca tcagtactca tgccatcagt   120
gggaccgtgc gacaggcccc cggagacggg cttgagttgc tgggagggtt cgtccccatc    180
cttgctccag cgaacgacgc ccagaagttc cagggcagag tcacgatcac cgcggacggg    240

```
tccacgggcc cagtctacat ggacctgagc accctgacat ctgaggacac ggccatgtat    300
tactgtgtga catcgctttc agaacccata ccaaggtctt gtcgtggtgg tagatgctac    360 tccggcccctt ttgatgcttt tggtgttttgg ggccaaggga caatggtcac cgtctcttca    420

<210> SEQ ID NO 74
<211> LENGTH: 381
<212> TYPE: DNA
<213> ORGANISM: Artificial Sequence
<220> FEATURE:
<223> OTHER INFORMATION: AT12-010 Heavy chain

<400> SEQUENCE: 74
caactgcaat tggtgcagtc tggggctgag gtgaagaagc ctgggtcctc ggtgaaggtc     60
tcctgcaagg cttctggagg caccttcacc agctatgcta tcaactgggt gcgacaggtc    120
cctggacaag gacttgagtg gatgggagag atcagccctg tctttggaac aacacactac    180
gcacagaagt tccagggcag actcaagatt accgcggacg aatccgcgga cacagcctac    240
atggagctga gcagcctgag atctgatgac acggccgttt attattgtgg gagagatagg    300 gccctagat tgtgtagtgg tggtcgctgc cactcccccc ctgaccactg ggccagggg    360 accctggtca ccgtctcctc a                                              381

<210> SEQ ID NO 75
<211> LENGTH: 378
<212> TYPE: DNA
<213> ORGANISM: Artificial Sequence
<220> FEATURE:
<223> OTHER INFORMATION: AT13-021 Heavy chain

<400> SEQUENCE: 75
caggtgcaac tggtgcagtc tggggctgag gtgaagaagc ctgggtcttc ggtgaaggtc     60
tcctgcaagg cttctggagg caccttcaac acccatgcat tcagctgggt gcgacaggcc    120
cctggagaag gccttgagtg gatggggggg atcagcccta tgtctggcac accaaactac    180
gcacagaaat tccagggcag actcaccatt accgcggacg aatccacgag cacaggctac    240
atggagctga gaagcctgac atctgaggac acggccgtgt attactgtgc gagagagttg    300
atcgggtatt gcactggtgg taactgctac tcattcggtg acttttgggg ccagggaacc    360
ctgattaccg tctcgtca                                                  378

<210> SEQ ID NO 76
<211> LENGTH: 336
<212> TYPE: DNA
<213> ORGANISM: Artificial Sequence
<220> FEATURE:
<223> OTHER INFORMATION: AT12-011 Light chain

<400> SEQUENCE: 76
gaaattgtgc tgactcagtc tccagacttt cagtctgtga ctccaaagga gaaagtcacc     60
atcacctgcc gggccagtca gagcattggt agtaatttac actggtacca gcagaaacca    120
ggtcagtctc caaagctcct catcaagtat gcttcccagt ccttctcagg ggtcccctcg    180
aggttcagtg gcagtggatc tgggactgat ttcacccctca ccatcaatag cctgaagct     240 gaagatgctg caacgtattt ctgtcatcag agttataatt taccgaggac tttcggcggg    300
gggaccaagg tggagatcaa acgaactgtg gctgca                              336

<210> SEQ ID NO 77
<211> LENGTH: 339
```

```
<212> TYPE: DNA
<213> ORGANISM: Artificial Sequence
<220> FEATURE:
<223> OTHER INFORMATION: AT12-007 Light chain

<400> SEQUENCE: 77
gacatccaga tgacccagtc tccttccacc ctgtctgcat ctttaggaga cagagttacc      60
atcacttgcc gggccagtca gaatattaat aaatatttgg cctggtatca gcagaaacca     120
gggaaagccc ctaaactcct catctataag gcgtctaatt tacaaagtgg ggtcccgtca     180
aggttcagcg gcagtggttc tgggacagac ttcattctca ccatcagcag cctgcaacct     240
gatgattttg caacttatta ctgccaacag tatactactt attccgcgtg gactttcggc     300
caagggacca acgtggacat caaacgaact gtggctgca                            339

<210> SEQ ID NO 78
<211> LENGTH: 336
<212> TYPE: DNA
<213> ORGANISM: Artificial Sequence
<220> FEATURE:
<223> OTHER INFORMATION: AT12-009 Light chain

<400> SEQUENCE: 78
gagacaatgt tgacgcagtc tccagtcacc ctgtctgtgt ctccagggga aagagccacc      60
ctctcctgca gggccagtca gagtattggt accaacttag cctggtacca gcagaagcct     120
ggccaggctc ccaggctcct cattcatggt gcatctacca gggccactgg tgtcccagtc     180
agtttcagtg gcagtgggtc tgggacagag ttcactctca ccatcagcag cctgcagtct     240
gaagattttg cagtctatta ctgccagcag tataataact ggcctctcac ttttggcgga     300
gggaccaagg tggacttcaa acgaactgtg gctgca                                336

<210> SEQ ID NO 79
<211> LENGTH: 336
<212> TYPE: DNA
<213> ORGANISM: Artificial Sequence
<220> FEATURE:
<223> OTHER INFORMATION: AT12-010 Light chain

<400> SEQUENCE: 79
gacatccaga tgacccagtc tccttcttcc gtgtctgcat ctgtaggcga cagagtcacc      60
atcacttgtc gggcgagtca gggttttggc aactggttag cctggtatca gcagaaacca     120
gggagggccc ctaagctcct gatctttggt gcatccactt tgcaaaatgg ggtcccatca     180
aggttcagcg gcagtgcgtc tgggacagat ttcactctca ccatcaccag cctgcagcct     240
gaagattttg caacctacta ttgtctacaa actaacacct cccttatac ttttggccag      300
gggaccaagg tggagatcaa acgaactgtg gctgca                                336

<210> SEQ ID NO 80
<211> LENGTH: 336
<212> TYPE: DNA
<213> ORGANISM: Artificial Sequence
<220> FEATURE:
<223> OTHER INFORMATION: AT13-021 Light chain

<400> SEQUENCE: 80
gaaatagtga tgacgcagtc tccagccacc ctgtctgtgt ctccagggga aagagccacc      60
ctctcctgca gggccagtca gagtgttagc agccacttag cctggtacca gcacaaacct     120
ggccaggctc ccaggctcct catctctggt gcatccacca gggccgttgg tgtcccagcc     180
```

```
aggttcagtg gcagtgggtc tgggacagag ttcactctca ccatcagcag cctgcagtct    240
gaggattttg cagtttatta ctgtcaccag tataatacct ggccccgggg gttcggccaa    300
gggaccaagg tggacttcaa acgaactgtg gctgca                              336
```

```
<210> SEQ ID NO 81
<211> LENGTH: 5
<212> TYPE: PRT
<213> ORGANISM: Artificial Sequence
<220> FEATURE:
<223> OTHER INFORMATION: AT15-009 Heavy chain CDR1

<400> SEQUENCE: 81

Thr Tyr Ala Ile Ser
1               5

<210> SEQ ID NO 82
<211> LENGTH: 5
<212> TYPE: PRT
<213> ORGANISM: Artificial Sequence
<220> FEATURE:
<223> OTHER INFORMATION: AT15-011 Heavy chain CDR1

<400> SEQUENCE: 82

Lys Tyr Tyr Trp Ser
1               5

<210> SEQ ID NO 83
<211> LENGTH: 5
<212> TYPE: PRT
<213> ORGANISM: Artificial Sequence
<220> FEATURE:
<223> OTHER INFORMATION: AT15-012 Heavy chain CDR1

<400> SEQUENCE: 83

Ile Phe Pro Ile Thr
1               5

<210> SEQ ID NO 84
<211> LENGTH: 5
<212> TYPE: PRT
<213> ORGANISM: Artificial Sequence
<220> FEATURE:
<223> OTHER INFORMATION: AT15-015 Heavy chain CDR1

<400> SEQUENCE: 84

Lys Tyr Tyr Trp Ser
1               5

<210> SEQ ID NO 85
<211> LENGTH: 17
<212> TYPE: PRT
<213> ORGANISM: Artificial Sequence
<220> FEATURE:
<223> OTHER INFORMATION: AT15-009 Heavy chain CDR2

<400> SEQUENCE: 85

Gly Ile Val Pro Met Phe Gly Ile Thr Asn Tyr Ala Gln His Phe Gln
1               5                   10                  15

Gly

<210> SEQ ID NO 86
<211> LENGTH: 16
<212> TYPE: PRT
<213> ORGANISM: Artificial Sequence
<220> FEATURE:
```

<223> OTHER INFORMATION: AT15-011 Heavy chain CDR2

<400> SEQUENCE: 86

Phe Ile Tyr Tyr Ser Gly Asn Thr Asn Tyr Asn Pro Ser Leu Lys Ser
1               5                   10                  15

<210> SEQ ID NO 87
<211> LENGTH: 17
<212> TYPE: PRT
<213> ORGANISM: Artificial Sequence
<220> FEATURE:
<223> OTHER INFORMATION: AT15-012 Heavy chain CDR2

<400> SEQUENCE: 87

Glu Ile Ile Pro Met Leu Gly Thr Pro Glu Tyr Ala Gln Lys Phe Gln
1               5                   10                  15

Gly

<210> SEQ ID NO 88
<211> LENGTH: 16
<212> TYPE: PRT
<213> ORGANISM: Artificial Sequence
<220> FEATURE:
<223> OTHER INFORMATION: AT15-015 Heavy chain CDR2

<400> SEQUENCE: 88

Phe Ile Tyr Tyr Ser Gly Ser Thr Asn Tyr Asn Pro Ser Leu Lys Ser
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: AT15-009 Heavy chain CDR3

<400> SEQUENCE: 89

Asp Leu Arg Ser Gly Gly Thr Phe Phe Ser Arg Gly Phe Asp Leu
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: AT15-011 Heavy chain CDR3

<400> SEQUENCE: 90

Gly Ala Arg Gly Ala Ser Gly Tyr Tyr Thr Asp Ser Phe Phe Asp Ser
1               5                   10                  15

<210> SEQ ID NO 91
<211> LENGTH: 17
<212> TYPE: PRT
<213> ORGANISM: Artificial Sequence
<220> FEATURE:
<223> OTHER INFORMATION: AT15-012 Heavy chain CDR3

<400> SEQUENCE: 91

Thr Glu Thr Thr Leu Pro Gly Thr Leu Phe Phe Val Tyr Tyr Phe His
1               5                   10                  15

Phe

<210> SEQ ID NO 92
<211> LENGTH: 16

```
<212> TYPE: PRT
<213> ORGANISM: Artificial Sequence
<220> FEATURE:
<223> OTHER INFORMATION: AT15-015 Heavy chain CDR3

<400> SEQUENCE: 92

Gly Ala Arg Gly Ser Ser Gly Tyr Tyr Thr Asp Ser Phe Phe Asp Ser
1               5                   10                  15

<210> SEQ ID NO 93
<211> LENGTH: 12
<212> TYPE: PRT
<213> ORGANISM: Artificial Sequence
<220> FEATURE:
<223> OTHER INFORMATION: AT15-009 Light chain CDR1

<400> SEQUENCE: 93

Arg Ala Ser Gln Ser Val Ser Ser Ser Phe Leu Thr
1               5                   10

<210> SEQ ID NO 94
<211> LENGTH: 11
<212> TYPE: PRT
<213> ORGANISM: Artificial Sequence
<220> FEATURE:
<223> OTHER INFORMATION: AT15-011 Light chain CDR1

<400> SEQUENCE: 94

Arg Ala Ser Gln Gly Phe Ser Asn Cys Leu Ala
1               5                   10

<210> SEQ ID NO 95
<211> LENGTH: 11
<212> TYPE: PRT
<213> ORGANISM: Artificial Sequence
<220> FEATURE:
<223> OTHER INFORMATION: AT15-012 Light chain CDR1

<400> SEQUENCE: 95

Arg Ala Ser Gln Ser Val Ser Ser Ser Leu Ala
1               5                   10

<210> SEQ ID NO 96
<211> LENGTH: 11
<212> TYPE: PRT
<213> ORGANISM: Artificial Sequence
<220> FEATURE:
<223> OTHER INFORMATION: AT15-015 Light chain CDR1

<400> SEQUENCE: 96

Arg Ala Ser Gln Gly Ile Ser Asn Tyr Leu Ala
1               5                   10

<210> SEQ ID NO 97
<211> LENGTH: 7
<212> TYPE: PRT
<213> ORGANISM: Artificial Sequence
<220> FEATURE:
<223> OTHER INFORMATION: AT15-009 Light chain CDR2

<400> SEQUENCE: 97

Asp Ala Ser Thr Arg Ala Thr
1               5

<210> SEQ ID NO 98
<211> LENGTH: 7
<212> TYPE: PRT
```

```
<213> ORGANISM: Artificial Sequence
<220> FEATURE:
<223> OTHER INFORMATION: AT15-011 Light chain CDR2

<400> SEQUENCE: 98

Ala Thr Ser Pro Leu Gln Ser
1               5

<210> SEQ ID NO 99
<211> LENGTH: 7
<212> TYPE: PRT
<213> ORGANISM: Artificial Sequence
<220> FEATURE:
<223> OTHER INFORMATION: AT15-012 Light chain CDR2

<400> SEQUENCE: 99

Gly Ala Ser Thr Arg Ala Thr
1               5

<210> SEQ ID NO 100
<211> LENGTH: 7
<212> TYPE: PRT
<213> ORGANISM: Artificial Sequence
<220> FEATURE:
<223> OTHER INFORMATION: AT15-015 Light chain CDR2

<400> SEQUENCE: 100

Ala Ala Ser Pro Leu Gln Ser
1               5

<210> SEQ ID NO 101
<211> LENGTH: 7
<212> TYPE: PRT
<213> ORGANISM: Artificial Sequence
<220> FEATURE:
<223> OTHER INFORMATION: AT15-009 Light chain CDR3

<400> SEQUENCE: 101

Gln Gln Phe Asp Ser Ser Pro
1               5

<210> SEQ ID NO 102
<211> LENGTH: 7
<212> TYPE: PRT
<213> ORGANISM: Artificial Sequence
<220> FEATURE:
<223> OTHER INFORMATION: AT15-011 Light chain CDR3

<400> SEQUENCE: 102

Gln Lys Tyr Asn Arg Ala Pro
1               5

<210> SEQ ID NO 103
<211> LENGTH: 8
<212> TYPE: PRT
<213> ORGANISM: Artificial Sequence
<220> FEATURE:
<223> OTHER INFORMATION: AT15-012 Light chain CDR3

<400> SEQUENCE: 103

Gln Gln Tyr Asn Asp Arg Pro Pro
1               5

<210> SEQ ID NO 104
<211> LENGTH: 7
<212> TYPE: PRT
<213> ORGANISM: Artificial Sequence
```

```
<220> FEATURE:
<223> OTHER INFORMATION: AT15-015 Light chain CDR3

<400> SEQUENCE: 104

Gln Asn Tyr Asn Arg Ala Pro
1               5

<210> SEQ ID NO 105
<211> LENGTH: 124
<212> TYPE: PRT
<213> ORGANISM: Artificial Sequence
<220> FEATURE:
<223> OTHER INFORMATION: AT15-009 Heavy chain

<400> SEQUENCE: 105

Gln Val Leu Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
                20                  25                  30

Ala Ile Ser Trp Leu Arg Gln Ala Pro Gly Gln Gly Pro Glu Trp Met
            35                  40                  45

Gly Gly Ile Val Pro Met Phe Gly Ile Thr Asn Tyr Ala Gln His Phe
        50                  55                  60

Gln Gly Arg Ile Thr Ile Thr Ala Asp Lys Ser Thr Ser Thr Ala Tyr
65                  70                  75                  80

Met Glu Leu Ser Ser Leu Gly Ser Glu Asp Thr Ala Val Tyr Phe Cys
                85                  90                  95

Ala Arg Asp Leu Arg Ser Gly Gly Thr Phe Phe Ser Arg Gly Phe Asp
            100                 105                 110

Leu Trp Gly Pro Gly Thr Lys Val Thr Val Ser Ser
        115                 120

<210> SEQ ID NO 106
<211> LENGTH: 124
<212> TYPE: PRT
<213> ORGANISM: Artificial Sequence
<220> FEATURE:
<223> OTHER INFORMATION: AT15-011 Heavy chain

<400> SEQUENCE: 106

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Lys Tyr
                20                  25                  30

Tyr Trp Ser Trp Val Arg Gln Pro Pro Gly Lys Gly Leu Glu Trp Ile
            35                  40                  45

Gly Phe Ile Tyr Tyr Ser Gly Asn Thr Asn Tyr Asn Pro Ser Leu Lys
        50                  55                  60

Ser Arg Val Thr Ile Ser Val Asp Thr Ser Asn Asn Lys Phe Ser Leu
65                  70                  75                  80

Lys Leu Ser Ser Ala Thr Ala Ala Asp Thr Ala Val Tyr Tyr Cys Ala
                85                  90                  95

Arg Gly Ala Arg Gly Ala Ser Gly Tyr Tyr Thr Asp Ser Phe Phe Asp
            100                 105                 110

Ser Trp Gly Gln Gly Ala Leu Val Thr Val Ser Ser
        115                 120

<210> SEQ ID NO 107
<211> LENGTH: 126
```

```
<212> TYPE: PRT
<213> ORGANISM: Artificial Sequence
<220> FEATURE:
<223> OTHER INFORMATION: AT15-012 Heavy chain

<400> SEQUENCE: 107

Gln Val Gln Leu Val Gln Ser Gly Ala Glu Val Lys Lys Pro Gly Ser
1               5                   10                  15

Ser Val Lys Val Ser Cys Lys Ala Ser Gly Gly Asn Phe Asn Ile Phe
                20                  25                  30

Pro Ile Thr Trp Val Arg Gln Ala Pro Gly Gln Gly Leu Glu Trp Met
            35                  40                  45

Gly Glu Ile Ile Pro Met Leu Gly Thr Pro Glu Tyr Ala Gln Lys Phe
    50                  55                  60

Gln Gly Arg Val Thr Ile Thr Ala Asp Lys Ser Thr Gly Thr Ala Phe
65                  70                  75                  80

Met Glu Leu Ser Ser Leu Arg Ser Glu Asp Thr Ala Val Tyr Tyr Cys
                85                  90                  95

Ala Arg Thr Glu Thr Thr Leu Pro Gly Thr Leu Phe Phe Val Tyr Tyr
            100                 105                 110

Phe His Phe Trp Gly Gln Gly Thr Pro Val Thr Val Ser Ser
        115                 120                 125

<210> SEQ ID NO 108
<211> LENGTH: 124
<212> TYPE: PRT
<213> ORGANISM: Artificial Sequence
<220> FEATURE:
<223> OTHER INFORMATION: AT15-015 Heavy chain

<400> SEQUENCE: 108

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Lys Tyr
                20                  25                  30

Tyr Trp Ser Trp Val Arg Gln Pro Pro Gly Lys Gly Leu Glu Trp Ile
            35                  40                  45

Gly Phe Ile Tyr Tyr Ser Gly Ser Thr Asn Tyr Asn Pro Ser Leu Lys
    50                  55                  60

Ser Arg Val Thr Ile Ser Val Asp Thr Ser Asn Asn Lys Phe Ser Leu
65                  70                  75                  80

Lys Val Thr Ser Ala Thr Ala Ala Asp Thr Ala Val Tyr Tyr Cys Ala
                85                  90                  95

Arg Gly Ala Arg Gly Ser Ser Gly Tyr Tyr Thr Asp Ser Phe Phe Asp
            100                 105                 110

Ser Trp Gly Gln Gly Ala Leu Val Thr Val Ser Ser
        115                 120

<210> SEQ ID NO 109
<211> LENGTH: 107
<212> TYPE: PRT
<213> ORGANISM: Artificial Sequence
<220> FEATURE:
<223> OTHER INFORMATION: AT15-009 Light chain

<400> SEQUENCE: 109

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
```

```
                20                  25                  30

Phe Leu Thr Trp Tyr Gln Gln Lys Pro Gly Gln Ala Pro Arg Leu Leu
            35                  40                  45

Ile Phe Asp Ala Ser Thr Arg Ala Thr Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Gly Val Tyr Tyr Cys Gln Gln Phe Asp Ser Ser Pro
                85                  90                  95

Thr Phe Gly Gly Gly Thr Lys Val Glu Ile Lys
            100                 105

<210> SEQ ID NO 110
<211> LENGTH: 104
<212> TYPE: PRT
<213> ORGANISM: Artificial Sequence
<220> FEATURE:
<223> OTHER INFORMATION: AT15-011 Light chain

<400> SEQUENCE: 110

Asp Ile Gln Met Thr Gln Ser Pro Ser Ser Leu Ser Ala Ser Val Gly
1               5                   10                  15

Asp Arg Ile Thr Ile Thr Cys Arg Ala Ser Gln Gly Phe Ser Asn Cys
                20                  25                  30

Leu Ala Trp Cys Gln Gln Lys Pro Gly Thr Val Leu Lys Leu Leu Ile
            35                  40                  45

Tyr Ala Thr Ser Pro Leu Gln Ser Gly Val Pro Ser Arg Phe Ser Asp
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Arg Ala Pro Leu
                85                  90                  95

Pro Gly Thr Thr Val Asp Ile Lys
            100

<210> SEQ ID NO 111
<211> LENGTH: 108
<212> TYPE: PRT
<213> ORGANISM: Artificial Sequence
<220> FEATURE:
<223> OTHER INFORMATION: AT15-012 Light chain

<400> SEQUENCE: 111

Glu Ile Val Met Thr Gln Ser Pro Val Thr Leu Ser Val Ser Pro Gly
1               5                   10                  15

Glu Arg Ala Ile Leu Ser Cys Arg Ala Ser Gln Ser Val Ser Ser Ser
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Val Pro Ala Arg Phe Ser Gly
    50                  55                  60

Ser Gly Ser Gly Thr Glu Phe Thr Leu Thr Ile Ser Ser Val Gln Ser
65                  70                  75                  80

Glu Asp Tyr Ala Ile Tyr Phe Cys Gln Gln Tyr Asn Asp Arg Pro Pro
                85                  90                  95

Trp Thr Phe Gly Gln Gly Thr Lys Val Glu Ile Lys
            100                 105
```

<210> SEQ ID NO 112
<211> LENGTH: 104
<212> TYPE: PRT
<213> ORGANISM: Artificial Sequence
<220> FEATURE:
<223> OTHER INFORMATION: AT15-015 Light chain

<400> SEQUENCE: 112

```
Asp Ile Gln Met Thr Gln Ser Pro Ser Ser Leu Ser Ala Ser Val Gly
1               5                   10                  15

Asp Arg Ile Thr Ile Thr Cys Arg Ala Ser Gln Gly Ile Ser Asn Tyr
            20                  25                  30

Leu Ala Trp Tyr Gln Gln Lys Pro Gly Ala Val Leu Asn Leu Pro Ile
        35                  40                  45

Tyr Ala Ala Ser Pro Leu Gln Ser Gly Val Pro Ser Arg Phe Ser Asp
    50                  55                  60

Ser Gly Ser Gly Thr Asp Phe Thr Leu Thr Ile Thr Ser Leu Gln Pro
65                  70                  75                  80

Glu Asp Val Ala Thr Tyr Tyr Cys Gln Asn Tyr Asn Arg Ala Pro Leu
                85                  90                  95

Pro Gly Thr Lys Val Asp Ile Lys
            100
```

<210> SEQ ID NO 113
<211> LENGTH: 15
<212> TYPE: DNA
<213> ORGANISM: Artificial Sequence
<220> FEATURE:
<223> OTHER INFORMATION: AT15-009 Heavy chain CDR1

<400> SEQUENCE: 113
acctatgcta tcagc                                                    15

<210> SEQ ID NO 114
<211> LENGTH: 15
<212> TYPE: DNA
<213> ORGANISM: Artificial Sequence
<220> FEATURE:
<223> OTHER INFORMATION: AT15-011 Heavy chain CDR1

<400> SEQUENCE: 114
aaatactact ggagc                                                    15

<210> SEQ ID NO 115
<211> LENGTH: 15
<212> TYPE: DNA
<213> ORGANISM: Artificial Sequence
<220> FEATURE:
<223> OTHER INFORMATION: AT15-012 Heavy chain CDR1

<400> SEQUENCE: 115
atttttccta tcacc                                                    15

<210> SEQ ID NO 116
<211> LENGTH: 15
<212> TYPE: DNA
<213> ORGANISM: Artificial Sequence
<220> FEATURE:
<223> OTHER INFORMATION: AT15-015 Heavy chain CDR1

<400> SEQUENCE: 116
aaatactact ggagc                                                    15

<210> SEQ ID NO 117
<211> LENGTH: 51
<212> TYPE: DNA
<213> ORGANISM: Artificial Sequence
<220> FEATURE:
<223> OTHER INFORMATION: Heavy chain CDR2

<400> SEQUENCE: 117
gggatcgtcc ctatgtttgg tattacaaac tacgcacagc atttccaggg c        51

<210> SEQ ID NO 118
<211> LENGTH: 48
<212> TYPE: DNA
<213> ORGANISM: Artificial Sequence
<220> FEATURE:
<223> OTHER INFORMATION: AT15-011 Heavy chain CDR2

<400> SEQUENCE: 118
tttatctatt acagtgggaa caccaactac aacccctccc tcaagagt             48

<210> SEQ ID NO 119
<211> LENGTH: 51
<212> TYPE: DNA
<213> ORGANISM: Artificial Sequence
<220> FEATURE:
<223> OTHER INFORMATION: AT15-012 Heavy chain CDR2

<400> SEQUENCE: 119
gagatcatcc ctatgttagg gacacctgag tacgcacaga gttccaggg c           51

<210> SEQ ID NO 120
<211> LENGTH: 48
<212> TYPE: DNA
<213> ORGANISM: Artificial Sequence
<220> FEATURE:
<223> OTHER INFORMATION: AT15-015 Heavy chain CDR2

<400> SEQUENCE: 120
tttatctatt acagtgggag caccaactac aacccctccc tcaagagt             48

<210> SEQ ID NO 121
<211> LENGTH: 45
<212> TYPE: DNA
<213> ORGANISM: Artificial Sequence
<220> FEATURE:
<223> OTHER INFORMATION: AT15-009 Heavy chain CDR3

<400> SEQUENCE: 121
gatctgcgta gtggtgggac tttttttctct cgtggttttg attta               45

<210> SEQ ID NO 122
<211> LENGTH: 48
<212> TYPE: DNA
<213> ORGANISM: Artificial Sequence
<220> FEATURE:
<223> OTHER INFORMATION: AT15-011 Heavy chain CDR3

<400> SEQUENCE: 122
ggtgcccgag gtgctagtgg ttattacacc gattcttttt ttgactcc             48

<210> SEQ ID NO 123
<211> LENGTH: 51
<212> TYPE: DNA
<213> ORGANISM: Artificial Sequence
<220> FEATURE:
<223> OTHER INFORMATION: AT15-012  Heavy chain CDR3

<400> SEQUENCE: 123
acggaaacaa ctctacctgg aacactcttt ttcgtttact actttcactt c         51

<210> SEQ ID NO 124
<211> LENGTH: 48
<212> TYPE: DNA
<213> ORGANISM: Artificial Sequence
<220> FEATURE:
<223> OTHER INFORMATION: AT15-015 Heavy chain CDR3

<400> SEQUENCE: 124
ggtgcccgag gtagtagtgg ttattacacc gattctttt ttgactcc              48

<210> SEQ ID NO 125
<211> LENGTH: 36
<212> TYPE: DNA
<213> ORGANISM: Artificial Sequence
<220> FEATURE:
<223> OTHER INFORMATION: AT15-009 Light chain CDR1

<400> SEQUENCE: 125
agggccagtc agagtgttag cagcagcttc ttaacc                          36

<210> SEQ ID NO 126
<211> LENGTH: 33
<212> TYPE: DNA
<213> ORGANISM: Artificial Sequence
<220> FEATURE:
<223> OTHER INFORMATION: AT15-011 Light chain CDR1

<400> SEQUENCE: 126
cgggcgagtc agggctttag caattgttta gcc                             33

<210> SEQ ID NO 127
<211> LENGTH: 33
<212> TYPE: DNA
<213> ORGANISM: Artificial Sequence
<220> FEATURE:
<223> OTHER INFORMATION: AT15-012 Light chain CDR1

<400> SEQUENCE: 127
agggccagtc agagtgttag cagcagctta gcc                             33

<210> SEQ ID NO 128
<211> LENGTH: 33
<212> TYPE: DNA
<213> ORGANISM: Artificial Sequence
<220> FEATURE:
<223> OTHER INFORMATION: AT15-015 Light chain CDR1

<400> SEQUENCE: 128
cgggcgagtc agggcattag caattattta gcc                             33

<210> SEQ ID NO 129
<211> LENGTH: 21
<212> TYPE: DNA
<213> ORGANISM: Artificial Sequence
<220> FEATURE:
<223> OTHER INFORMATION: AT15-009 Light chain CDR2

<400> SEQUENCE: 129
gatgcatcca ccagggccac t                                          21

<210> SEQ ID NO 130

```
<211> LENGTH: 21
<212> TYPE: DNA
<213> ORGANISM: Artificial Sequence
<220> FEATURE:
<223> OTHER INFORMATION: AT15-011 Light chain CDR2

<400> SEQUENCE: 130
gctacatccc ctttgcaatc a                                              21

<210> SEQ ID NO 131
<211> LENGTH: 21
<212> TYPE: DNA
<213> ORGANISM: Artificial Sequence
<220> FEATURE:
<223> OTHER INFORMATION: AT15-012 Light chain CDR2

<400> SEQUENCE: 131
ggtgcatcca ccagggccac t                                              21

<210> SEQ ID NO 132
<211> LENGTH: 21
<212> TYPE: DNA
<213> ORGANISM: Artificial Sequence
<220> FEATURE:
<223> OTHER INFORMATION: AT15-015 Light chain CDR2

<400> SEQUENCE: 132
gctgcatccc ctttgcaatc a                                              21

<210> SEQ ID NO 133
<211> LENGTH: 21
<212> TYPE: DNA
<213> ORGANISM: Artificial Sequence
<220> FEATURE:
<223> OTHER INFORMATION: AT15-009 Light chain CDR3

<400> SEQUENCE: 133
cagcagtttg atagttctcc c                                              21

<210> SEQ ID NO 134
<211> LENGTH: 21
<212> TYPE: DNA
<213> ORGANISM: Artificial Sequence
<220> FEATURE:
<223> OTHER INFORMATION: AT15-011 Light chain CDR3

<400> SEQUENCE: 134
caaaagtata acagagcccc c                                              21

<210> SEQ ID NO 135
<211> LENGTH: 24
<212> TYPE: DNA
<213> ORGANISM: Artificial Sequence
<220> FEATURE:
<223> OTHER INFORMATION: AT15-012 Light chain CDR3

<400> SEQUENCE: 135
caacagtata atgacaggcc tccg                                           24

<210> SEQ ID NO 136
<211> LENGTH: 21
<212> TYPE: DNA
<213> ORGANISM: Artificial Sequence
<220> FEATURE:
<223> OTHER INFORMATION: AT15-015 Light chain CDR3

<400> SEQUENCE: 136
```

```
caaaactata acagagcccc c                                              21
```

<210> SEQ ID NO 137
<211> LENGTH: 372
<212> TYPE: DNA
<213> ORGANISM: Artificial Sequence
<220> FEATURE:
<223> OTHER INFORMATION: AT15-009 Heavy chain

<400> SEQUENCE: 137

```
caggtgcttc tggtgcagtc tggggctgag gtgaagaagc ctgggtcctc ggtgaaagtc     60
tcctgtaagg cttctggagg caccttcagc acctatgcta tcagctggct gcgacaggcc    120
cctggccaag ggcctgagtg gatgggaggg atcgtcccta tgtttggtat tacaaactac    180
gcacagcatt tccagggcag aatcaccatt accgcggaca atccacgag cacagcctac    240
atggaactga gcagcctggg atctgaggac acggccgtgt attttgtgc gagagatctg    300
cgtagtggtg ggacttttt ctctcgtggt tttgatttat ggggcccagg gacaaaggtc    360
accgtctctt ca                                                       372
```

<210> SEQ ID NO 138
<211> LENGTH: 372
<212> TYPE: DNA
<213> ORGANISM: Artificial Sequence
<220> FEATURE:
<223> OTHER INFORMATION: AT15-011 Heavy chain

<400> SEQUENCE: 138

```
caggtgcagc tgcaggagtc gggcccagga ctggtgaagc cttcggagac cctgtccctc     60
acctgcacgg tctctggtga ctccatcagt aaatactact ggagctgggt ccggcagccc    120
ccagggaagg gactggagtg gattggtttt atctattaca gtgggaacac caactacaac    180
ccctccctca agagtcgagt caccatatca gtagacacgt ccaacaacaa gttctccctg    240
aaactgagct ctgcgaccgc tgcggacacg gccgtgtatt actgtgcgag aggtgcccga    300
ggtgctagtg gttattacac cgattctttt tttgactcct ggggccaggg agccctggtc    360
accgtctcct ca                                                       372
```

<210> SEQ ID NO 139
<211> LENGTH: 378
<212> TYPE: DNA
<213> ORGANISM: Artificial Sequence
<220> FEATURE:
<223> OTHER INFORMATION: AT15-012 Heavy chain

<400> SEQUENCE: 139

```
caggtgcagc tggtgcagtc tggggctgag gtgaagaagc ctgggtcctc ggtgaaggtc     60
tcctgcaagg cttctggagg caacttcaac atttttccta tcacctgggt gcgacaggcc    120
cctggacaag ggcttgagtg gatggcgag atcatcccta tgttagggac acctgagtac    180
gcacagaagt tccagggcag agtcacgata accgcggaca atccacggg cactgccttc    240
atggagctga gcagcctgag atctgaggac acggccgttt attactgtgc tagaacggaa    300
acaactctac ctggaacact cttttttcgtt tactactttc acttctgggg ccagggaacc    360
ccggtcaccg tctcctca                                                 378
```

<210> SEQ ID NO 140
<211> LENGTH: 372
<212> TYPE: DNA

```
<213> ORGANISM: Artificial Sequence
<220> FEATURE:
<223> OTHER INFORMATION: AT15-015 Heavy chain

<400> SEQUENCE: 140
caggtgcagc tgcaggagtc gggcccagga ctggtgaagc cttcggagac cctgtccctc      60
acctgcactg tctctggtga ctccatcagt aaatactact ggagctgggt ccggcagccc     120
ccaggaaagg gactggagtg gattgggttt atctattaca gtgggagcac caactacaac     180
ccctccctca agagtcgagt caccatatca gtagacacgt ccaacaacaa gttctccctg     240
aaggtgacct ctgcgaccgc tgcggacacg gccgtgtatt actgtgcgag aggtgcccga     300
ggtagtagtg gttattacac cgattctttt tttgactcct ggggccaggg agccctcgtc     360
accgtctcct ca                                                        372

<210> SEQ ID NO 141
<211> LENGTH: 321
<212> TYPE: DNA
<213> ORGANISM: Artificial Sequence
<220> FEATURE:
<223> OTHER INFORMATION: AT15-009 Light chain

<400> SEQUENCE: 141
gaaattgtgt tgacgcagtc tccaggcacc ctgtctttgt ctccagggga aagagccacc      60
ctctcctgca gggccagtca gagtgttagc agcagcttct taacctgtta ccagcagaaa     120
cctggccagg ctcccaggct cctcatcttt gatgcatcca ccagggccac tggcgtccca     180
gacaggttca gtggcagtgg gtctgggaca gacttcactc tcaccatcag cagactggag     240
cctgaagatt ttggagtcta ttactgtcag cagtttgata gttctcccac tttcggcgga     300
gggaccaagg tggagatcaa a                                              321

<210> SEQ ID NO 142
<211> LENGTH: 312
<212> TYPE: DNA
<213> ORGANISM: Artificial Sequence
<220> FEATURE:
<223> OTHER INFORMATION: AT15-011 Light chain

<400> SEQUENCE: 142
gacatccaga tgacccagtc tccatcctcc ctgtctgcat ctgtaggaga cagaatcacc      60
atcacttgcc gggcgagtca gggctttagc aattgtttag cctggtgtca gcagaaacca     120
gggacagttc ttaagcttct gatctatgct acatccccct tgcaatcagg gtcccatct     180 cggttcagtg acagtggatc tgggacagat ttcactctca ccatcagcag cctgcagcct     240
gaagatgttg caacttatta ctgtcaaaag tataacagag ccccccctccc tggaccaca     300 gtggatatca aa                                                        312

<210> SEQ ID NO 143
<211> LENGTH: 324
<212> TYPE: DNA
<213> ORGANISM: Artificial Sequence
<220> FEATURE:
<223> OTHER INFORMATION: AT15-012 Light chain

<400> SEQUENCE: 143
gaaatagtga tgacgcagtc tccagtcacc ctgtctgtgt ctccagggga aagagccatc      60
ctctcctgca gggccagtca gagtgttagc agcagcttag cctggtacca gcagaaacct     120
ggccaggctc ccaggctcct catctatggt gcatccacca gggccactgg tgtcccagcc     180
```

```
aggttcagtg gcagtgggtc tgggacagag ttcactctca ccatcagcag cgtgcagtct    240
gaagattacg caatttattt ctgtcaacag tataatgaca ggcctccgtg gacgttcggc    300
caagggacca aggtggagat caaa                                          324
```

<210> SEQ ID NO 144
<211> LENGTH: 312
<212> TYPE: DNA
<213> ORGANISM: Artificial Sequence
<220> FEATURE:
<223> OTHER INFORMATION: AT15-015 Light chain

<400> SEQUENCE: 144

```
gacatccaga tgacccagtc tccatcctcc ctgtctgcat ctgtaggaga cagaatcacc    60
atcacttgcc gggcgagtca gggcattagc aattatttag cctggtatca gcagaaacca   120
ggggcagttc ttaaccttcc gatctatgct gcatcccctt tgcaatcagg ggtcccatct   180
cggttcagtg acagtggatc tgggacagat ttcactctca ccatcaccag cctgcagcct   240
gaagatgttg caacttatta ctgtcaaaac tataacagag cccccctccc tgggaccaaa   300
gtggatatca aa                                                      312
```

<210> SEQ ID NO 145
<211> LENGTH: 363
<212> TYPE: PRT
<213> ORGANISM: Hepatitis C virus

<400> SEQUENCE: 145

```
Glu Thr His Val Thr Gly Gly Ser Ala Gly His Thr Thr Ala Gly Leu
1               5                   10                  15

Val Gly Leu Leu Thr Pro Gly Ala Lys Gln Asn Ile Gln Leu Ile Asn
                20                  25                  30

Thr Asn Gly Ser Trp His Ile Asn Ser Thr Ala Leu Asn Cys Asn Asp
            35                  40                  45

Ser Leu Thr Thr Gly Trp Leu Ala Gly Leu Phe Tyr Arg His Lys Phe
        50                  55                  60

Asn Ser Ser Gly Cys Pro Glu Arg Leu Ala Ser Cys Arg Arg Leu Thr
65                  70                  75                  80

Asp Phe Ala Gln Gly Trp Gly Pro Ile Ser Tyr Ala Asn Gly Ser Gly
                85                  90                  95

Leu Asp Glu Arg Pro Tyr Cys Trp His Tyr Pro Pro Arg Pro Cys Gly
                100                 105                 110

Ile Val Pro Ala Lys Ser Val Cys Gly Pro Val Tyr Cys Phe Thr Pro
            115                 120                 125

Ser Pro Val Val Val Gly Thr Thr Asp Arg Ser Gly Ala Pro Thr Tyr
        130                 135                 140

Ser Trp Gly Ala Asn Asp Thr Asp Val Phe Val Leu Asn Asn Thr Arg
145                 150                 155                 160

Pro Pro Leu Gly Asn Trp Phe Gly Cys Thr Trp Met Asn Ser Thr Gly
                165                 170                 175

Phe Thr Lys Val Cys Gly Ala Pro Pro Cys Val Ile Gly Gly Val Gly
                180                 185                 190

Asn Asn Thr Leu Leu Cys Pro Thr Asp Cys Phe Arg Lys His Pro Glu
            195                 200                 205

Ala Thr Tyr Ser Arg Cys Gly Ser Gly Pro Trp Ile Thr Pro Arg Cys
        210                 215                 220
```

Met Val Asp Tyr Pro Tyr Arg Leu Trp His Tyr Pro Cys Thr Ile Asn
225                 230                 235                 240

Tyr Thr Ile Phe Lys Val Arg Met Tyr Val Gly Gly Val Glu His Arg
                245                 250                 255

Leu Glu Ala Ala Cys Asn Trp Thr Arg Gly Glu Arg Cys Asp Leu Glu
            260                 265                 270

Asp Arg Asp Arg Ser Glu Leu Ser Pro Leu Leu Leu Ser Thr Thr Gln
        275                 280                 285

Trp Gln Val Leu Pro Cys Ser Phe Thr Thr Leu Pro Ala Leu Ser Thr
    290                 295                 300

Gly Leu Ile His Leu His Gln Asn Ile Val Asp Val Gln Tyr Leu Tyr
305                 310                 315                 320

Gly Val Gly Ser Ser Ile Ala Ser Trp Ala Ile Lys Trp Glu Tyr Val
                325                 330                 335

Val Leu Leu Phe Leu Leu Leu Ala Asp Ala Arg Val Cys Ser Cys Leu
                340                 345                 350

Trp Met Met Leu Leu Ile Ser Gln Ala Glu Ala
            355                 360

<210> SEQ ID NO 146
<211> LENGTH: 367
<212> TYPE: PRT
<213> ORGANISM: Hepatitis C virus

<400> SEQUENCE: 146

Thr Thr Tyr Ser Thr Gly Gly Gln Val Ser Arg Thr Thr Ser Ser Phe
1               5                   10                  15

Val Gly Leu Phe Ala His Gly Pro Gln Gln Lys Leu Ser Leu Ile Asn
                20                  25                  30

Thr Asn Gly Ser Trp His Ile Asn Arg Thr Ala Leu Asn Cys Asn Asp
            35                  40                  45

Ser Leu Gln Thr Gly Phe Leu Ala Ser Leu Phe Tyr Thr Arg Asn Phe
        50                  55                  60

Asn Ser Ser Gly Cys Pro Glu Arg Leu Ser Ser Cys Arg Thr Leu Asp
65                  70                  75                  80

Asp Phe Arg Ile Gly Trp Gly Thr Leu Glu Tyr Glu Thr Asn Val Ile
                85                  90                  95

Asn Asp Glu Asp Val Arg Pro Tyr Cys Trp His Tyr Pro Pro Lys Pro
            100                 105                 110

Cys Gly Ile Val Ser Ala Arg Thr Val Cys Gly Pro Val Tyr Cys Phe
        115                 120                 125

Thr Pro Ser Pro Val Val Val Gly Thr Thr Asp Arg Gln Gly Val Pro
    130                 135                 140

Thr Tyr Ser Trp Gly Glu Asn Glu Thr Asp Val Phe Leu Leu Asn Ser
145                 150                 155                 160

Thr Arg Pro Pro Gln Gly Ala Trp Phe Gly Cys Thr Trp Met Asn Gly
                165                 170                 175

Thr Gly Phe Thr Lys Thr Cys Gly Ala Pro Pro Cys Arg Ile Arg Arg
            180                 185                 190

Asp Tyr Asn Gly Thr Leu Asp Leu Leu Cys Pro Thr Asp Cys Phe Arg
        195                 200                 205

Lys His Pro Glu Thr Thr Tyr Leu Arg Cys Gly Ser Gly Pro Trp Leu
    210                 215                 220

Thr Pro Arg Cys Leu Val Asp Tyr Pro Tyr Arg Leu Trp His Tyr Pro
225                 230                 235                 240

```
Cys Thr Val Asn Phe Thr Ile Phe Lys Val Arg Met Tyr Val Gly Gly
                245                 250                 255

Val Glu His Arg Leu Pro Ala Ala Cys Asn Phe Thr Arg Gly Asp Arg
            260                 265                 270

Cys Arg Leu Glu Asp Arg Asp Arg Gly Gln Gln Ser Pro Leu Leu His
            275                 280                 285

Ser Thr Thr Glu Trp Ala Val Met Pro Cys Ser Phe Ser Asp Leu Pro
290                 295                 300

Ala Leu Ser Thr Gly Leu Leu His Leu His Gln Asn Ile Val Asp Val
305                 310                 315                 320

Gln Tyr Leu Tyr Gly Leu Ser Pro Ala Ile Thr Arg Tyr Ile Val Lys
                325                 330                 335

Trp Glu Trp Val Val Leu Leu Phe Leu Leu Leu Ala Asp Ala Arg Val
            340                 345                 350

Cys Ala Cys Leu Trp Met Leu Ile Ile Leu Gly Gln Ala Glu Ala
                355                 360                 365

<210> SEQ ID NO 147
<211> LENGTH: 192
<212> TYPE: PRT
<213> ORGANISM: Hepatitis C virus

<400> SEQUENCE: 147

Tyr Gln Val Arg Asn Ser Ser Gly Leu Tyr His Val Thr Asn Asp Cys
1               5                   10                  15

Pro Asn Ser Ser Ile Val Tyr Glu Ala Ala Asp Ala Ile Leu His Thr
                20                  25                  30

Pro Gly Cys Val Pro Cys Val Arg Glu Gly Asn Ala Ser Arg Cys Trp
            35                  40                  45

Val Ala Val Thr Pro Thr Val Ala Thr Arg Asp Gly Lys Leu Pro Thr
        50                  55                  60

Thr Gln Leu Arg Arg His Ile Asp Leu Leu Val Gly Ser Ala Thr Leu
65                  70                  75                  80

Cys Ser Ala Leu Tyr Val Gly Asp Leu Cys Gly Ser Val Phe Leu Val
                85                  90                  95

Gly Gln Leu Phe Thr Phe Ser Pro Arg Arg His Trp Thr Thr Gln Ser
            100                 105                 110

Cys Asn Cys Ser Ile Tyr Pro Gly His Ile Thr Gly His Arg Met Ala
        115                 120                 125

Trp Asp Met Met Met Asn Trp Ser Pro Thr Ala Ala Leu Val Val Ala
    130                 135                 140

Gln Leu Leu Arg Ile Pro Gln Ala Ile Met Asp Met Ile Ala Gly Ala
145                 150                 155                 160

His Trp Gly Val Leu Ala Gly Ile Ala Tyr Phe Ser Met Val Gly Asn
                165                 170                 175

Trp Ala Lys Val Leu Val Val Leu Leu Leu Phe Ala Gly Val Asp Ala
            180                 185                 190
```